United States Patent
Saed

(10) Patent No.: US 11,180,560 B2
(45) Date of Patent: *Nov. 23, 2021

(54) COMPOSITIONS AND METHODS TO TREAT SOLID TUMORS

(71) Applicant: Wayne State University, Detroit, MI (US)

(72) Inventor: Ghassan M. Saed, Bloomfield Hills, MI (US)

(73) Assignee: Wayne State University, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,456

(22) Filed: May 20, 2019

(65) Prior Publication Data

US 2019/0309073 A1 Oct. 10, 2019

Related U.S. Application Data

(62) Division of application No. 15/338,092, filed on Oct. 28, 2016, now Pat. No. 10,336,827.

(60) Provisional application No. 62/332,397, filed on May 5, 2016, provisional application No. 62/248,144, filed on Oct. 29, 2015.

(51) Int. Cl.
| | | |
|---|---|---|
| *C07K 16/40* | (2006.01) | |
| *C07K 16/28* | (2006.01) | |
| *C07K 14/435* | (2006.01) | |
| *A61K 39/395* | (2006.01) | |
| *A61K 39/00* | (2006.01) | |

(52) U.S. Cl.
CPC .... *C07K 16/2848* (2013.01); *A61K 39/39558* (2013.01); *C07K 14/4354* (2013.01); *C07K 16/2842* (2013.01); *C07K 16/2845* (2013.01); *C07K 16/40* (2013.01); *A61K 2039/505* (2013.01); *C07K 2317/24* (2013.01); *C07K 2317/55* (2013.01); *C07K 2317/73* (2013.01)

(58) Field of Classification Search
CPC .............. C07K 16/2848; C07K 16/2845; C07K 16/40; C07K 16/2842; A61K 39/39558
USPC ...................................... 424/133.1
See application file for complete search history.

(56) References Cited

U.S. PATENT DOCUMENTS

| | | |
|---|---|---|
| 9,023,876 B2 | 5/2015 | Gupta |
| 2014/0303026 A1 | 10/2014 | Gupta et al. |
| 2017/0121410 A1 | 5/2017 | Saed |

FOREIGN PATENT DOCUMENTS

| | | |
|---|---|---|
| WO | WO200216584 A2 | 2/2002 |
| WO | WO200232446 A2 | 4/2002 |

OTHER PUBLICATIONS

Saed et al. (Gynecologic Oncology, 2010, 116: 276-281).*
Bazou, et al., "Elucidation of flow-mediated tumour cell-induced platelet aggregation using an ultrasound standing wave trap", British Journal of Pharmacology, vol. No. 162, 2011, pp. 1577-1589.
"Clinical Trials", retrieved on Oct. 23, 2015, at: <http://www.ocrf.org/about-ovarian-cancer/clinical-trials>, Ovarian Cancer Research Fund, 2012, 5 pages.
Office Action for U.S. Appl. No. 15/338,092, dated Nov. 13, 2018, Saed, "Compositions and Methods to Treat Solid Tumors", 6 pages.
Office Action for U.S. Appl. No. 15/338,092, dated Jun. 7, 2018, Saed, "Compositions and Methods to Treat Solid Tumors", 7 pages.
"Ovarian cancer Market—Global Industry Analysis, Size, Share, Trends, Analysis, Growth and Forecast 2014-2020," retrieved on Oct. 23, 2015, at <http://www.transparencymarketresearch.com/ovarian-cancer-market.html>, Transparency Market Research, 3 pages.
Podolnikova, et al., "Ligand Recognition Specificity of Leukocyte Integrin aMbeta2 (Mac-1, CD11b/CD18) and Its Functional Consequences," Biochemistry, vol. 54, No. 6, 2015, pp. 1408-1420.
Rajput, et al., "TLR is a Novel Determinant of the Response to Paclitaxel in Breast Cancer," Molecular Cancer Therapy, vol. 12, No. 8, 2013, pp. 1676-1687.
Sadhu, et al., "CD11c/CD18: Novel Ligands and a Role in Delayed-Type Hypersensitivity," Journal of Leukocyte Biology, vol. 81, No. 6, 2007, pp. 1395-1403.
"The Ovarian Cancer Drug Market Will More Than Triple Over the Next Decade, Increasing from $460 Million in 2011 to $1.4 Billion in 2021," retrieved on Oct. 23, 2015, at http://www.fiercebiotech.com/press-releases/ovarian-cancer-drug-market-will-more-triple-over-next-decade-increasing-460, FierceBiotech, 3 pages.
Waldmann, et al., "Emerging Therapies: Spectrum of Applications of Monoclonal Antibody Therapy", American Society of Hematology, 2000, pp. 394-408.

\* cited by examiner

*Primary Examiner* — Yan Xiao
(74) *Attorney, Agent, or Firm* — Tanya M. Harding; Lee & Hayes, P.C.

(57) ABSTRACT

Compositions and methods that utilize anti-CD11b antibodies, anti-CD18 antibodies, anti-myeloperoxidase (MPO) antibodies, anti-integrin αV antibodies, anti-integrin β1 antibodies, Abciximab, neutrophil inhibitory factor (NIF) protein, and/or combinations thereof to treat solid tumors are described.

18 Claims, 27 Drawing Sheets

Specification includes a Sequence Listing.

FIG. 19

MALRVLLLTALTLCHGFNLDTENAMTFQENARGFGQSVVQLQGSRVVVG
APQEIVAANQRGSLYQCDYSTGSCEPIRLQVPVEAVNMSLGLSLAATTSP
PQLLACGPTVHQTCSENTYVKGLCFLGSNLRQQPQKFPEALRGCPQED
SDIAFLIDGSGSIIPHDFRRMKEFVSTVMEQLKKSKTLFSLMQYSEEFRIHF
TFKEFQNNPNPRSLVKPITQLLGRTHTATGIRKVVRELFNITNGARKNAFKI
LVVITDGEKFGDPLGYEDVIPEADREGVIRYVIGVGDAFRSEKSRQELNTI
ASKPPRDHVFQVNNFEALKTIQNQLREKIFAIEGTQTGSSSSFEHEMSQE
GFSAAITSNGPLLSTVGSYDWAGGVFLYTSKEKSTFINMTRVDSDMNDAY
LGYAAAIILRNRVQSLVLGAPRYQHIGLVAMFRQNTGMWESNANVKGTQI
GAYFGASLCSVDVDSNGSTDLVLIGAPHYYEQTRGGQVSVCPLPRGRAR
WQCDAVLYGEQGQPWGRFGAALTVLGDVNGDKLTDVAIGAPGEEDNR
GAVYLFHGTSGSGISPSHSQRIAGSKLSPRLQYFGQSLSGGQDLTMDGL
VDLTVGAQGHVLLLRSQPVLRVKAIMEFNPREVARNVFECNDQVVKGKE
AGEVRVCLHVQKSTRDRLREGGQIQSVVTYDLALDSGRPHSRAVFNETKN
STRRQTQVLGLTQTCETLKLQLPNCIEDPVSPIVLRLNFSLVGTPLSAFGN
LRPVLAEDAQRLFTALFPFEKNCGNDNICQDDLSITFSFMSLDCLVVGGP
REFNVTVTVRNDGEDSYRTQVTFFFPLDLSYRKVSTLQNQRSQRSWRLA
CESASSTEVSGALKSTSCSINHPIFPENSEVTFNITFDVDSKASLGNKLLLK
ANVTSENNMPRTNKTEFQLELPVKYAVYMVVTSHGVSTKYLNFTASENT
SRVMQHQYQVSNLGQRSLPISLVFLVPVRLNQTVIWDRPQVTFSENLSST
CHTKERLPSHSDFLAELRKAPVVNCSIAVCQRIQCDIPFFGIQEEFNATLK
GNLSFDWYIKTSHNHLLIVSTAEILFNDSVFTLLPGQGAFVRSQTETKVEP
FEVPNPLPLIVGSSVGGLLLLALITAALYKLGFFKRQYKDMMSEGGPPGAE
PQ (SEQ ID NO: 1)

FIG. 20

MNLQPIFWIGLISSVCCVFAQTDENRCLKANAKSCGECIQAGPNCGWCT
NSTFLQEGMPTSARCDDLEALKKKGCPPDDIENPRGSKDIKKNKNVTNR
SKGTAEKLKPEDIHQIQPQQLVLRLRSGEPQTFTLKFKRAEDYPIDLYYLM
DLSYSMKDDLENVKSLGTDLMNEMRRITSDFRIGFGSFVEKTVMPYISTT
PAKLRNPCTSEQNCTTPFSYKNVLSLTNKGEVFNELVGKQRISGNLDSPE
GGFDAIMQVAVCGSLIGWRNVTRLLVFSTDAGFHFAGDGKLGGIVLPND
GQCHLENNMYTMSHYYDYPSIAHLVQKLSENNIQTIFAVTEEFQPVYKEL
KNLIPKSAVGTLSANSSNVIQLIIDAYNSLSSEVILENGKLSEGVTISYKSYC
KNGVNGTGENGRKCSNISIGDEVQFEISITSNKCPKKDSDSFKIRPLGFTE
EVEVILQYICECECQSEGIPESPKCHEGNGTFECGACRCNEGRVGRHCE
CSTDEVNSEDMDAYCRKENSSEICSNNGECVCGQCVCRKRDNTNEIYS
GKFCECDNFCDRSNGLICGGNGVCKCRVCECNPNYTGSACDCSLDTS
TCEASNGQICNGRGICECGVCKCTDPKFQGQTCEMCQTCLGVCAEHKE
CVQCRAFNKGEKKDTCTQECSYFNITKVESRDKLPQPVQPDVSHCKEK
DVDDCWFYFTYSVNGNNEVMVHVVENPECPTGPDIIPIVAGVVAGIVLIGL
ALLLIWKLLMIIHDRREFAKFEKEKMNAKWDTGENPIYKSAVTTVVNPKYE
GK (SEQ ID NO: 2)

FIG. 21A

EVQLQQSGAELVKPGASVKLSCTASGFNIKDTYVHWVKQRPEQGLEWIG
RIDPANGYTKYDPKFQGKATITADTSSNTAYLQLSSLTSEDTAVYYCVRPL
YDYYAMDYWGQGTSVTVSSAKTTAPSVYPLAPVCGDTTGSSVTLGCLVK
GYFPEPVTLTWNSGSLSSGVHTFPAVLQSDLYTLSSSVTVTSSTWPSQSI
TCNVAHPASSTKVDKKIEPRPKSCDKTHTCPPCPAPELLGGPSVFLFPPK
PKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSL
SPGK (SEQ ID NO: 3)

FIG. 21B

DILMTQSPSSMSVSLGDTVSITCHASQGISSNIGWLQQKPGKSFMGLIYY
GTNLVDGVPSRFSGSGSGADYSLTISSLDSEDFADYYCVQYAQLPYTFG
GGTKLEIKRADAAPTVSIFPPSSEQLTSGGASVVCFLNNFYPKDINVKWKI
DGSERQNGVLNSWTDQDSKDSTYSMSSTLTLTKDEYERHNSYTCEATH
KTSTSPIVKSFNRNEC (SEQ ID NO: 4)

FIG. 21C

EVQLQQSGAELVKPGASVKLSCTASGFNIKDTYVHWVKQRPEQGLEWIG
RIDPANGYTKYDPKFQGKATITADTSSNTAYLQLSSLTSEDTAVYYCVRPL
YDYYAMDYWGQGTSVTVSSAKTTAPSVYPLAPVCGDTTGSSVTLGCLVK
GYFPEPVTLTWNSGSLSSGVHTFPAVLQSDLYTLSSSVTVTSSTWPSQSI
TCNVAHPASSTKVDKKIEPRPKSCDKTHTCPPCPAPELLGGPSVFLFPPK
PKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSL
SPGK (SEQ ID NO: 5)

FIG. 21D

DILMTQSPSSMSVSLGDTVSITCHASQGISSNIGWLQQKPGKSFMGLIYY
GTNLVDGVPSRFSGSGSGADYSLTISSLDSEDFADYYCVQYAQLPYTFG
GGTKLEIKRADAAPTVSIFPPSSEQLTSGGASVVCFLNNFYPKDINVKWKI
DGSERQNGVLNSWTDQDSKDSTYSMSSTLTLTKDEYERHNSYTCEATH
KTSTSPIVKSFNRNEC (SEQ ID NO: 6)

FIG. 22 ggcgaattcaccatggaggcctatcttgtggtcttaattgccattgctggcatagctcattccaatgaacac
aacctgaggtgcccgcagaatggaacagaaatgcccggtttcaacgactcgattaggcttcaattttttag
caatgcacaatggttacagatcaaaacttgcgctaggtcacatcagcataactgaagaatccgaaagt
gacgatgatgacgatttcggttttttacccgatttcgctccaagggcatcgaaaatgagatatctggaatat
gactgtgaagctgaaaaagcgcctacatgtcggctagaaattgctcggacagttcttctccaccagag
ggctacgatgaaaacaagtatattttcgaaaactcaaacaatatcagtgaagctgctctgaaggccatg
atctcgtgggcaaaagaggctttcaacctaataaaacaaagaaggagaaggagttctgtaccggt
cgaaccacgacatatcaaacttcgctaatctggcttgggacgcgcgtgaaaagtttggttgcgcagttgtt
aactgcccttgggagaaatcgatgatgaaccaaccatgatggagaaacctatgcaacaaccatcc
atgtagtctgccactacccgaaaataaacaaaactgaaggacagccgatttacaaggtagggacacc
atgcgacgattgcagtgaatacacaaaaaaagcagacaataccacgtctgcggatccggtgtgtattc
cggatgacggagtctgctttattggctcgaaagccgattacgatagcaaggagttttatcgattccgaga
gttatgaataagtcgagacgtataaagaagccaaggcaacgtaagcgagaatttc
(SEQ ID NO: 7)

FIG. 23

| TABLE 1 | | | | |
|---|---|---|---|---|
| Accession Number | Gene | Sense (5'-3') | Antisense (3'-5') | Amplicon (bp) |
| NM_001101 | β-actin | ATGACTTAGTTGCGTTACAC (SEQ ID NO: 9) | AATAAAGCCATGCCAATCTC (SEQ ID NO: 10) | 79 |
| NM_000632 | CD11b | TCGGCGGATGAAGGAGTTTG (SEQ ID NO: 11) | TCTTGGGTTAGGGTTGTTCTGG (SEQ ID NO: 12) | 139 |
| NM_002210 | Integrin αV | GACTCCTGCTACCTCTGT (SEQ ID NO: 13) | GCGAAGCCGAAGTAACTT (SEQ ID NO: 14) | 91 |
| NM_002211 | Integrin β1 | GACTTGAGACAGGATGGTTAC (SEQ ID NO: 15) | TGATTTCAATAGTCCAGGAAGAA (SEQ ID NO: 16) | 82 |
| NM_000250 | MPO | GCGTGTCCGAGCCTCTGA (SEQ ID NO: 17) | TCCCACCAAAACCGATCACCAT (SEQ ID NO: 18) | 106 |

COMPOSITIONS AND METHODS TO TREAT SOLID TUMORS

CROSS REFERENCE TO RELATED APPLICATION

This is a division of co-pending U.S. application Ser. No. 15/338,092, filed Oct. 28, 2016, which claims the benefit of the earlier filing date of U.S. Provisional Patent Application No. 62/248,144 filed on Oct. 29, 2015, and of U.S. Provisional Patent Application No. 62/332,397 filed on May 5, 2016, each of which is incorporated herein by reference in their entirety as if fully set forth herein.

FIELD OF THE DISCLOSURE

The present disclosure provides compositions and methods to treat solid tumors. The compositions and methods utilize anti-CD11b antibodies, anti-CD18 antibodies, anti-myeloperoxidase (MPO) antibodies, anti-integrin αV antibodies, anti-integrin β1 antibodies, Abciximab, neutrophil inhibitory factor (NIF) protein, and/or combinations thereof, as well as other compounds disclosed herein.

BACKGROUND OF THE DISCLOSURE

A "tumor" is a swelling or lesion formed by the growth and division of tumor cells. "Tumor cells" are abnormal cells that divide in an uncontrolled manner and generally continue to divide after the stimuli that initiated growth and division ceases.

Tumors usually show partial or complete lack of structural organization and functional coordination with the normal tissue, and usually form a distinct mass of tissue, which may be either benign, pre-malignant, or malignant. For example, fibromas, also known as fibroid tumors or fibroids, are composed of fibrous or connective tissue and are usually benign tumors. Despite being benign, such tumors often require therapeutic intervention.

Cancer (medical term: malignant neoplasm) refers to a class of diseases in which a group of cells display uncontrolled growth (division beyond the normal limits), invasion (intrusion on and destruction of adjacent tissues), and sometimes metastasis. "Metastasis" refers to the spread of cancer cells from their original site of proliferation to another part of the body. For solid tumors, the formation of metastasis is a very complex process and depends on detachment of malignant cells from the primary tumor, invasion of the extracellular matrix, penetration of the endothelial basement membranes to enter the body cavity and vessels, and then, after being transported by the blood or lymph, infiltration of target organs. Finally, the growth of a new tumor, i.e. a secondary tumor or metastatic tumor, at the target site depends on angiogenesis. Tumor metastasis often occurs even after the removal of the primary tumor because tumor cells (including cancer stem cells) or components may remain and develop metastatic potential.

Cancerous solid tumors can be found, for example, in the bone, bladder, brain, breast, colon, esophagus, gastrointestinal tract, genito-urinary tract, kidney, liver, lung, nervous system, ovary, pancreas, prostate, retina, skin, stomach, testicles, and/or uterus.

Taking ovarian cancer as an example, this type of cancer is currently regarded as one of the most common cancer types among women. In 2012 alone, the number of new cases of ovarian cancer stood at 239,000, constituting 1.7% of all cancer cases worldwide, according to World Cancer Research Fund International.

Ovarian cancer is rarely diagnosed at its early stages, making the treatment of this cancer at an advanced stage difficult. Chemotherapy for ovarian cancer is most often a combination of 2 or more drugs, given IV every 3- to 4-weeks. Giving combinations of drugs rather than just one drug alone seems to be more effective in the initial treatment of ovarian cancer. The standard approach is the combination of a platinum compound, such as cisplatin or carboplatin, and a taxane, such as paclitaxel (Taxol®, Bristol-Myers Squibb, New York N.Y.) or docetaxel (commercially available as Taxotere®, Aventis Pharma, Antony, France). However, the use of chemotherapeutic agents across all cancer types suffers from two major limitations. First, chemotherapeutic agents are not specific for cancer cells and particularly at high doses, they are toxic to normal rapidly dividing cells. Second, with time and repeated use, cancer cells develop resistance to chemotherapeutic agents thereby providing no further benefit to the patient. Furthermore, as the survival rate among women suffering from ovarian cancer is poor, efforts are afoot to develop new medications and therapies for the effective treatment of this disease.

SUMMARY OF THE DISCLOSURE

The present disclosure advances the treatment of solid tumors, including ovarian cancer solid tumors, by utilizing anti-CD11b antibodies, anti-CD18 antibodies, anti-myeloperoxidase (MPO) antibodies, anti-integrin αV antibodies, anti-integrin β1 antibodies, Abciximab and/or neutrophil inhibitory factor (NIF) protein. Other compounds disclosed herein may also be used.

Use of the described compounds has been shown to have anti-cancer effects in numerous cancer models, including in chemosensitive cancer cells, chemoresistant cancer cells, and cancer stem cells. Thus use of the compounds are broadly effective against varied cancer cell types. In addition, the compounds can be used in combination with each other and in combination with chemotherapeutic agents to provide effective therapeutic treatments. Use in combination with chemotherapeutic agents may allow lowering the dose of chemotherapeutic agents.

BRIEF DESCRIPTION OF THE FIGURES

(FIG. 1A) Anti-cancer effects of Abciximab in sensitive EOC cell lines (A2780, MDAH-2774, SKOV-3, OV90, TOV21G, OV112D, OV433, and HTB-161) and their Taxotere or Cisplatin resistant counterparts, human macrophages, and other cancer cell lines including colon (HTB-37), endometrial (CRL-1671), lung (CCL-257), prostate (CRL-1740), bladder (HTB-4), and hepatocellular (HB-8065) cancers, in vitro. (FIG. 1B) The combined effect of Abciximab alone or in combination with Cisplatin in both sensitive A2780 and their (FIG. 1C) Cisplatin resistant counterpart in vitro. (FIG. 1D) The synergistic effect of Abciximab and Cisplatin in both sensitive A2780 and their Cisplatin resistant counterpart in vitro, with CI<1 indicating synergism of the combined drugs. (FIG. 1E) Anti-cancer effects of NIF in both sensitive A2780 and their Cisplatin resistant counterpart in vitro.

(FIG. 3A) A2780 chemosensitive and (FIG. 3B) cisplatin resistant EOC cells were treated with or without integrin αV and integrin β1 antibody alone or in combination and viability was assessed using the TACS MTT Cell Proliferation Assay. (FIG. 3C) A2780 chemosensitive and (FIG. 3D) cisplatin resistant EOC cells were treated with or without a combination of integrin αV and integrin β1 antibody with or without Cisplatin and viability was assessed using the TACS MTT Cell Proliferation Assay while synergism (FIG. 3E) was assessed with the Compusyn software with CI<1 indicating a synergistic effect of the antibodies and Cisplatin.

(FIG. 7A) CD11b and (FIG. 7B) MPO mRNA levels were determined in both HOSEpiC and EOC cell lines.

(FIG. 10A) There was a significant increase in caspase-3 activity in both EOC cell lines, suggesting an increase in apoptosis. (FIG. 10B) There was an increase in the degree of fluorescence in CD11b antibody treated EOC cells, which indicates an increase in fragmented DNA and apoptosis.

(FIG. 15A) Anti-cancer effects of CD11b antibody in sensitive EOC cell lines (A2780, MDAH-2774, SKOV-3, OV90, TOV21G, OV112D, OV433, and HTB-161) and their Taxotere or Cisplatin resistant counterparts, non-cancer cells (human macrophages (EL1) and HOSEpiC), and other cancer cell lines including colon (HTB-37), endometrial (CRL-1671), lung (CCL-257), prostate (CRL-1740), bladder (HTB-4), and hepatocellular (HB-8065), in vitro. (FIG. 15B) The combined effect of CD11b antibody in combination with Cisplatin in both sensitive A2780 and their (FIG. 15C) Cisplatin resistant counterpart in vitro. (FIG. 15D) The synergistic effect of CD11b antibody and Cisplatin in both sensitive A2780 and their Cisplatin resistant counterpart in vitro, with CI<1 indicating synergism of the combined drugs. (FIG. 1F) Anti-cancer effects of NIF in both sensitive A2780 and their Cisplatin resistant counterpart in vitro.

(FIG. 17A) Sensitive and cisplatin resistant MDAH-2774 and SKOV-3 as well as cancer stem cells derived from SKOV-3 were treated with increasing doses of MPO antibody and viability was assessed by the TACS MTT Cell Proliferation Assay. (FIG. 17B) Sensitive and cisplatin resistant A2780 EOC cells as well as human macrophage cells were treated with MPO antibody and viability was assessed by the TACS MTT Cell Proliferation Assay. (FIG. 17C) SKOV-3 sensitive and (FIG. 17D) SKOV-3 Cisplatin resistant EOC cells were treated with a combination of MPO antibody and cisplatin and viability was assessed with the FIG. 18. Real-time RT-PCR analysis of TLR4 in sensitive and chemoresistant EOC cells. The commercial cisplatin chemoresistant A2780 EOC cell line (1.0 µM), as well as derived Taxotere® (0.3 µM) or cisplatin (1.5 µM) resistant MDAH-2774 and SKOV-3 EOC cell lines and their chemosensitive counterparts were utilized to determine chemoresistant as compared to their chemosensitive counterparts.

FIG. 19. Exemplary CD11b sequence (GenBank: AH004143.2; SEQ ID NO: 1).

FIG. 20. Exemplary CD18 sequence (GenBank: ADS87820.1; SEQ ID NO: 2).

FIGS. 21A-21D. Exemplary Abciximab sequences including its heavy chain 1 (FIG. 25A; SEQ ID NO: 3); light chain 1 (FIG. 25B; SEQ ID NO: 4); heavy chain 2 (FIG. 25C; SEQ ID NO: 5); and light chain 2 (FIG. 25D; SEQ ID NO: 6).

FIG. 22. Exemplary nucleotide sequence encoding Neutrophil inhibitory factor (NIF; SEQ ID NO: 7).

FIG. 23. Table 1. Oligonucleotide primers (SEQ ID NOs: 9-18) described in Example 2.

REFERENCE TO SEQUENCE LISTING

Figure 1A:
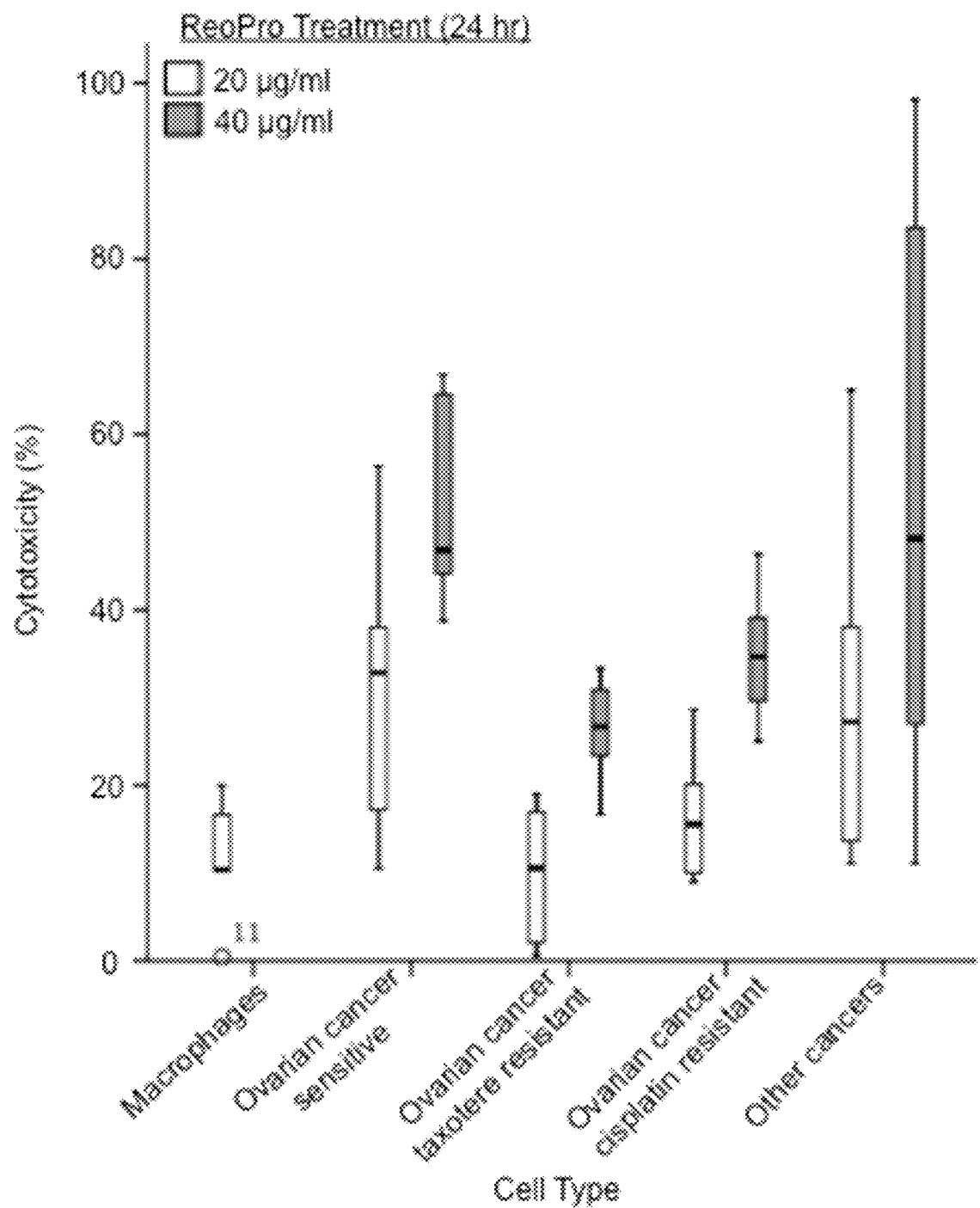
FIGS. 1A-1E. Anti-cancer effects of Abciximab and NIF.

The nucleic acid sequences described herein are shown using standard letter abbreviations for nucleotide bases, as defined in 37 C.F.R. § 1.822. A computer readable text file, entitled "Sequence Listing.txt" created on or about May 18, 2019, with a file size of 40 KB, contains the sequence listing for this application and is hereby incorporated by reference in its entirety.

DETAILED DESCRIPTION

A "tumor" is a swelling or lesion formed by the growth and division of tumor cells. "Tumor cells" are abnormal cells that divide in an uncontrolled manner and generally continue to divide after the stimuli that initiated growth and division ceases.

Tumors usually show partial or complete lack of structural organization and functional coordination with the normal tissue, and usually form a distinct mass of tissue, which may be either benign, pre-malignant, or malignant.

Fibrosis is the pathological state of excess deposition of fibrous tissue, as well as the process of connective tissue deposition in healing. Fibroid tissue solid tumors (e.g., fibromas, fibroids, fibroid tumors) are the result of formations of excess fibrous connective tissue in an organ or tissue in a reparative or reactive process. Fibroid tissue solid tumors are usually benign. Even though benign, these tumors can cause a number of adverse side effects, such as pain and/or damage to the architecture and function of the underlying affected organ or tissue. Examples of conditions that can be associated with fibroid tissue solid tumors include some forms of adhesive capsulitis, arterial fibrosis, arthrofibrosis, Crohn's disease, cirrhosis, cystic fibrosis, endomyocardial fibrosis, fibrous cysts, idiopathic pulmonary fibrosis, keloids, mediastinal fibrosis, myelofibrosis, nephrogenic systemic fibrosis, Peyronie's disease, pulmonary fibrosis, progressive massive fibrosis, retroperitoneal fibrosis, scleroderma/systemic sclerosis, uterine fibroids (uterine leiomyomas), and other precancerous fibromas. Fibrosarcoma is a malignant solid tumor derived from fibrous connective tissues.

With respect to uterine fibroids particularly, The National Uterine Fibroids Foundation estimates that as many as 80% of all women in the United States have uterine fibroids, and one in four of these women have symptoms severe enough to require treatment. The current standards of treatment are hormone therapy, oral contraceptives, gonadotropin releasing hormone agonists, uterine artery embolization and myomectomy.

Cancer (medical term: malignant neoplasm) refers to a class of diseases in which a group of cells display uncontrolled growth (division beyond the normal limits), invasion (intrusion on and destruction of adjacent tissues), and sometimes metastasis. "Metastasis" refers to the spread of cancer cells from their original site of proliferation to another part of the body. For solid tumors, the formation of metastasis is a very complex process and depends on detachment of malignant cells from the primary tumor, invasion of the extracellular matrix, penetration of the endothelial basement membranes to enter the body cavity and vessels, and then, after being transported by the blood or lymph, infiltration of target organs. Finally, the growth of a new tumor, i.e. a secondary tumor or metastatic tumor, at the target site depends on angiogenesis. Tumor metastasis often occurs even after the removal of the primary tumor because tumor cells (including cancer stem cells) or components may remain and develop metastatic potential.

Cancerous solid tumors can be found, for example, in the bone, bladder, brain, breast, colon, esophagus, gastrointestinal tract, genito-urinary tract, kidney, liver, lung, nervous system, ovary, pancreas, prostate, retina, skin, stomach, testicles, and/or uterus.

Taking ovarian cancer as an example, this type of cancer is currently regarded as one of the most common cancer types among women. In 2012 alone, the number of new cases of ovarian cancer stood at 239,000, constituting 1.7% of all cancer cases worldwide, according to World Cancer Research Fund International.

Ovarian cancer is rarely diagnosed at its early stages, making the treatment of this cancer at an advanced stage difficult. Chemotherapy for ovarian cancer is most often a combination of 2 or more drugs, given IV every 3- to 4-weeks. Giving combinations of drugs rather than just one drug alone seems to be more effective in the initial treatment of ovarian cancer. The standard approach is the combination of a platinum compound, such as cisplatin or carboplatin, and a taxane, such as paclitaxel (Taxol®, Bristol-Myers Squibb, New York N.Y.) or docetaxel (commercially available as Taxotere®, Aventis Pharma, Antony, France). Use of chemotherapeutic agents across all cancer types, however, suffers from two major limitations. First, chemotherapeutic agents are not specific for cancer cells and particularly at high doses, they are toxic to normal rapidly dividing cells.

Second, with time and repeated use, cancer cells develop resistance to chemotherapeutic agents thereby providing no further benefit to the patient.

As the survival rate among women suffering from ovarian cancer is poor, efforts are afoot to develop new medications and therapies for the effective treatment of this disease.

The present disclosure advances the treatment of solid tumors, including ovarian cancer solid tumors, by utilizing anti-CD11b antibodies, anti-CD18 antibodies, anti-MPO antibodies, anti-integrin αV antibodies, anti-integrin β1 antibodies, Abciximab and/or neutrophil inhibitory factor (NIF) protein. Other compounds disclosed herein may also be used.

Use of the described compounds has been shown to have anti-cancer effects in numerous cancer models, including in chemosensitive cancer cells, chemoresistant cancer cells, and cancer stem cells. Thus use of the compounds are broadly effective against varied cancer cell types. In addition, the compounds can be used in combination with each other and in combination with chemotherapeutic agents to provide effective therapeutic treatments.

CD11b (Mac-1α; integrin αM chain) is part of the CD11b/CD18 heterodimer (Mac-1α, Mβ2 integrin), also known as the C3 complement receptor. It functions as a receptor for complement (C3bi), fibrinogen, or clotting factor X. In humans, CD11b is strongly expressed on myeloid cells and weakly expressed on NK cells and some activated lymphocytes as well as on microglia in the brain. In mice, the CD11b antigen is expressed on monocytes/macrophages and microglia. To a lower extent it is expressed on granulocytes, NK cells, CD5+B-1 cells, and subsets of dendritic cells. As disclosed herein, CD11b is also expressed on solid tumor cells and targeting it leads to anti-tumor effects. Exemplary relevant sequences for CD11b can be found at Accession Nos. NP_001139280.1, NP_000623.2, XP_011544153.1, XP_011544152.1, XP_006721108.1, AAH99660.1, and AH004143.2. In particular embodiments, CD11b refers to SEQ ID NO: 1 (FIG. 23).

CD18 is the integrin β chain β2. In humans, a lack of CD18 causes Leukocyte Adhesion Deficiency, a disease defined by a lack of leukocyte extravasation from blood into tissues. Exemplary relevant sequences for CD18 can be found at Accession Nos. AAE18916.1, ADS63144.1, AJL09630.1, AAB21332.1, AAB21402.1, AAB21403.1, and AAB21404.1. In particular embodiments, CD18 refers to SEQ ID NO: 2 (FIG. 24).

MPO is most abundantly expressed in neutrophil granulocytes (a subtype of white blood cells), and produces hypohalous acids to carry out their antimicrobial activity. It is a lysosomal protein stored in azurophilic granules of the neutrophil and released into the extracellular space during degranulation. MPO has a heme pigment, which causes its green color in secretions rich in neutrophils, such as pus and some forms of mucus. MPO is also known to play a prominent role in fibrosis.

Integrins are integral cell-surface transmembrane receptor proteins composed of an α chain and a β chain. A given α or β chain may combine with multiple partners resulting in different integrins. For example, β2 combines with the αL chain to form the integrin LFA-1, and combines with the α M chain to form the integrin Mac-1. Integrins are involved in cell adhesion and recognition in various processes including embryogenesis, hemostasis, tissue repair, immune response, and metastatic diffusion of tumor cells.

In humans, the integrin αV protein (CD51) is encoded by the ITGAV gene. CD51 includes disulfide-linked heavy and light chains. CD51 combines with other β chains to form different integrins. CD51 associates with β1, β3, β5, β6, and β8 chains to form receptors for vitronectin, fibrinogen, fibronectin, osteopontin, cytotactin, laminin, matrix metalloproteinase-2, osteomodulin, prothrombin, thrombospondin, and Von Willebrand Factor. Generally, these receptors recognize the R-G-D sequence in various ligands. Exemplary mammalian sequences encoding integrin αV can be found at Accession Nos. P06756.2, EDL27275.1, and NP_001290501.1.

Integrin β1 (CD29) is the most abundantly expressed β integrin and associates with 10 different integrin α subunits. In humans, CD29 is encoded by the ITGB1 gene. CD29 exists in different isoforms via alternative splicing. There are six alternatively spliced variants for the gene which encodes 5 proteins with alternate C-termini.

Like other integrins, CD29 has a large extracellular domain and a short intracellular domain. The cytoplasmic domain of integrin β1 binds to the actin cytoskeleton. Accordingly, integrins link the actin cytoskeleton with the extracellular matrix and transmit signals bidirectionally between the extracellular matrix and cytoplasmic domains. β-integrins target integrins to the appropriate subcellular locations, which in adhesive cells is mainly the focal adhesions.

There are three novel isoforms of integrin β1: β1B, β1C, and β1D. The β1B isoform inhibits cell adhesion, while the β1C isoform inhibits DNA synthesis in the G1 phase of cell cycle. The third isoform, β1 D, is a striated muscle-specific isoform. Exemplary mammalian sequences encoding CD29 can be found at Accession Nos. P05556, EDL11832.1, and NP_058718.2.

CD44 is a receptor for hyaluronic acid and can also interact with other ligands, such as osteopontin, collagens, and matrix metalloproteinases (MMPs). CD44 is a multistructural and multifunctional cell surface molecule involved in cell proliferation, cell differentiation, cell migration, angiogenesis, presentation of cytokines, chemokines, and growth factors to the corresponding receptors, and docking of proteases at the cell membrane, as well as in signaling for cell survival. All these biological properties are essential to the physiological activities of normal cells, but they are also associated with the pathologic activities of cancer cells.

CD117 is a cytokine receptor expressed on the surface of hematopoietic stem cells as well as other cell types. Altered forms of this receptor may be associated with some types of cancer. CD117 is a receptor tyrosine kinase type Ill, which binds to stem cell factor (a substance that causes certain types of cells to grow), also known as "steel factor" or "c-kit ligand". When this receptor binds to stem cell factor (SCF) it forms a dimer that activates its intrinsic tyrosine kinase activity that in turn phosphorylates and activates signal transduction molecules that propagate the signal in the cell. Signaling through CD117 μlays a role in cell survival, proliferation, and differentiation.

Before the current disclosure, it was not known that anti-CD11b and/or anti-CD18 (CD11b/CD18) compounds would lead to solid tumor cell death. Anti-CD11b and/or anti-CD18 compounds inhibit, suppress and/or eliminate the natural physiological activities of their target, such as CD11b/CD18 in a solid tumor cell, such that an anti-solid tumor effect (described below) is achieved. In particular embodiments, active agent(s) competitively bind to and/or block CD11b/CD18. Because CD11b forms a heterodimer with CD18, targeting CD11b or CD18 can block the heterodimer as well as the individual proteins.

Moreover, MPO binds to CD11b and is an important mechanism in development of ovarian cancer as well as chemoresistance. Reducing or preventing this binding using an anti-MPO and/or CD11b antagonist (e.g., antibody) causes growth arrest and/or apoptosis. This binding reduction or prevention can augment current therapies to the cancer and bypass mechanisms of resistance.

The current disclosure also includes use of anti-Integrin αV or anti-Integrin β1 (collectively Integrin αVβ1) alone or in combination with anti-CD11b/CD18 and/or anti-MPO compounds. Anti-αV or anti-β1 compounds inhibit, suppress and/or eliminate the natural physiological activities of Integrin αV and/or β1 in a solid tumor cell, such that an anti-solid tumor effect (described below) is achieved. In particular embodiments, active agent(s) competitively bind to and/or block Integrin αVβ1. Because Integrin αV forms a heterodimer with Integrin β1, targeting Integrin αV or β1 can block the heterodimer as well as the individual proteins.

Any compound capable of inhibiting, suppressing and/or eliminating CD11b/CD18, MPO, and/or Integrin αVβ1 activity, among other compounds disclosed herein, can be used with the compositions and methods disclosed herein. Such compounds are referred to as active agent(s). Active agent(s) can include, for example, proteins, peptides, antibodies, small molecules, fusion proteins, and conjugates, as well as physiologically acceptable salts, prodrugs, variants, modifications, D-substituted analogs, homologues and allelic variants thereof.

Particularly useful active agent(s) utilize anti-CD11b antibodies (e.g., rat anti-mouse CD11b available from BD Bioscience, #554980; mouse anti-human CD11b ICRF44, available from Affymetrix; and mouse and human reactive anti-CD11b M1/10, available from Abcam), anti-CD18 antibodies (e.g., mouse anti-human CD18 TS1/18, available from BioLegend and mouse anti-human CD18 MEM/148, available from Abcam), anti-MPO antibodies (e.g., mouse anti-human MPO available from ThermoFisher Scientific, #MA1-34067, #GM4192, #MA5-15480), anti-integrin αV antibodies (e.g., mouse anti-human integrin αV available from Santa Cruz Biotechnology #SC-9969 and mouse anti-human integrin αV 272-17E6, available from Abcam), anti-integrin β1 antibodies (e.g., mouse anti-human integrin β1 available from Santa Cruz Biotechnology #SC-37443 and rabbit anti-human integrin β1 EP2041Y, available from Abcam), Abciximab, NIF protein, human cathelicidin peptide LL-37 (LL-37), Clopidogrel (Plavix®, Sanofi-Aventis, Paris, France), Cilostazol (Pletal®, Otsuka Pharmaceutical, Osaka, Japan), compounds of Formula I, Intetumumab, Abituzumab, or a combination thereof although other compounds that inhibit, suppress and/or eliminate CD11b/CD18, MPO, and/or Integrin αVβ1 can also be used.

Abciximab (previously known as c7E3 Fab, Accession No. DB00054 (BIOD00041, BTD00041)) is a glycoprotein IIb/IIIa receptor antagonist currently distributed under the trade name ReoPro® (Eli Lilly & Co., Indianapolis, Ind.). Abciximab is currently used as a platelet aggregation inhibitor mainly used during and after coronary artery procedures like angioplasty to prevent platelets from sticking together and causing thrombus (blood clot) formation within the coronary artery. Abciximab is indicated for use in individuals undergoing percutaneous coronary intervention (angioplasty with or without stent placement).

Abciximab has the protein chemical formula $C_{6462}H_{9964}N_{1690}O_{2049}S_{48}$ and a weight of 145651 D. Exemplary Abciximab sequences include heavy chain 1 (FIG. 25A; SEQ ID NO: 3); light chain 1 (FIG. 25B; SEQ ID NO: 4); heavy chain 2 (FIG. 25C; SEQ ID NO: 5); and light chain 2 (FIG. 25D; SEQ ID NO: 6).

NIF is a 41-kDa CD11/CD18 P(2) integrin-binding protein isolated from the canine hookworm (*Ancylostoma caninum*). NIF includes 257 amino acids and contains seven glycosylation sites. It blocks PMN adhesion in a concentration-dependent manner with, in particular embodiments, a complete blockade occurring at 10 nM NIF. NIF can effectively inhibit neutrophil activities including adhesion to endothelial cells, release of hydrogen peroxide and superoxide ions, as well as chemotaxis, aggregation and phagocytosis of neutrophil, etc (Moyle et al: J Biol chem 1994, 269(13):10008-10015). Nucleic acid sequences encoding NIF can be found at, for example, Accession Nos. L27427.1, DI138516.1, DI132333.1, DI127964.1, DD041939.1, DD041938.1, and DD041937.1. FIG. 26 provides an exemplary encoding sequence (SEQ ID NO: 7).

Human cathelicidin peptide LL-37 (LL-37) includes the C-terminal 37 amino acids of human cathelicidin (e.g., LLGDFFRKSKEKIGKEFKRIVQRIKDFLRNLVPRTES (SEQ ID NO: 8)). LL-37 was originally referred to as FALL39, named for the first 4 N-terminal amino acids of this domain and the total number of residues (i.e., 39). LL-37 is a peptide predicted to contain an amphipathic α helix and lacks cysteine, making it different from all other previously isolated human peptide antibiotics of the defensin family, each of which contain 3 disulfide bridges. Full length human cathelicidin includes the cathelin-like precursor protein and the C-terminal LL-37 peptide, thus including 170 amino acids.

Cathelicidins more generally are a family of endogenous antimicrobial peptides which form a part of the innate immunity that protects the host from infection (Eckmann, Gastroenterol. 2005; 21(2):147-51). Cathelicidin exists in human as LL-37 and in mice as mCRAMP (Gudmundsson et al., Eur J Biochem. 1996; 238(2):325-32; Gallo et al., J Biol Chem. 1997; 272(20):13088-93). Cathelicidin is secreted from the apical surface that is facing exterior environment such as intestine (Schauber et al., Eur J Gastroenterol Hepatol. 2006; 18(6):615-21) and salivary gland (Murakami et al., J Dent Res. 2002; 81(12):845-50) by epithelial cells (Schauber et al., Eur J Gastroenterol Hepatol. 2006; 18(6):615-21) and immune cells such as macrophages (Koon et al., Gastroenterology. 2011; 141(5):1852-63 e1-3).

Intetumumab, also known as CNTO 95, is the first fully human monoclonal antibody that recognizes all the members of the CD51 family of integrins. Intetumumab binds CD51 integrins with high affinity and specificity.

Abituzumab is a recombinant humanized monoclonal antibody for human CD51. It is used to inhibit CD51 expressed on CRPC cells, tumor vessels and osteoclasts involved in bone metastasis. Abituzumab is in phase II clinical trials for metastatic castration-resistant prostate cancer (CRPC).

Various polyclonal and monoclonal antibodies against CD29 are commercially available.

While exemplary protein and nucleic acid sequences are provided, one of ordinary skill in the art understands that additional supporting sequences may be found in publicly available databases. Protein and/or nucleic acid sequences for use in the compositions and methods disclosed herein also include proteins and/or nucleic acid sequences having at least 90% sequence identity to a protein or nucleic acid disclosed herein; at least 91% sequence identity to a protein or nucleic acid disclosed herein; at least 92% sequence identity to a protein or nucleic acid disclosed herein; at least 93% sequence identity to a protein or nucleic acid disclosed herein; at least 94% sequence identity to a protein or nucleic acid disclosed herein; at least 95% sequence identity to a protein or nucleic acid disclosed herein; at least 96% sequence identity to a protein or nucleic acid disclosed herein; at least 97% sequence identity to protein or nucleic acid disclosed herein; at least 98% sequence identity to a protein or nucleic acid disclosed herein; or at least 99% sequence identity to a protein or nucleic acid disclosed herein.

"% sequence identity" refers to a relationship between two or more sequences, as determined by comparing the sequences. In the art, "identity" also means the degree of sequence relatedness between sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215, 403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y.). Within the context of this disclosure it will be understood that where sequence analysis software is used for analysis, the results of the analysis are based on the "default values" of the program referenced. "Default values" mean any set of values or parameters which originally load with the software when first initialized.

Reference to proteins described herein also include variants, modifications, D-substituted analogs, homologues and allelic variants thereof. "Variants" of proteins disclosed herein include proteins having one or more amino acid additions, deletions, stop positions, or substitutions, as compared to a protein disclosed herein.

An amino acid substitution can be a conservative or a non-conservative substitution. Variants of proteins disclosed herein can include those having one or more conservative amino acid substitutions. A "conservative substitution" involves a substitution found in one of the following conservative substitutions groups: Group 1: alanine (Ala or A), glycine (Gly or G), Ser, Thr; Group 2: aspartic acid (Asp or D), Glu; Group 3: asparagine (Asn or N), glutamine (Gln or Q); Group 4: Arg, lysine (Lys or K), histidine (His or H); Group 5: lie, leucine (Leu or L), methionine (Met or M), valine (Val or V); and Group 6: Phe, Tyr, Trp.

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Substitutions can be made to improve the pharmacokinetic and/or pharmacodynamic (PK/PD) properties of a protein. For example, residues that are sensitive to degradation (e.g., Met) can be replaced or substituted with residues that are less sensitive to degradation (e.g., Nle). Substitution of the C-terminal acid with an amide can also impart stability. An anionic moiety substitution at the N-terminus can also increase protein stability.

Modifications, as used herein, include altering amino acid structures or attaching functional groups to amino acids to improve, for example, PK/PD properties. In particular embodiments, use of nonhydrolyzable phosphate substitutions can impart a stabilizing effect on the phosphate groups, and can provide stability against phosphatase enzymes. Organic or inorganic chemical entities can also be attached to proteins.

Non-limiting examples of appropriate chemical entities include L-p-phosphonomethyl-phenylalanine (Pmp) (OH2); D-Pmp(OH2); D-Pmp(OHEt); Pmp(Et2); D-Pmp(Et2); L-Tyr L-Tyr(PO3H2) (p-phospho-Tyrosine); L-Phe(p-NH2); L-Phe(p-CO2H); L-Aspartate; D-Aspartate; L-Glutamate; and D-Glutamate. Pmp can be substituted with (p-phosphatityl-phenylalanine) (Ppa); (p-Phosphono(difluoro-methyl)-Phenylalanine) (Pfp) or (p-Phosphono-methylketo-Phenylalanine) (Pkp). Exemplary chemical entities can be attached by way of a linker, such as an aminoethyl-oxyethyloxy-acetyl linker or by any other suitable means.

PEGylation provides another potential modification. PEGylation is a process by which polyethylene glycol (PEG) polymer chains are covalently conjugated to other molecules such as drugs or proteins. Several methods of PEGylating proteins have been reported in the literature. For example, N-hydroxy succinimide (NHS)-PEG was used to PEGylate the free amine groups of lysine residues and N-terminus of proteins; PEGs bearing aldehyde groups have been used to PEGylate the amino-termini of proteins in the presence of a reducing reagent; PEGs with maleimide functional groups have been used for selectively PEGylating the free thiol groups of cysteine residues in proteins; and site-specific PEGylation of acetyl-phenylalanine residues can be performed.

Covalent attachment of proteins to PEG has proven to be a useful method to increase the circulating half-lives of proteins in the body (Abuchowski, et al., Cancer Biochem. Biophys., 1984, 7:175-186; Hershfield, et al., N. Engl. J. Medicine, 1987, 316:589-596; and Meyers, et al., Clin. Pharmacol. Ther., 1991, 49:307-313). The attachment of PEG to proteins not only protects the molecules against enzymatic degradation, but also reduces their clearance rate from the body. The size of PEG attached to a protein has significant impact on the circulating half-life of the protein. The ability of PEGylation to decrease clearance is generally not a function of how many PEG groups are attached to the protein, but the overall molecular weight of the altered protein. PEGylation decreases the rate of clearance from the bloodstream by increasing the apparent molecular weight of the molecule. Up to a certain size, the rate of glomerular filtration of proteins is inversely proportional to the size of the protein. Usually the larger the PEG is, the longer the in vivo half-life of the attached protein is. In addition, PEGylation can also decrease protein aggregation (Suzuki et al., Biochem. Bioph. Acta vol. 788, pg. 248 (1984)), alter protein immunogenicity (Abuchowski et al.; J. Biol. Chem. vol. 252 μg. 3582 (1977)), and increase protein solubility as described, for example, in PCT Publication No. WO 92/16221).

Several sizes of PEGs are commercially available (Nektar Advanced PEGylation Catalog 2005-2006; and NOF DDS Catalogue Ver 7.1), which are suitable for producing proteins with targeted circulating half-lives. A variety of active PEGs have been used including mPEG succinimidyl succinate, mPEG succinimidyl carbonate, and PEG aldehydes, such as mPEG-propionaldehyde.

"D-substituted analogs" include proteins disclosed herein having one more L-amino acids substituted with one or more D-amino acids. The D-amino acid can be the same amino acid type as that found in the reference sequence or can be a different amino acid. Accordingly, D-analogs can also be variants.

Clopidogrel (marketed as Plavix® by Sanofi (Paris France)) and Cilostazol (marketed as Pletal) by Otsuka Pharmaceuticals Co. (Osaka, JP)) share a common mechanism of action with Abciximab. Thus, these compounds are also appropriate for use in the compositions and treatment methods disclosed herein. More particularly, Clopidogrel is an oral antiplatelet agent used to inhibit blood clots in various diseases such as coronary artery disease, peripheral vascular disease, cerebrovascular disease and to prevent myocardial infarction. It is an irreversible inhibitor of P2Y12 adenosine diphosphate receptor found on the membranes of platelet cells.

Clopidogrel has a molecular weight of 321.82 g/mol and a molecular formula of $C_{16}H_{16}ClNO_2S$. Clopidogrel has the following structural formula,

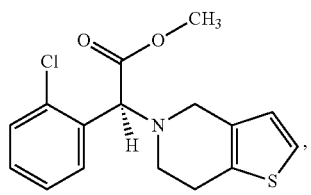 [SMILES: COC(=O)[C@H](c1ccccc1Cl)N1CCc2sccc2C1]

and the following IUPAC name: methyl (2S)-2-(2-chlorophenyl)-2-(6,7-dihydro-4H-thieno[3,2-c]pyridin-5-yl)acetate.

In particular embodiments, Cilostazol can be used in the compositions and methods disclosed herein. Cilostazol is a phosphodiesterase inhibitor with therapeutic focus on cyclic adenosine monophosphate (cAMP). Cilostazol inhibits platelet aggregation and is a direct arterial vasodilator. Cilostazol is used to treat intermittent claudication, a condition caused by narrowing of the arteries that supply the legs with blood. Cilostazol alleviates intermittent claudication by dilating the arteries to improve the flow of blood and oxygen to the legs and by inhibiting the action of phosphodiesterase Ill.

Cilostazol has a molecular weight of 369.46 g/mol and a molecular formula of $C_{20}H_{27}N_5O_2$. Cilostazol has the following structural formula,

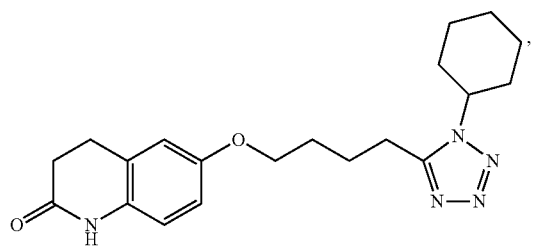 [SMILES: O=C1CCc2cc(OCCCCc3nnnn3C3CCCCC3)ccc2N1]

and the following IUPAC name, 6-[4-(1-cyclohexyl-1H-tetrazol-5-yl)butoxy]-3,4-dihydro-2(1H)-quinolinone.

In particular embodiments, a compound of formula (I) can be used in the compositions and methods disclosed herein. Formula (I) includes

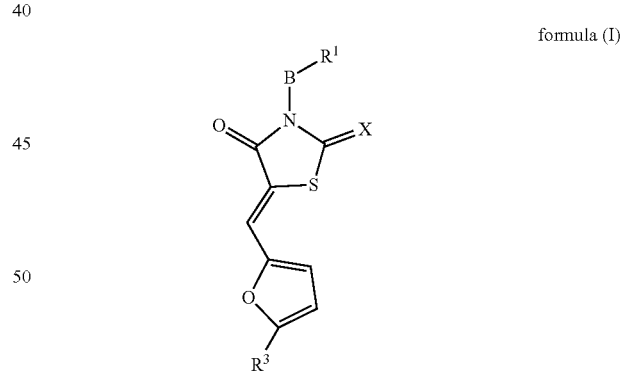

formula (I)

wherein:

B is absent and R1 is phenyl; or

B is methylene and R1 is phenyl or phenyl substituted with one fluoro;

N is nitrogen;

X is selected from the group including O and S; and

R3 is selected from the group including 4-carboxyphenyl and 3-carboxy-4-chlorophenyl. In embodiments, the compound is a substantially pure single Z conformer. In certain embodiments, the compound is

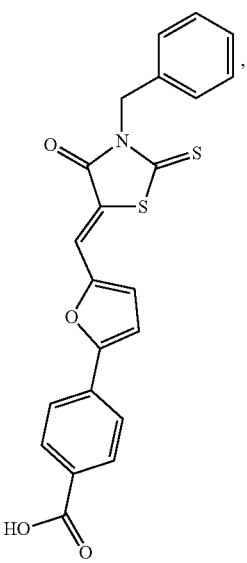

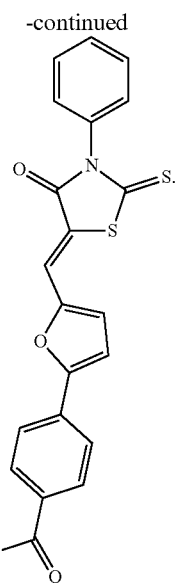

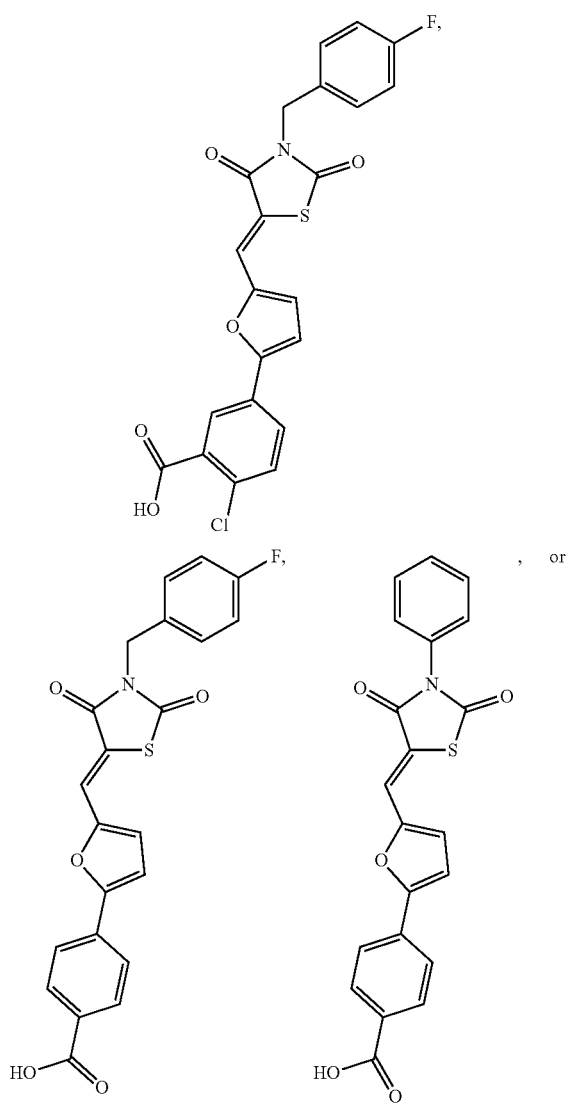

, or

Methods disclosed herein include treating subjects (humans, veterinary animals (dogs, cats, reptiles, birds, etc.), livestock (horses, cattle, goats, pigs, chickens, etc.), and research animals (monkeys, rats, mice, fish, etc.)) with active agent(s) disclosed herein. Subjects in need of a treatment (in need thereof) are subjects having a solid tumor, whether the solid tumor occurred naturally or by induction through a research protocol. Subjects in need thereof also include those who have had a solid tumor in the past.

Treating subjects includes delivering therapeutically effective amounts. Therapeutically effective amounts include those that provide effective amounts, prophylactic treatments, and/or therapeutic treatments.

An "effective amount" is the amount of active agent(s) or composition(s) necessary to result in a desired physiological change in a subject. Effective amounts are often administered for research purposes. Effective amounts disclosed herein have an anti-solid tumor effect.

A "prophylactic treatment" includes a treatment administered to a subject who does not display signs or symptoms of distant or metastatic solid tumors or chemoresistance, or displays only early signs or symptoms of distant or metastatic solid tumors or chemoresistance such that treatment is administered for the purpose of diminishing, preventing, or decreasing the risk of developing further distant or metastatic solid tumors or chemoresistance. Thus, a prophylactic treatment functions as a preventative treatment against the development of distant or metastatic solid tumors or chemoresistance further.

A "therapeutic treatment" includes a treatment administered to a subject who has one or more solid tumor(s) or who has had one or more solid tumor(s) and is administered to the subject for the purpose of providing an anti-solid tumor effect. Therapeutic treatments can be distinguished from effective amounts based on the presence or absence of a research component to the administration. As will be understood by one of ordinary skill in the art, however, in human clinical trials therapeutic treatments and effective amounts can overlap.

An anti-solid tumor effect means a decrease in solid tumor volume, a decrease in the number of solid tumor cells, a decrease in the number of solid tumors, slowed or inhibited growth of a solid tumor, induction of apoptosis in solid tumor cells, a decrease in solid tumor metastases and/or a delay in the development of chemoresistance. Solid tumor cells can include cancer cells, chemoresistant cells, cancer stem cells, and any other cells found within benign, pre-malignant or malignant tumors. Solid tumor cells can also include any tumor cells left behind after surgical removal or another treatment that may lead to a tumor or cancer recurrence if left untreated.

In particular embodiments, an anti-solid tumor effect can lead to an anti-cancer effect. An anti-cancer effect can be manifested by a decrease in cancer recurrence, an increase in time before cancer recurrence, an increase in life expectancy, an increase in life duration, or a decrease in various physiological symptoms associated with a solid tumor cancerous condition.

Solid tumors that can be treated with the compositions and methods disclosed herein include benign tumors, pre-malignant tumors, malignant tumors, and chemoresistant tumors. The compositions and methods disclosed herein can also be used to treat chemoresistant cancer cells and/or cancer stem cells whether part of or independent from a solid tumor at the time of treatment.

Benign tumors include fibroid tissue solid tumors, such as uterine fibroids.

Pre-malignant or malignant solid tumors include those found in subjects with acoustic neuroma, adenocarcinoma, astrocytoma, basal cell cancer, bile duct cancer, bladder cancer, brain cancer, breast cancer, bronchogenic cancer, central nervous system cancer, cervical cancer, chondrosarcoma, choriocarcinoma, colon cancer, craniopharyngioma, ependymoma, Ewing's tumor, fibrosarcoma, glandular cancer, glioma, hemangioblastoma, hepatocellular carcinoma, hepatoma, kidney cancer, leiomyosarcoma, liver cancer, liposarcoma, lung cancer, melanoma, medulloblastoma, medullary cancer, medullary thyroid cancer, menangioma, mesothelioma, myxosarcoma, neuroblastoma, oligodendroglioma, osteogenic sarcoma, ovarian cancer, papillary adenocarcinomas, papillary thyroid cancer, pancreatic cancer, pheochromocytomas papillary cancer, pineal cancer, prostate cancer, renal cell cancer, retinoblastoma, rhabdomyosarcoma, sarcoma, sebaceous gland cancer, seminoma, skin cancer, squamous cell cancer, sweat gland cancer, synovioma, testicular cancer, and/or Wilms' tumor. Solid tumors do not include cancers associated with blood or other liquid cancers.

Chemoresistant cancer cells are cancer cells that have become less susceptible to the therapeutic effects of a chemotherapeutic agent. Chemoresistance can be identified using in vitro assays. For example, the overexpression of Toll Like Receptor 4 (TLR-4) in human tumors correlates with chemoresistance and metastasis. Therefore, detecting overexpression of TLR-4 in a cancer cell after exposure to the chemotherapeutic agent indicates chemoresistance. Chemoresistance can also be identified by a reduction in the therapeutic effect of an administered treatment. In particular embodiments, therapeutically effective amounts kill chemoresistant cancer cells.

Cancer stem cells possess the characteristics associated with normal stem cells, such as self-renewal and differentiation. Thus, they have the ability to give rise to all cell types found in a particular cancer sample. Cancer stem cells may generate tumors through the stem cell processes of self-renewal and differentiation into multiple cell types. Such cells are hypothesized to persist in subjects as a distinct population and cause relapse and metastasis by giving rise to new tumors, even after successful initial treatment. In particular embodiments, therapeutically effective amounts kill cancer stem cells.

For administration, therapeutically effective amounts (also referred to herein as doses) can be initially estimated based on results from in vitro assays and/or animal model studies. Such information can be used to more accurately determine useful doses in subjects of interest. In vitro assays can assess cell growth as determined by MTT and colony formation assays. Cell counting as a golden standard can be performed routinely to determine cell doubling times and growth rates.

The actual dose amount administered to a particular subject can be determined by a physician, veterinarian, or researcher taking into account parameters such as physical, physiological and psychological factors including target, body weight, type of tumor, size of tumor, location of tumor, stage of cancer, type of cancer, previous or concurrent therapeutic interventions, idiopathy of the subject, and/or route of administration.

Exemplary doses can include 0.05 mg/kg to 5.0 mg/kg of the active agent(s). For certain indications, the total daily dose can be 0.05 mg/kg to 30.0 mg/kg active agent(s) administered to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day of administration forms of the active agent(s) using 60-minute oral, intravenous or other dosing. In one particular example, doses can be administered QD or BID to a subject with, e.g., total daily doses of 1.5 mg/kg, 3.0 mg/kg, or 4.0 mg/kg of a composition with up to 92-98% wt/v of the active agent(s).

Additional useful doses can often range from 0.1 to 5 µg/kg or from 0.5 to 1 µg/kg. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 pg/kg, 80 µg/kg, 85 µg/kg, 90 µg/kg, 95 µg/kg, 100 µg/kg, 150 µg/kg, 200 µg/kg, 250 µg/kg, 350 pg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

Particularly useful doses can include 0.25-5 mg/kg intravenous bolus followed by a continuous intravenous infusion of 0.125-2.5 µg/kg/min for 12 hours, per treatment.

Doses referred to herein can include one or more active agent(s) collectively or individually.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly).

One or more active agent(s) can be administered simultaneously or within a selected time window, such as within 10 minutes, 1 hour, 3 hour, 10 hour, 15 hour, 24 hour, or 48 hour time windows or when the complementary active agent(s) is within a clinically-relevant therapeutic window.

In particular embodiments, the active agent(s) can be used in conjunction with other cancer treatments such as a gonadotropin-releasing hormone agonist or antagonist (e.g., Lupron, Zoladex (Goserelin), Degarelix, Ozarelix, ABT-620 (Elagolix), TAK-385 (Relugolix), EP-100 or KLH-2109); a phosphoinositide 3-kinase (PI3K) inhibitor, a TORC inhibitor, or a dual PI3K/TORC inhibitor (e.g., BEZ-235, BKM120, BGT226, BYL-719, GDC0068, GDC-0980, GDC0941, GDC0032, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101, PWT33597, LY-317615 (enzastaurin hydrochloride), CU-906, or CUDC-907); a CYP17 inhibitor (e.g., abiraterone acetate (Zytiga), TAK-700 (orteronel), or VT-464); prednisone; an osteoprotective agent; a radiation therapy; a kinase inhibitor (e.g. MET, VEGFR, EGFR, MEK, SRC, AKT, RAF, FGFR, CDK4/6); Provenge, Prostvac, Ipilimumab, a PD-1 inhibitor; a taxane or tubulin inhibitor; an anti-STEAP-1 antibody; a heat shock protein 90 (HSP90) or heat shock protein 27 (HSP27) pathway modulator; an anti-androgen (e.g. bicalutamide); and/or immunotherapy.

The active agent(s) also can be administered with olaparib, bevacizumab, albumin bound paclitaxel, altretamine, capecitabine, cyclophosphamide, etoposide, gemcitabine, ifosfamide, irinotecan, liposomal doxorubicin, melphalan, pemetrexed, topotecan, or vinorelbine.

In particular embodiments, the active agent(s) are administered with cisplatin and/or docetaxel.

Active agent(s) can also be administered with anesthetics including ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and/or phenazopyridine.

Combination therapies refer to those situations in which two or more different active agent(s) are administered in overlapping regimens so that the subject is simultaneously exposed to both agents in therapeutically effective amounts.

Methods disclosed herein can further include determining whether a subject has developed chemoresistance to first-line or second-line chemotherapeutic agents prior to administering a therapeutically effective amount. In particular embodiments, the disclosed compositions and methods can be utilized when chemoresistant cancer cells are detected in a subject. In particular embodiments, the disclosed compositions and methods can be utilized before chemoresistant cancer cells are detected in a subject.

As suggested, the one or more active agent(s) can be formulated into a composition for administration. Compositions include at least one active agent and at least one pharmaceutically-acceptable carrier and/or excipient.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Examples of suitable aqueous and non-aqueous carriers, which may be employed in the injectable formulations include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of selected particle size in the case of dispersions, and by the use of surfactants.

Particular embodiments can be clear, colorless, sterile, non-pyrogenic solutions for intravenous (IV) use. Single use vials containing 2 mg/mL of Abciximab and/or NIF in a buffered solution (pH7.2) of 0.01 M sodium phosphate, 0.15 M sodium chloride and 0.001% polysorbate 80 in Water for Injection can be provided. In particular embodiments of this formulation, no preservatives are added.

Injectable formulations may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like in the compositions.

Alternatively, the composition can be in lyophilized form and/or provided in powder form for constitution with a suitable vehicle, e.g., sterile pyrogen-free water, before use. Lyophilized compositions can include less than 5% water content; less than 4.0% water content; or less than 3.5% water content.

In particular embodiments, the composition can be in a unit dosage form, such as in a suitable diluent in sterile, hermetically sealed ampoules or sterile syringes.

In particular embodiments, in order to prolong the effect of a composition, it is desirable to slow the absorption of the active agent(s) following injection. Compositions can be formulated as sustained-release systems utilizing semipermeable matrices of solid polymers containing at least one administration form. Various sustained-release materials have been established and are well known by those of ordinary skill in the art. Sustained-release systems may, depending on their chemical nature, release agents following administration for a few weeks up to over 100 days.

In particular embodiments, delayed absorption can be accomplished by dissolving or suspending the active agent(s) in an oil vehicle. In particular embodiments, administration forms can be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts. In addition, prolonged absorption of the injectable composition may be brought about by the inclusion of active agent(s) which delay absorption such as aluminum monostearate and gelatin.

Injectable depot forms can be made by forming microencapsule matrices of administration forms in biodegradable polymers such as polylactide-polyglycolide. Depending on the ratio of administration form to polymer, and the nature of the particular polymer employed, the rate of administration form release can be controlled. Examples of other biodegradable polymers include poly(orthoesters) and poly (anhydrides). Injectable depot formulations are also prepared by entrapping the active agent(s) in liposomes or microemulsions which are compatible with body tissue.

Alternatively, delayed absorption of a composition can be accomplished by the use of a liquid suspension of crystalline or amorphous material having poor water solubility. The rate of absorption of the active agent(s) then depends upon its rate of dissolution which, in turn, may depend upon crystal size and crystalline form.

Compositions can also be formulated for oral administration. For ingestion, compositions can take the form of tablets, pills, lozenges, sprays, liquids, and capsules formulated in conventional manners. Ingestible compositions can be prepared using conventional methods and materials known in the pharmaceutical art. For example, U.S. Pat. Nos. 5,215,754 and 4,374,082 relate to methods for preparing swallowable compositions. U.S. Pat. No. 6,495,177 relates to methods to prepare chewable supplements with improved mouthfeel. U.S. Pat. No. 5,965,162, relates to compositions and methods for preparing comestible units which disintegrate quickly in the mouth.

Ingestible compositions may have a shape containing no sharp edges and a smooth, uniform and substantially bubble free outer coating. Coatings of ingestible compositions can be derived from a polymeric film. Such film coatings reduce the adhesion of the compositions to the inner surface of the mouth and can aid in masking potential unpleasant tastes. Coatings can also protect the compositions from atmospheric degradation. Exemplary polymeric films include vinyl polymers, cellulosics, acrylates and methacrylates, natural gums and resins such as zein, gelatin, shellac and acacia. Other common excipients used in ingestible compositions include sucrose, fructose, lactose, glucose, lycasin, xylitol, lactitol, erythritol, mannitol, isomaltose, dextrose, polydextrose, dextrin, compressible cellulose, compressible honey, compressible molasses, fondant or gums, vegetable oils, animal oils, alkyl polysiloxanes, corn starch, potato starch, pre-gelatinized starches, stearic acid, calcium stearate, magnesium stearate, zinc stearate, benzoic acid, and colorants For administration by inhalation (e.g., nasal or pulmonary), the compositions can be formulated as aerosol sprays for pressurized packs or a nebulizer, with the use of suitable propellants, e.g. dichlorodifluoromethane, trichlorofluoromethane, or dichlorotetra-fluoroethane.

As suggested, nanoparticle formulations for a variety of administration routes can also be used.

Any composition disclosed herein can advantageously include any other pharmaceutically acceptable carriers which include those that do not produce significantly adverse, allergic, or other untoward reactions that outweigh the benefit of administration, whether for research, prophylactic, and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants. Fillers and excipients are commercially available from companies such as Aldrich Chemical Co., FMC Corp, Bayer, BASF, Alexi Fres, Witco, Mallinckrodt, Rhodia, ISP, and others.

Active agent(s) include their pharmaceutically acceptable salts and/or pro-drugs. A pharmaceutically acceptable salt includes any salt that retains the activity of the active agent(s) and is acceptable for pharmaceutical use. A pharmaceutically acceptable salt also refers to any salt which may form in vivo as a result of administration of an acid, another salt, or a prodrug which is converted into an acid or salt.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable pharmaceutically acceptable base addition salts include metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine.

A prodrug includes an active agent which is converted to a therapeutically active compound after administration, such as by cleavage of a protein or by hydrolysis of a biologically labile group.

In particular embodiments, the compositions can include, for example, 25 µg/mL or mg-5 mg/mL or mg, 50 µg/mL or mg-5 mg/mL or mg, 100 µg/mL or mg-5 mg/mL or mg, 150 µg/mL or mg-5 mg/mL or mg, 200 µg/mL or mg-5 mg/mL or mg, 250 µg/mL or mg-5 mg/mL or mg, 300 µg/mL or mg-5 mg/mL or mg, 350 µg/mL or mg-5 mg/mL or mg, 400 µg/mL or mg-5 mg/mL or mg, 450 µg/mL or mg-5 mg/mL or mg, 500 µg/mL or mg-5 mg/mL or mg, 550 µg/mL or mg-5 mg/mL or mg, 600 µg/mL or mg-5 mg/mL or mg, 650 µg/mL or mg-5 mg/mL or mg, 700 µg/mL or mg-5 mg/mL or mg, 750 µg/mL or mg-5 mg/mL or mg, 800 µg/mL or mg-5 mg/mL or mg, 850 µg/mL or mg-5 mg/mL or mg, 900 µg/mL or mg-5 mg/mL or mg, 950 µg/mL or mg-5 mg/mL or mg, 1 mg/mL or mg-5 mg/mL or mg, 1.5 mg/mL or mg-5 mg/mL or mg, 2 mg/mL or mg-5 mg/mL or mg, 2.5 mg/mL or mg-5 mg/mL or mg, 3 mg/mL or mg-5 mg/mL or mg, 3.5 mg/mL or mg-5 mg/mL or mg, 4 mg/mL or mg-5 mg/mL or mg, 4.5 mg/mL or mg-5 mg/mL or mg, 25 µg/mL or mg-2.5 mg/mL or mg, 50 µg/mL or mg-2.5 mg/mL or mg, 100 µg/mL or mg-2.5 mg/mL or mg, 150 µg/mL or mg-2.5 mg/mL or mg, 200 µg/mL or mg-2.5 mg/mL or mg, 250 µg/mL or mg-2.5 mg/mL or mg, 300 µg/mL or mg-2.5 mg/mL or mg, 350 µg/mL or mg-2.5 mg/mL or mg, 400 µg/mL or mg-2.5 mg/mL or mg, 450 µg/mL or mg-2.5 mg/mL or mg, 500 µg/mL or mg-2.5 mg/mL or mg, 550 µg/mL or mg-2.5 mg/mL or mg, 600 µg/mL or mg-2.5 mg/mL or mg, 650 µg/mL or mg-2.5 mg/mL or mg, 700 µg/mL or mg-2.5 mg/mL or mg, 750 µg/mL or mg-2.5 mg/mL or mg, 800 µg/mL or mg-2.5 mg/mL or mg, 850 µg/mL or mg-2.5 mg/mL or mg, 900 µg/mL or mg-2.5 mg/mL or mg, 950 µg/mL or mg-2.5 mg/mL or mg, 1 mg/mL or mg-2.5 mg/mL or mg, 1.5 mg/mL or mg-2.5 mg/mL or mg, 2 mg/mL or mg-2.5 mg/mL or mg, 25 µg/mL or mg-1 mg/mL or mg, 50 µg/mL or mg-1 mg/mL or mg, 100 µg/mL or mg-1 mg/mL or mg, 150 µg/mL or mg-1 mg/mL or mg, 200 µg/mL or mg-1 mg/mL or mg, 250 µg/mL or mg-1 mg/mL or mg, 300 µg/mL or mg-1 mg/mL or mg, 350 µg/mL or mg-1 mg/mL or mg, 400 µg/mL or mg-1 mg/mL or mg, 450 µg/mL or mg-1 mg/mL or mg, 500 µg/mL or mg-1 mg/mL or mg, 550 µg/mL or mg-1 mg/mL or mg, 600 µg/mL or mg-1 mg/mL or mg, 650 µg/mL or mg-1 mg/mL or mg, 700 µg/mL or mg-1 mg/mL or mg, 750 µg/mL or mg-1 mg/mL or mg, 800 µg/mL or mg-1 mg/mL or mg, 850 µg/mL or mg-1 mg/mL or mg, 900 µg/mL or mg-1 mg/mL or mg, 950 µg/mL or mg-1 mg/mL or mg, 25 µg/mL or mg-750 µg/mL or mg, 50 µg/mL or mg-750 µg/mL or mg, 100 µg/mL or mg-750 µg/mL or mg, 150 µg/mL or mg-750 µg/mL or mg, 200 µg/mL or mg-750 µg/mL or mg, 250 µg/mL or mg-750 µg/mL or mg, 300 µg/mL or mg-750 µg/mL or mg, 350 µg/mL or mg-750 µg/mL or mg, 400 µg/mL or mg-750

µg/mL or mg, 450 µg/mL or mg-750 µg/mL or mg, 500 µg/mL or mg-750 µg/mL or mg, 550 µg/mL or mg-750 µg/mL or mg, 600 µg/mL or mg-750 µg/mL or mg L, 650 µg/mL or mg-750 µg/mL or mg, 700 µg/mL or mg-750 µg/mL or mg, 25 µg/mL or mg-500 µg/mL or mg, 50 µg/mL or mg-500 µg/mL or mg, 100 µg/mL or mg-500 µg/mL or mg, 150 µg/mL or mg-500 µg/mL or mg, 200 µg/mL or mg-500 µg/mL or mg, 250 µg/mL or mg-500 µg/mL or mg, 300 µg/mL or mg-500 µg/mL or mg, 350 µg/mL or mg-500 µg/mL or mg, 400 µg/mL or mg-500 µg/mL or mg, 450 µg/mL or mg-500 µg/mL or mg, 25 µg/mL or mg-250 µg/mL or mg, 50 µg/mL or mg-250 µg/mL or mg, 100 µg/mL or mg-250 µg/mL or mg, 150 µg/mL or mg-250 µg/mL or mg, 200 µg/mL or mg-250 µg/mL or mg, 25 µg/mL or mg-100 µg/mL or mg, or 50 µg/mL or mg-100 µg/mL or mg of one or more of the active agent(s).

In particular embodiments, ratios of active agent(s) can include: (e.g., Abciximab:NIF (and whether in the same or different compositions)): 1:0.0001; 1:0.001; 1:0.005; 1:0.0075; 1:0.01; 1:0.05; 1:0.075; 1:0.1; 1:0.5; 1:0.75; 1:1; 1:1.25; 1:1.5; 1:1.75; 1:8; 1:1.2; 1:1.25; 1:1.3; 1:1.35; 1:1.4; 1:1.5; 1:1.75; 1:2; 1:3; 1:4; 1:5; 1:6:1:7; 1:8; 1:9; 1:10; 1:15; 1:20; 1:30; 1:40; 1:50; 1:60; 1:70; 1:80; 1:90; 1:100; 1:200; 1:300; 1:400; 1:500; 1:600; 1:700; 1:800; 1:900; 1:1000. In these exemplary embodiments, Abciximab and/or NIF can be replaced with other anti-CD11b antibodies, anti-integrin αV antibodies, anti-integrin β1 antibodies, human cathelicidin peptide LL-37, Clopidogrel, Cilostazol, compounds of Formula I, Intetumumab, Abituzumab, or a combination thereof in all potential combinations.

In particular embodiments, Abciximab:NIF (or other active agent(s) described herein) can be expressed as a fusion protein and included within a composition. Expression of fusion proteins is well known, and fusion proteins can include any appropriate linkers or spacers to facilitate bioavailability of fused proteins. Proteins can also be linked through any other mechanism known or available to those of ordinary skill in the art. In particular embodiments, fusion proteins including active agent(s) disclosed herein can further include a targeting molecule, an apoptosis inducer or an angiogenesis inhibitor.

Whether alone or in combination, proteins disclosed herein can be administered as the proteins themselves or as nucleic acids encoding the proteins (whether fused or individually).

Any vector suitable for administering nucleic acid molecules encoding proteins to a solid tumor cell such that the solid tumor cells express the proteins may be employed. In particular embodiments, the nucleic acid molecule is incorporated into a viral particle to mediate gene transfer to a solid tumor cell. In particular embodiments, the virus simply can be exposed to the appropriate host cell under physiologic conditions, permitting uptake of the virus. Examples of viral vectors include those derived from adenovirus, adeno-associated virus, retrovirus, lentivirus, herpes simplex virus, vaccinia virus, etc.

In particular embodiments, the nucleic acids or the vectors including the nucleic acids can be transfected into cells by ex vivo transformation; injection, such as subcutaneous, intradermal, intramuscular, intravenous, intraperitoneal injection; liposome mediated transfection; receptor mediated transfection; etc.

Vectors can include regulatory sequences to control the expression of the nucleic acid molecules. These regulatory sequences can be eukaryotic or prokaryotic in nature. In particular embodiments, the regulatory sequence can be a tissue specific promoter such that the expression of the protein will be substantially greater in the target tissue type (i.e., solid tumor) compared to other types of tissue. In particular embodiments, the regulatory sequence can result in the constitutive expression of the protein upon entry of the vector into the cell. Alternatively, the regulatory sequences can include inducible sequences. Inducible regulatory sequences are well known to those skilled in the art and are those sequences that require the presence of an additional inducing factor to result in expression of protein. Examples of suitable regulatory sequences include binding sites corresponding to tissue-specific transcription factors based on endogenous nuclear proteins, sequences that direct expression in a specific cell type, the lac operator, the tetracycline operator and the steroid hormone operator. Any inducible regulatory sequence known to those of skill in the art may be used in conjunction with uses of compositions and methods disclosed herein.

In particular embodiments, the nucleic acid is stably integrated into the genome of a subset of a subject's cells. In particular embodiments, the nucleic acid is stably maintained in a subset of a subject's cells as a separate, episomal segment.

In particular embodiments, the efficiency of integration, the size of the nucleic acid sequence that can be integrated, and the number of copies of a nucleic acid sequence that can be integrated into a genome can be improved by using transposons. Transposons or transposable elements include a short nucleic acid sequence with terminal repeat sequences upstream and downstream. Active transposons can encode enzymes that facilitate the excision and insertion of nucleic acid into a target nucleic acid (e.g., DNA) sequence.

A number of transposable elements have been described in the art that facilitate insertion of nucleic acids into the genome of vertebrates, including humans. Examples include sleeping beauty (e.g., derived from the genome of salmonid fish); piggyback (e.g., derived from lepidopteran cells and/or the *Myotis lucifugus*); mariner (e.g., derived from *Drosophila*); frog prince (e.g., derived from *Rana pipiens*); Tol2 (e.g., derived from medaka fish); TcBuster (e.g., derived from the red flour beetle *Tribolium castaneum*) and spinON.

In particular embodiments, active agent(s) are provided as conjugates including an active agent(s) that targets CD11b/CD18, MPO, and/or Integrin αVβ1 and a chemotherapeutic and/or cytotoxic agent. Examples of chemotherapeutic/cytotoxic agents include capecitabine, paclitaxel, gemcitabine, methotrexate, doxorubicin, docetaxel, cisplatin, and daunorubicin.

Regarding NIF particularly, and due to its size, additional considerations may be warranted in formulation. Here, particularly, although useful with other active agent(s) as well, carrier molecules for effective delivery and hypersensitivity reduction can be used. Exemplary carrier molecules include liposomes, lipid micelles, lipoprotein micelles and polymeric micelles. Other carrier molecules include polymer nanoparticles such as polycyanoacrylate nanoparticles and PEGylated nanoparticles, polymer microparticles, block copolymer micelles, lipid stabilized emulsions, polymer-lipid hybrid systems and derivatized single chain polymers and other linear, spherical or tubular polymers. The carriers may further include carbon or other nanotubes including linear and spherical, uni- and multiwalled nanotubes. The carriers may also include dendrimers such as PAMAM dendrimers, and fullerenes.

In particular embodiments incorporating proteins such as Abciximab, the proteins can be produced by continuous perfusion in mammalian cell culture. For Abciximab particularly, the 47,615 Dalton Fab fragment can be purified.

All relevant protein products can be purified from cell culture supernatant by a series of steps involving specific viral inactivation and removal procedures, digestion with papain and column chromatography.

The present disclosure further provides for kits including one or more treatment options (e.g., single or combination therapies) and/or chemoresistance detection assays for practicing any of the methods disclosed herein. The kits may include a notice in the form prescribed by a governmental agency regulating the manufacture, use or sale of pharmaceuticals, biological products, lab developed tests, etc., which notice reflects approval by the agency of the manufacture, use or sale for human administration and/or testing. Treatment portions of the kits may include agent(s) in a ready-to-use form and/or a form that requires preparation before administration (e.g., lyophilized). Chemoresistance detection assay portions of the kits may utilize any necessary or appropriate cellular assays, polypeptides, conjugates, antibodies, polynucleotides, expression vectors, cells, methods, compositions, systems, and/or apparatuses useful for the detection of chemoresistance and/or C11b, CD18, CD51 and/or CD29.

The Exemplary Embodiments and Example below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure. More particularly, to the extent not previously stated herein, any molecule, agent, protein, peptide, or antibody that is capable of binding aberrantly expressed β2 integrin (CD11b/CD18), MPO, and/or Integrin αVβ1 in solid tumors or cells can serve as a therapeutic intervention providing one or more of prevention, treatment, vaccination, elimination or reduction of cancer cells, elimination or reduction of chemoresistant cells, elimination or reduction of cancer stem cells and/or elimination or reduction of benign tumors (e.g. fibroids).

The following description of terms supports the current disclosure.

Chemoresistant: The resistance of a cell to the actions of a chemical compound.

HOSEpiC: Human Ovarian Surface Epithelial Cells (HOSEpiC) provided by ScienCell Research Laboratories from human ovarian tissue. HOSEpiC are cryopreserved at primary culture and delivered frozen. HOSEpiC are guaranteed to further expand for 5 population doublings in the conditions provided by ScienCell Research Laboratories. Used as control cells.

MDAH-2774: MDAH-2774 (CRL-10303) cell line was obtained from American Type Culture Collection (ATCC, Manassas, Va.) and was developed from cells in the ascitic fluid from a patient with endometrioid ovarian cancer and forms tumors in nude mice.

SKOV-3: The SKOV-3 (HTB-75) cell line was obtained from American Type Culture Collection (ATCC, Manassas, Va.). A human adenocarcinoma cell line that was isolated from ascitic fluid of a 64 year old patient in 1973. Grows in nude mice; forms moderately well differentiated adenocarcinoma consistent with ovarian primary cancer. SKOV-3 cells are resistant to tumor necrosis factor and to several cytotoxic drugs including diphtheria toxin, cis-platinum and Adriamycin.

A2780: The A2780 human ovarian cancer cell line was established from tumor tissue from an untreated patient and was obtained from Sigma Aldrich. Cells grow as a monolayer. A2780 is the parent line to the cisplatin resistant cell line A2780 cis, which is resistant to 1 uM cisplatin.

OV-90: The OV-90 (CRL-11732) cell line was obtained from American Type Culture Collection (ATCC, Manassas, Va.). A human serous adenocarcinoma cell line that was isolated from ascitic fluid of a 64 year old patient in 1992. The cells are tumorigenic in nude mice.

OV-21: The OV-21 (TOV-21G, CRL-11730) cell line was obtained from American Type Culture Collection (ATCC, Manassas, Va.). A human adenocarcinoma cell line that was isolated from ascitic fluid of a 62 year old patient in 1991. The cells are tumorigenic in nude mice.

OVCAR-3: The OVCAR-3 (HTB-161) cell line was obtained from American Type Culture Collection (ATCC, Manassas, Va.). A human adenocarcinoma cell line that was isolated from ascitic fluid of a 60 year old patient in 1982. The cells are tumorigenic in nude mice. Cells are resistant to clinically relevant concentrations of adriamycin, melphalan and cisplatin.

T24: The T24 (HTB-4) cell line was obtained from American Type Culture Collection (ATCC, Manassas, Va.). The human urinary bladder transitional cell carcinoma was derived from an 81 year old Caucasian female.

Caco-2: The Caco-2 (HTB-37) cell line was obtained from American Type Culture Collection (ATCC, Manassas, Va.). The colorectal adenocarcinoma cell line was derived from a 72 year old Caucasian male.

RL95-2: The RL95-2 (CRL-1671) cell line was obtained from American Type Culture Collection (ATCC, Manassas, Va.). The endometrial carcinoma cell line was derived from a 65 year old Caucasian female.

NCI-H1688: The NCI-H1688 (CCL-257) cell line was obtained from American Type Culture Collection (ATCC, Manassas, Va.). The lung carcinoma cell line was derived from the metastatic site (liver) and is a classic small cell lung cancer cell line. The cell line was obtained from a 50 year old Caucasian male.

Hep G2: The HEP-G2 (HB-8065) cell line was obtained from American Type Culture Collection (ATCC, Manassas, Va.). The liver (hepatocellular) carcinoma cell line was derived from a 15 year old Caucasian male.

LNCaP clone FGC: The LNCaP clone FGC (CRL-1740) cell line was obtained from American Type Culture Collection (ATCC, Manassas, Va.). The prostate carcinoma cell line was derived from the metastatic site (left supraclavicular lymph node) of a 50 year old Caucasian male.

BxPC-3: The BxPC-3 (CRL-1687) cell line was obtained from American Type Culture Collection (ATCC, Manassas, Va.). The pancreatic adenocarcinoma cell line was derived from a 61 year old female.

Hydrogen Peroxide ($H_2O_2$): $H_2O_2$ is released following tissue injury and may act as one of the early signals for the recruitment and activation of immune cells. The elevation of $H_2O_2$ in the cytosol of immune cells appears to be a key signal that links a broad variety of biotic and abiotic stresses to the triggering of the inflammatory response.

Hypochlorous Acid (HOCl): Hypochlorous acid is a weak acid with the chemical formula HOCl. It forms when chlorine dissolves in water, and it is HOCl that actually does the disinfection when chlorine is used to disinfect water for human use.

Natural Killer Cell (NK Cells): NK cells are a type of cytotoxic lymphocyte critical to the innate immune system. The role NK cells play is analogous to that of cytotoxic T cells in the vertebrate adaptive immune response. NK cells provide rapid responses to viral-infected cells and respond to tumor formation, acting at around 3 days after infection. NK cells are known to differentiate and mature in the bone marrow, lymph nodes, spleen, tonsils, and thymus, where they then enter into the circulation.

Polymorphonuclear Leukocyte (PMN): In common parlance, the term polymorphonuclear leukocyte often refers specifically to neutrophil granulocytes, the most abundant of the granulocytes; the other types (eosinophils, basophils, and mast cells) have lower numbers. Granulocytes are produced via granulopoiesis in the bone marrow.

Scratch Assay: In a scratch wound healing assay, a "wound gap" in a cell monolayer is created by scratching utilizing a pipette tip, and the "healing" of this gap, which is 1 mm wide, by cell migration and growth towards the center of the gap is monitored and quantitated.

Toll Like Receptor 4 (TLR-4): TLR 4 is a toll-like receptor. It detects lipopolysaccharide from Gram-negative bacteria and is thus important in the activation of the innate immune system. Overexpression of TLR4 in human tumors often correlates with chemoresistance and metastasis.

Receptor Tyrosine Kinase Inhibitors (RTKI's): The protein kinase inhibitors are a large group of unique and potent antineoplastic agents that specifically target protein kinases that are altered in cancer cells and that account for some of their abnormal growth. Protein kinases are ubiquitous intracellular and cell surface proteins that play critical roles in cell signaling pathways involved in metabolism, injury responses, adaption, growth and differentiation. They act by adding a phosphate group to a protein (phosphorylation), usually on a specific amino acid, which often makes the protein or enzyme "active". The human genome has more than 500 protein kinases and they can be classified as (1) tyrosine, (2) serine-threonine or (3) nonspecific (both), based upon their amino acid specificity.

EXEMPLARY EMBODIMENTS

1. A method of treating a solid tumor in a subject in need thereof including administering a therapeutically effective amount of one or more active agent(s) that inhibits, suppresses and/or eliminates CD11b/CD18, MPO, and/or Integrin αVβ1 activity in the subject, thereby treating the solid tumor.

2. A method of embodiment 1 wherein the solid tumor is a benign solid tumor or a cancerous solid tumor.

3. A method of embodiment 1 or 2 wherein the solid tumor is a benign fibroid tissue solid tumor.

4. A method of embodiment 3 wherein the benign fibroid tissue solid tumor is a uterine fibroid.

5. A method of any of embodiments 1-3 wherein the solid tumor causes adhesive capsulitis, arterial fibrosis, arthrofibrosis, Crohn's disease, cirrhosis, cystic fibrosis, endomyocardial fibrosis, fibrous cysts, idiopathic pulmonary fibrosis, keloids, mediastinal fibrosis, myelofibrosis, nephrogenic systemic fibrosis, Peyronie's disease, pulmonary fibrosis, progressive massive fibrosis, retroperitoneal fibrosis, sclerodermalsystemic sclerosis, uterine fibroids (uterine leiomyomas), and/or a precancerous fibroma in the subject.

6. A method of embodiment 2 wherein the cancerous solid tumor is a pre-malignant solid tumor or a malignant solid tumor.

7. A method of embodiment 6 wherein the cancerous solid tumor is a chemoresistant solid tumor.

8. A method of embodiment 6 or 7 wherein the cancerous solid tumor is acoustic neuroma, adenocarcinoma, astrocytoma, basal cell cancer, bile duct cancer, bladder cancer, breast cancer, bronchogenic cancer, central nervous system cancer, cervical cancer, chondrosarcoma, choriocarcinoma, colon cancer, craniopharyngioma, ependymoma, Ewing's tumor, fibrosarcoma, glioma, hemangioblastoma, hepatocellular carcinoma, hepatoma, leiomyosarcoma, liposarcoma, lung cancer, melanoma, medulloblastoma, medullary cancer, medullary thyroid cancer, menangioma, mesothelioma, myxosarcoma, neuroblastoma, oligodendroglioma, osteogenic sarcoma, ovarian cancer, papillary adenocarcinomas, papillary thyroid cancer, pancreatic cancer, pheochromocytomas papillary cancer, pineal cancer, prostate cancer, renal cell cancer, retinoblastoma, rhabdomyosarcoma, sarcoma, sebaceous gland cancer, seminoma, squamous cell cancer, sweat gland cancer, synovioma, testicular tumor, testicular cancer, and/or Wilms' tumor.

9. A method of any of embodiments 6-8 wherein the cancerous solid tumor is ovarian cancer or breast cancer.

10. A method of any of embodiments 1-9 wherein the treating causes an anti-cancer effect in the subject.

11. A method of any of embodiments 1-10 wherein the one or more active agent(s) include a peptide, antibody, a small molecule, a fusion protein, a conjugate, or a combination thereof.

12. A method of any of embodiments 1-11 wherein the one or more active agent(s) are selected from anti-CD11b antibodies, anti-MPO antibodies, anti-integrin αV antibodies, anti-integrin β1 antibodies, Abciximab, neutrophil inhibitory factor (NIF) protein, human cathelicidin peptide LL-37, Clopidogrel, Cilostazol, Intetumumab, Abituzumab, or a compound of formula (I)

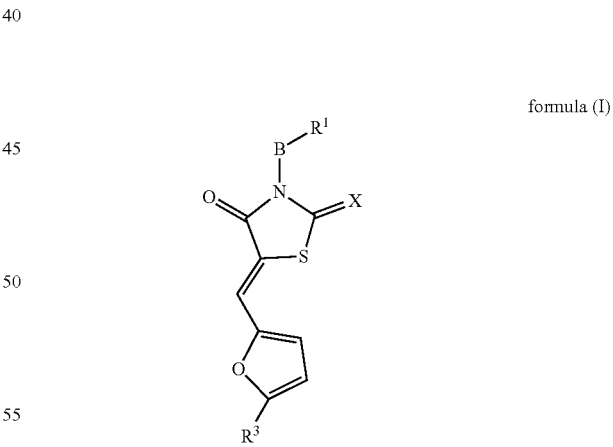

formula (I)

wherein:

B is absent and $R^1$ is phenyl; or

B is methylene and $R^1$ is phenyl or phenyl substituted with one fluoro;

N is nitrogen;

X is selected from the group including O and S; and $R^3$ is selected from the group including 4-carboxyphenyl and 3-carboxy-4-chlorophenyl.

13. A method of embodiment 12, wherein the compound is

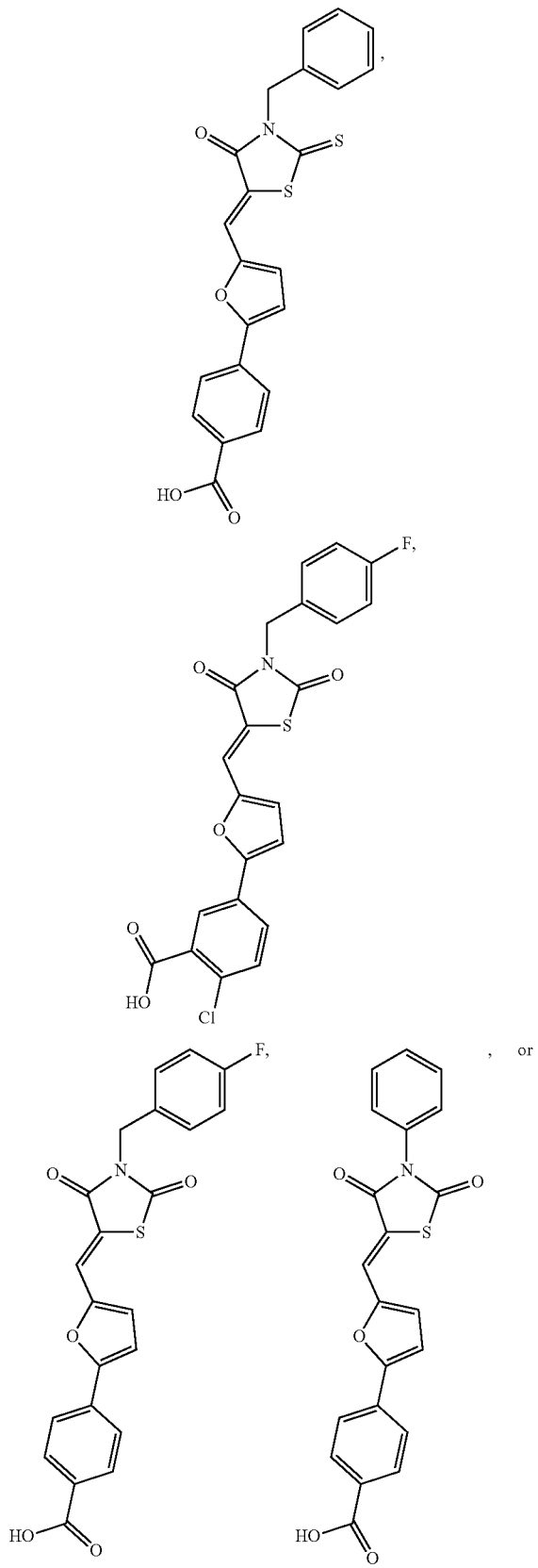

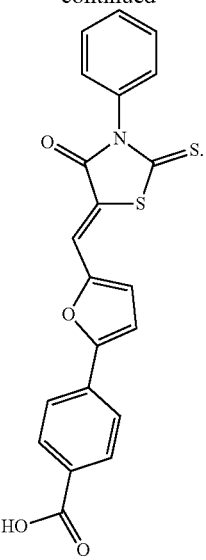

14. A method of any of embodiments 1-12 wherein the one or more active agent(s) are anti-CD11b antibodies, anti-MPO antibodies, anti-integrin αV antibodies, anti-integrin β1 antibodies, Abciximab and/or NIF.

15. A method of any of embodiments 1-12 wherein said active agent is administered in combination with a chemotherapeutic agent.

16. A method of embodiment 15 wherein said chemotherapeutic agent is cisplatin.

17. A method of embodiment 15 wherein said chemotherapeutic agent is docetaxel.

18. A method of any of embodiments 1-17 wherein said active agents include anti-CD11b antibodies in combination with anti-MPO antibodies, anti-integrin αV antibodies, anti-integrin β1 antibodies, Abciximab and/or NIF.

19. A method of any of embodiments 1-18 wherein said active agents include anti-MPO antibodies in combination with anti-CD11b antibodies, anti-integrin αV antibodies, anti-integrin β1 antibodies, Abciximab and/or NIF.

20. A method of any of embodiments 1-19 wherein said active agents include anti-integrin αV antibodies in combination with anti-CD11b antibodies, anti-MPO antibodies, anti-integrin β1 antibodies, Abciximab and/or NIF.

21. A method of any of embodiments 1-20 wherein said active agents include anti-integrin β1 antibodies in combination with anti-CD11b antibodies, anti-MPO antibodies, anti-integrin αV antibodies, Abciximab and/or NIF.

22. A method of any of embodiments 1-21 wherein said active agents include Abciximab in combination with anti-CD11b antibodies, anti-MPO antibodies, anti-integrin αV antibodies, anti-integrin β1 antibodies and/or NIF.

23. A method of any of embodiments 1-22 wherein said active agents include NIF in combination with anti-CD11b antibodies, anti-MPO antibodies, anti-integrin αV antibodies, anti-integrin β1 antibodies and/or Abciximab.

24. A method of any of embodiments 1-23 wherein the active agent(s) are administered in protein or nucleic acid form.

25. A method of any of embodiments 1-24 wherein the active agent(s) are provided in therapeutically effective amounts as part of a composition.

26. A composition including a therapeutically effective amount of one or more active agent(s) that target CD11b/CD18, MPO, and/or Integrin αVβ1.

27. A composition of embodiment 26 wherein the one or more active agent(s) include a peptide, antibody, a small molecule, a fusion protein, a conjugate, or a combination thereof.

28. A composition of embodiment 26 or 27 wherein the one or more active agent(s) are selected from anti-CD11b antibodies, anti-MPO antibodies, anti-integrin αV antibodies, anti-integrin β1 antibodies, Abciximab, neutrophil inhibitory factor (NIF) protein, human cathelicidin peptide LL-37, Clopidogrel, Cilostazol, Intetumumab, Abituzumab, or a compound of formula (I)

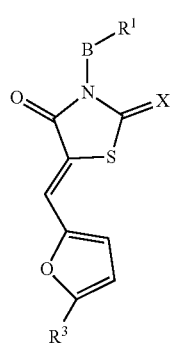

formula (I)

wherein:

B is absent and R¹ is phenyl; or

B is methylene and R¹ is phenyl or phenyl substituted with one fluoro;

N is nitrogen;

X is selected from the group including O and S; and

R³ is selected from the group including 4-carboxyphenyl and 3-carboxy-4-chlorophenyl.

29. A composition of embodiment=28, wherein the compound is

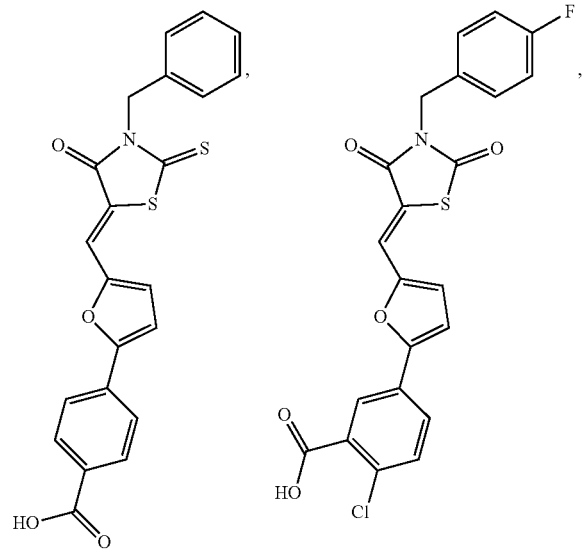

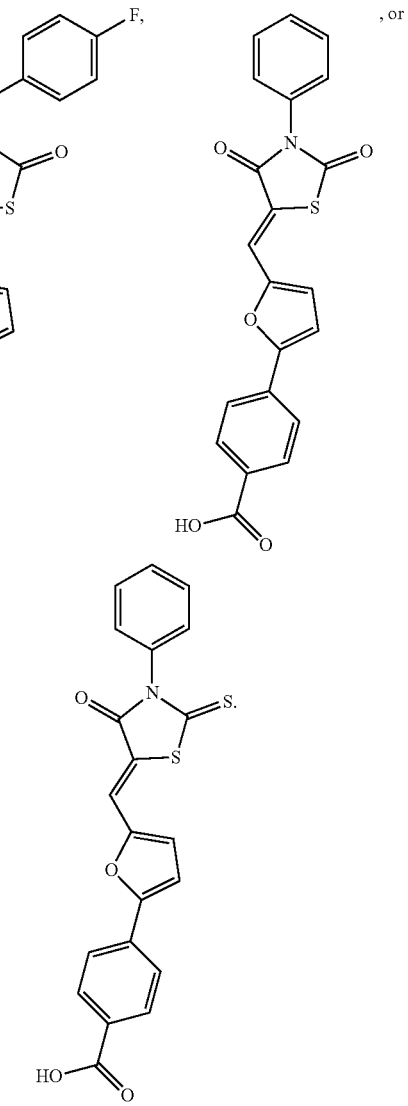

30. A composition of any of embodiments 26-29 wherein the one or more active agent(s) include anti-CD11b antibodies, anti-MPO antibodies, anti-integrin αV antibodies, anti-integrin β1 antibodies, Abciximab and/or NIF.

31. A composition of any of embodiments 26-30 wherein said active agents include anti-CD11b antibodies in combination with anti-MPO antibodies, anti-integrin αV antibodies, anti-integrin β1 antibodies, Abciximab and/or NIF.

32. A composition of any of embodiments 26-31 wherein said active agents include anti-MPO antibodies in combination with anti-CD11b antibodies, anti-integrin αV antibodies, anti-integrin β1 antibodies, Abciximab and/or NIF.

33. A composition of any of embodiments 26-32 wherein said active agents include anti-integrin αV antibodies in combination with anti-CD11b antibodies, anti-MPO antibodies, anti-integrin β1 antibodies, Abciximab and/or NIF.

34. A composition of any of embodiments 26-33 wherein said active agents include anti-integrin β1 antibodies in combination with anti-CD11b antibodies, anti-MPO antibodies, anti-integrin αV antibodies, Abciximab and/or NIF.

35. A composition of any of embodiments 26-34 wherein said active agents include Abciximab in combination with anti-CD11b antibodies, anti-MPO antibodies, anti-integrin αV antibodies, anti-integrin β1 antibodies and/or NIF.

36. A composition of any of embodiments 26-35 wherein said active agents include NIF in combination with anti-CD11b antibodies, anti-MPO antibodies, anti-integrin αV antibodies, anti-integrin β1 antibodies and/or Abciximab.

37. A composition of any of embodiments 26-36 wherein the therapeutically effective amount provides an anti-solid tumor effect and/or an anti-cancer effect when administered to a subject in need thereof.

38. A method of killing chemoresistant cells in a subject in need thereof including administering a therapeutically effective amount of one or more active agent(s) that target CD11b/CD18, MPO, and/or Integrin αVβ1 to the subject, thereby killing the chemoresistant cells.

39. A method of killing cancer stem cells in a subject in need thereof including administering a therapeutically effective amount of one or more active agent(s) that target CD11b/CD18, MPO, and/or Integrin αVβ11 to the subject, thereby killing the cancer stem cells.

40. A method of embodiment 38 or 39 wherein the one or more active agent(s) include a peptide, antibody, a small molecule, a fusion protein, a conjugate, or a combination thereof.

41. A method of any of embodiments 38-40 wherein the one or more active agent(s) are selected from anti-CD11b antibodies, anti-MPO antibodies, anti-integrin αV antibodies, anti-integrin β1 antibodies, Abciximab, neutrophil inhibitory factor (NIF) protein, human cathelicidin peptide LL-37, Clopidogrel, Cilostazol, Intetumumab, Abituzumab, or a compound of formula (I)

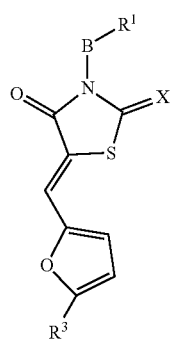

formula (I)

wherein:

B is absent and $R^1$ is phenyl; or

B is methylene and $R^1$ is phenyl or phenyl substituted with one fluoro;

N is nitrogen;

X is selected from the group including O and S; and $R^3$ is selected from the group including 4-carboxyphenyl and 3-carboxy-4-chlorophenyl.

42. A method of embodiment 41, wherein the compound is

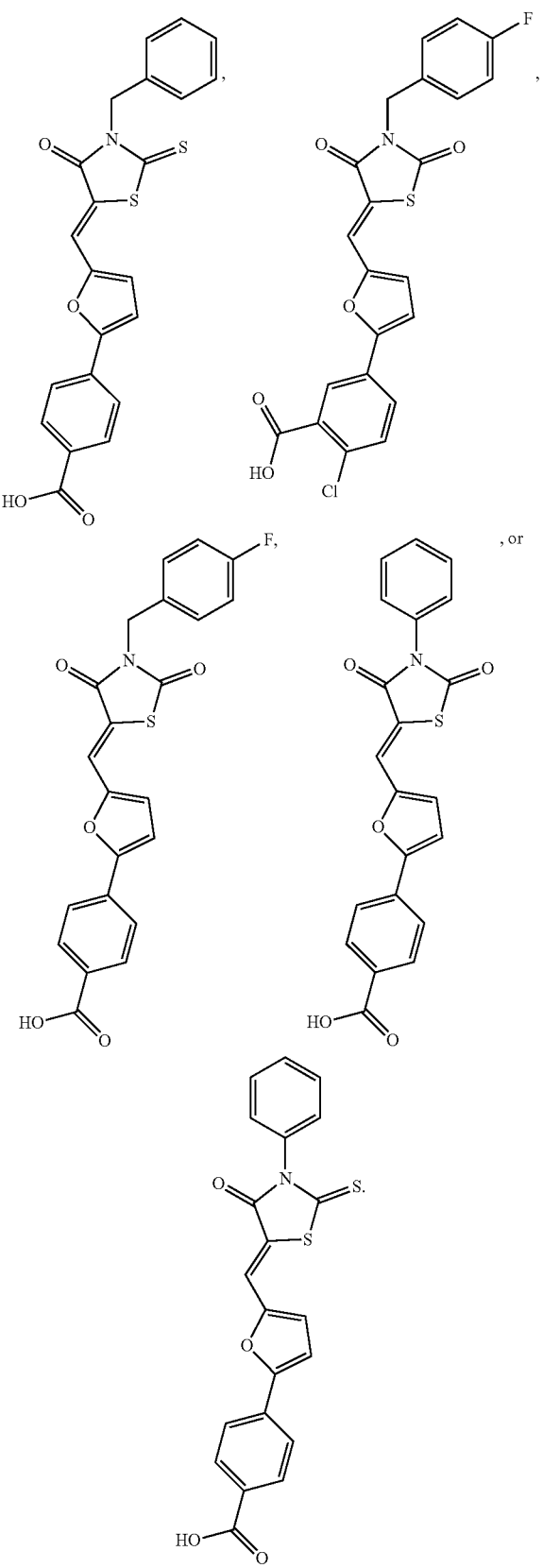

43. A method of any of embodiments 38-42 wherein the one or more active agent(s) are anti-CD11b antibodies, anti-MPO antibodies, anti-integrin αV antibodies, anti-integrin β1 antibodies, Abciximab and/or NIF.
44. A method of any of embodiments 38-41 and 43 wherein the active agent(s) are administered in protein or nucleic acid form.
45. A method of any of embodiments 38-44 wherein the active agent(s) are provided in therapeutically effective amounts as part of a composition.
46. Use of Abciximab or neutrophil inhibitory factor (NIF) protein to treat ovarian cancer.

Example 1. Abciximab's Effects on Solid Tumors: Ovarian Cancer

A2780:

The A2780 human ovarian cancer cell line was established from tumor tissue from an untreated patient and was obtained from Sigma Aldrich. Cells grow as a monolayer. A2780 is the parent line to the cisplatin resistant cell line A2780 cis, which is resistant to 1 μM cisplatin. This cell line is maintained in RPMI media (HyClone, Fisher Scientific) supplemented with 100 U/mL penicillin and 100 μg/mL streptomycin and 10% heat-inactivated fetal bovine serum (FBS, Thermofisher Scientific) at 37° C. in 5% $CO_2$. Culture medium was replaced every two days.

Cancer Stem Cells:

This cell line was derived from the commercially available SKOV-3 EOC cell line (ATCC). These cells were isolated from culture utilizing CD44 and CD117 antibody-conjugated-magnetic beads and were found to express pluripotency makers Oct4, Sox2, and NANOG. Cells are maintained in low-bind 24 well culture dishes in DMEM/F12 media (Hyclone, Fisher) supplemented with 5 μg/ml Insulin, 20 ng/ml EGF, 10 ng/ml FGF, 0.5% BSA, and 1% penicillin and streptomycin at 37° C. in 5% $CO_2$. Healthy cells form spheroids in culture, in low bind culture dishes.

Macrophages:

The commercial EL 1 (macrophage, ATCC) was established from cryopreserved human spleen cells. Cells are maintained in Iscove's modified Dulbecco's medium (ATCC) supplemented with 100 U/mL penicillin and 100 μg/mL streptomycin and 10% heat-inactivated fetal bovine serum (FBS, Thermofisher Scientific) at 37° C. in 5% $CO_2$. Culture medium was replaced every two days.

Cell Viability Assay:

Cell viability was determined using the TACS MTT Cell Proliferation Assay (Trevigen, Gaithersburg, Md.) per the manufacturer's protocol. Briefly, measurement of cell proliferation is based upon the reduction of the tetrazolium salt, 3,[4,5-dimethytthiazol-2-yl]-2,5-diphenyl-tetrazolium bromide (MTT). MTT is reduced to an insoluble formazan dye by mitochondrial enzymes associated with metabolic activity of living cells. Cytotoxic compounds such as chemotherapeutics are able to damage and destroy cells, and thus decrease the reduction of MTT to formazan. A standard curve with seven points was constructed using each respective cell line. Cells were seeded into 96-well plates in a fixed volume of 100 μl at a density of 8000 cells per well, in triplicate. Cells were treated with either neutrophil inhibitory factor (10 μg) or increasing doses of Abciximab for 24 or 72 hours in a cell culture incubator (37° C., 5% $CO_2$) with or with chemotherapeutics. Following incubation, 10 μl of the MTT solution was added to each well and incubated for 2 hours followed by the addition of 100 μl of the Detergent Solution to each well and incubation for an additional 2 hours. Absorbance was measured at 570 nm. A blank containing only medium was subtracted from all test samples. A standard curve was constructed utilizing the OD readings correlating with each standard point and was utilized to determine cell number in the test samples.

Figure 1B:
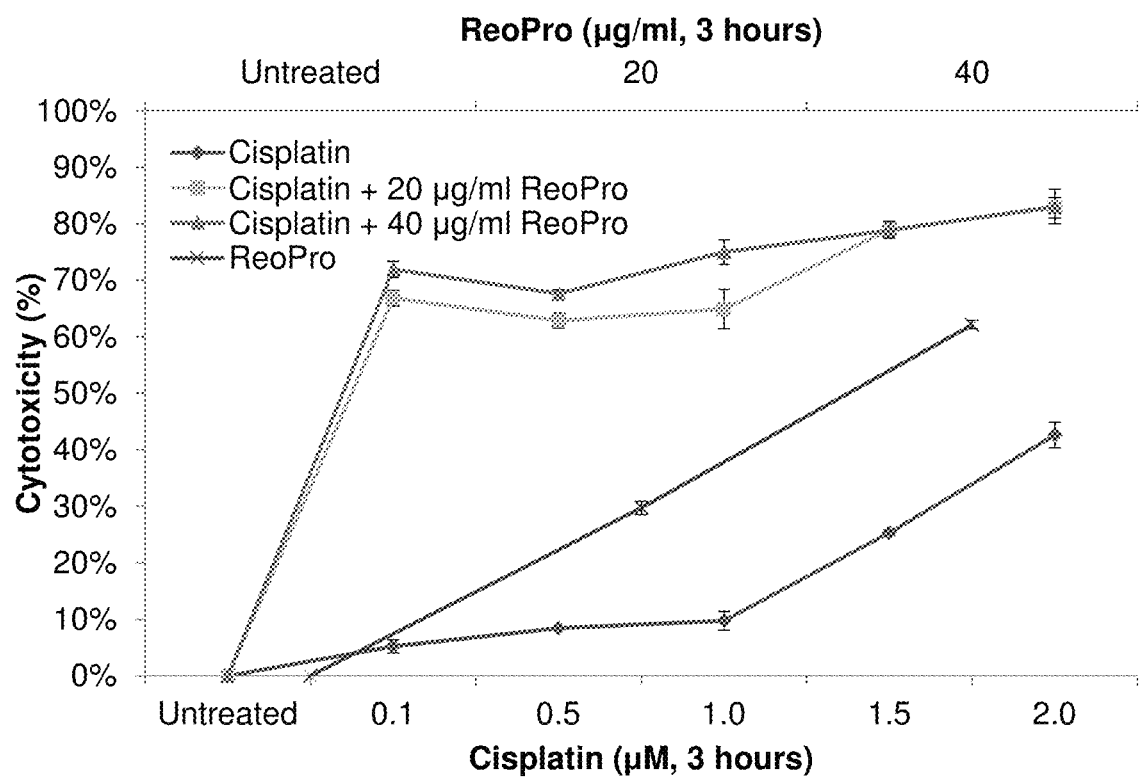
Figure 1C:
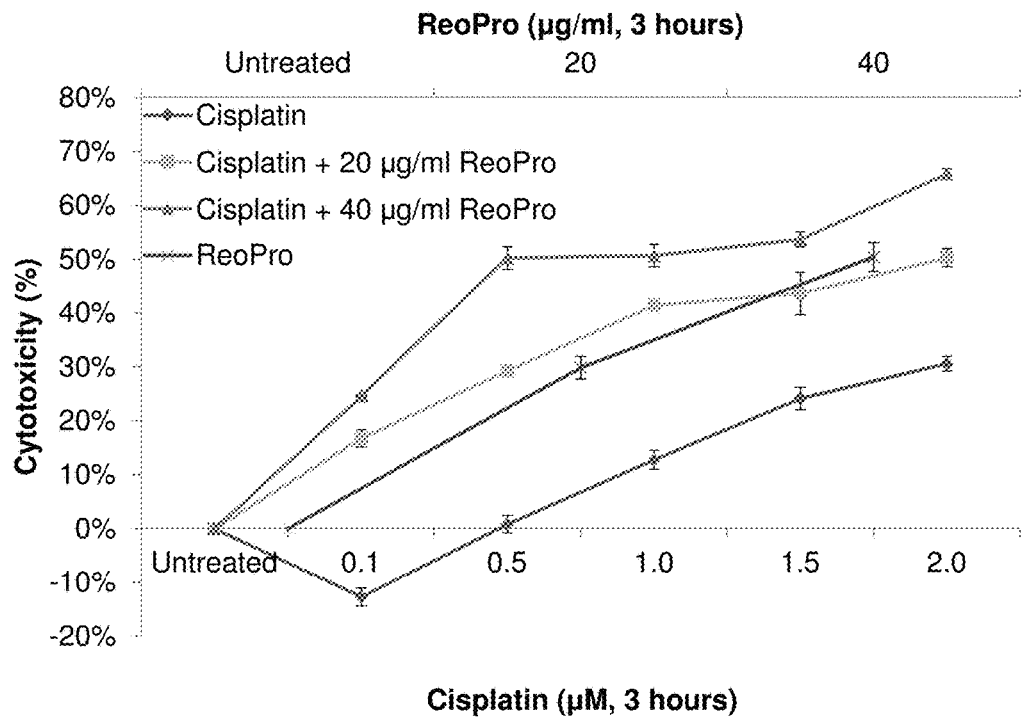
Figure 1D:
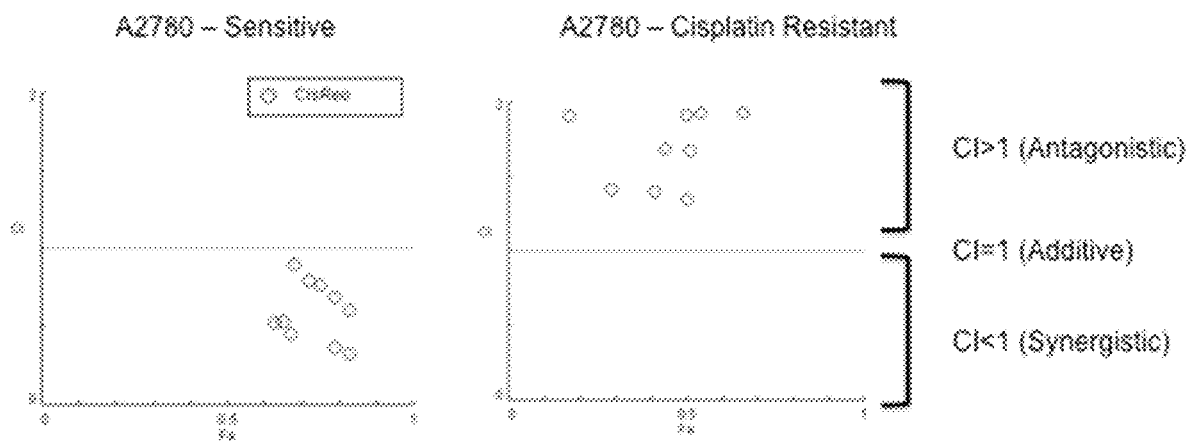
Figure 1E:
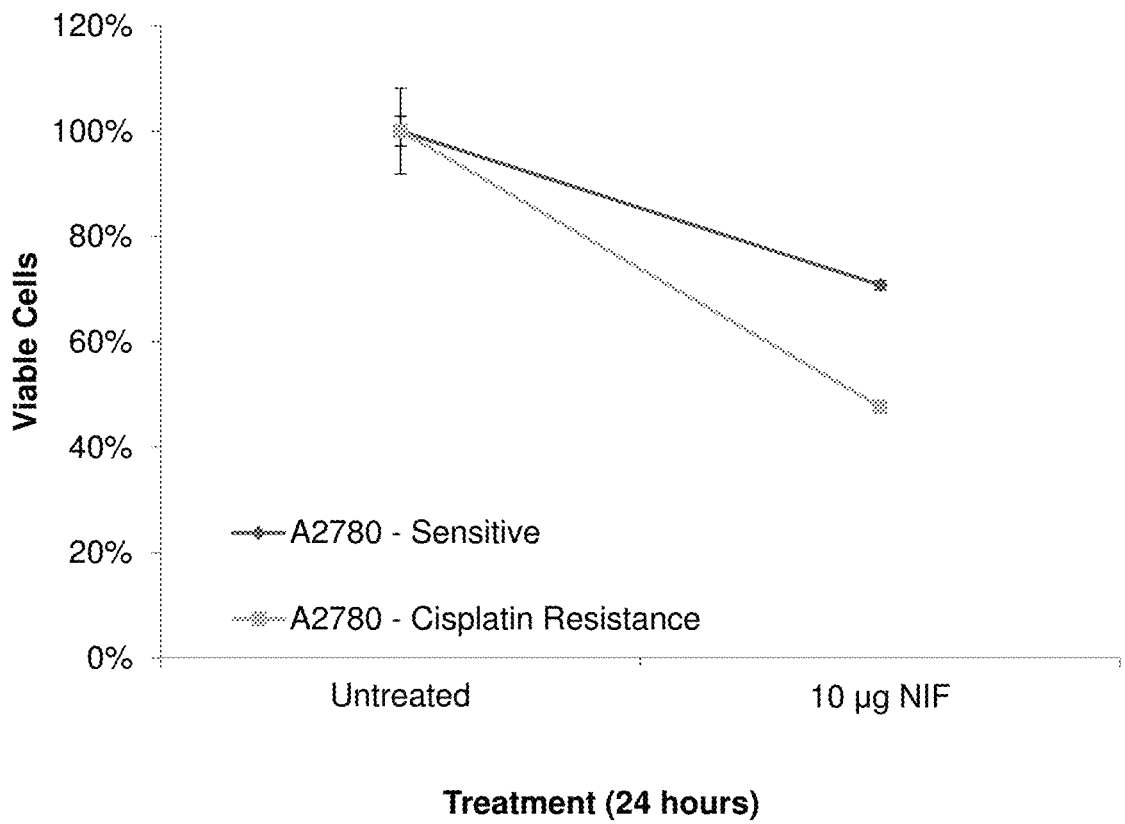
Figure 2A:
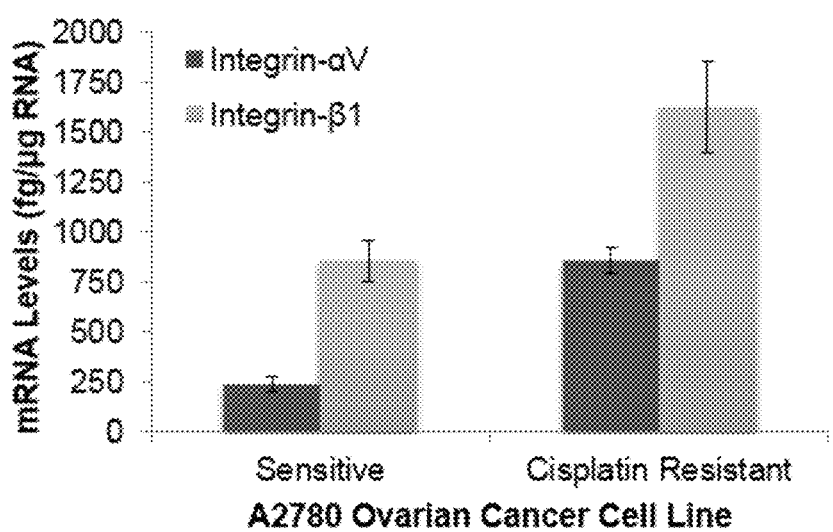
FIGS. 2A and 2B. Real-time RT-PCR and Western Blot analysis of integrin αV and integrin β1 levels in (FIG. 2A) A2780 sensitive and (FIG. 2B) Cisplatin resistant EOC cells.
Figure 2B:
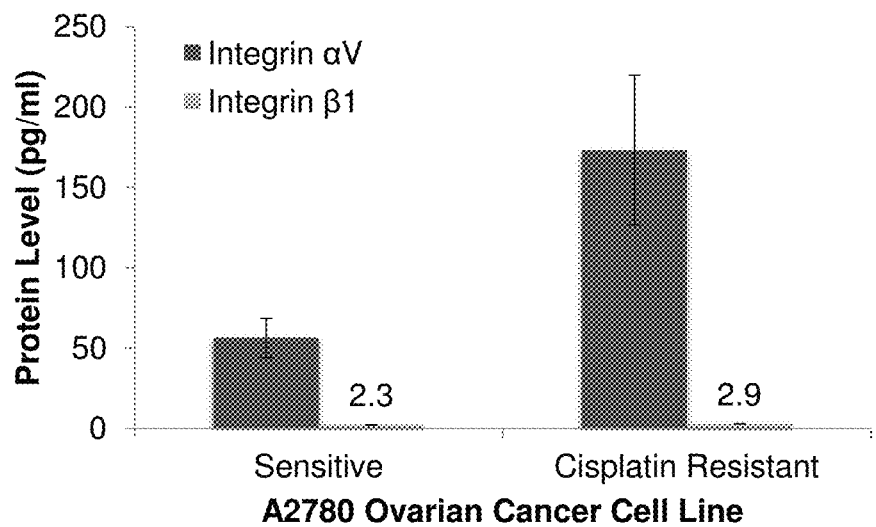
Figure 3A:
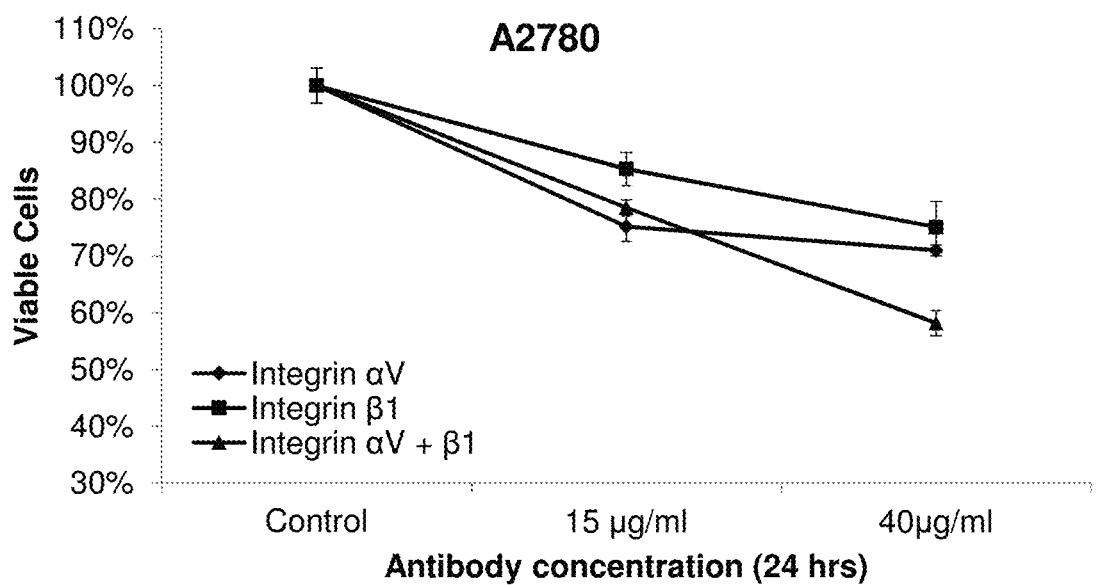
FIGS. 3A-3E. Cell viability in A2780 sensitive and cisplatin resistant EOC cells after treatment with integrin αV and integrin β1 antibody.
Figure 3B:
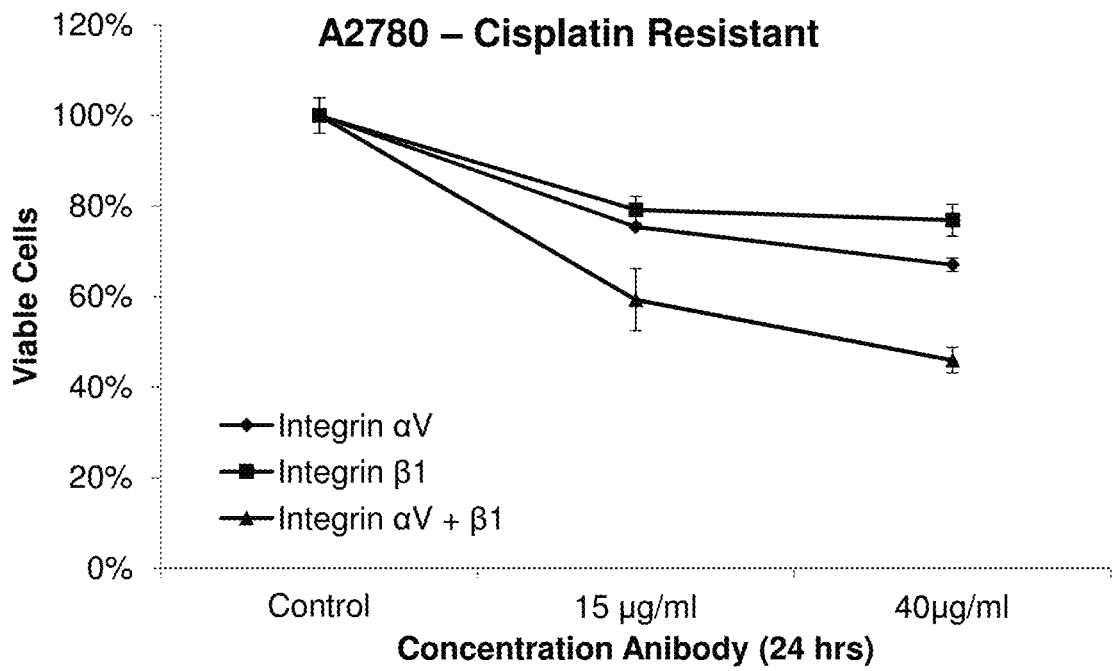
Figure 3C:
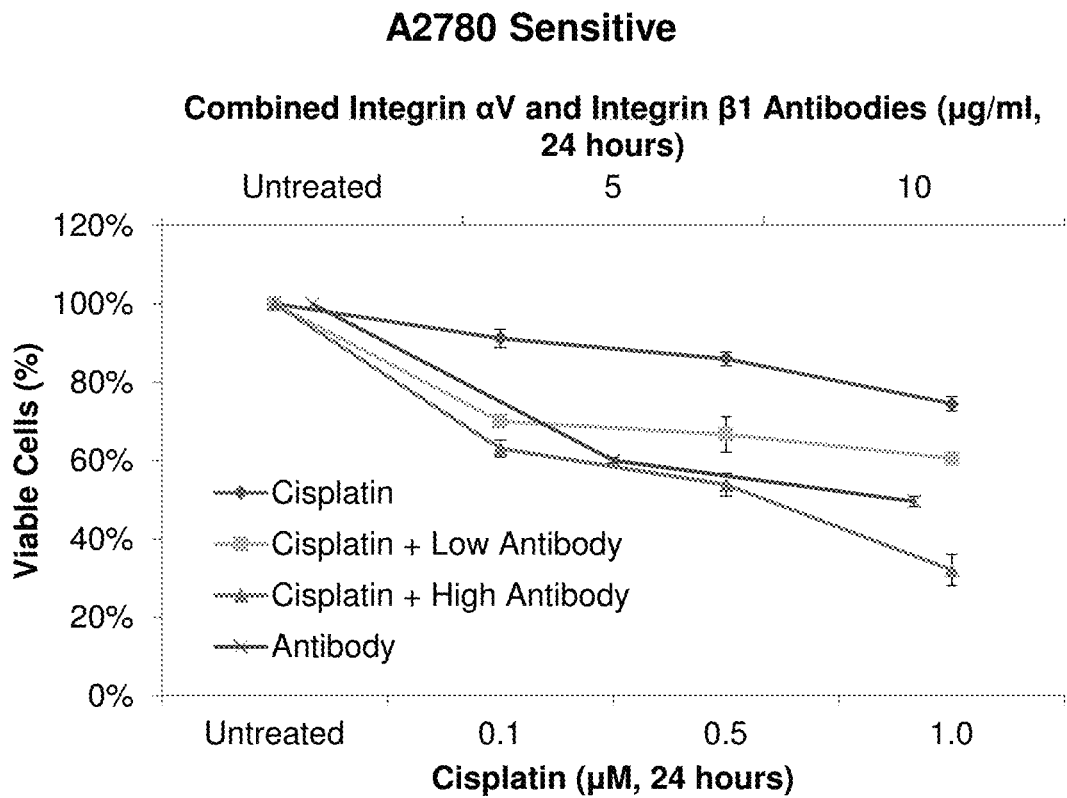
Figure 3D:
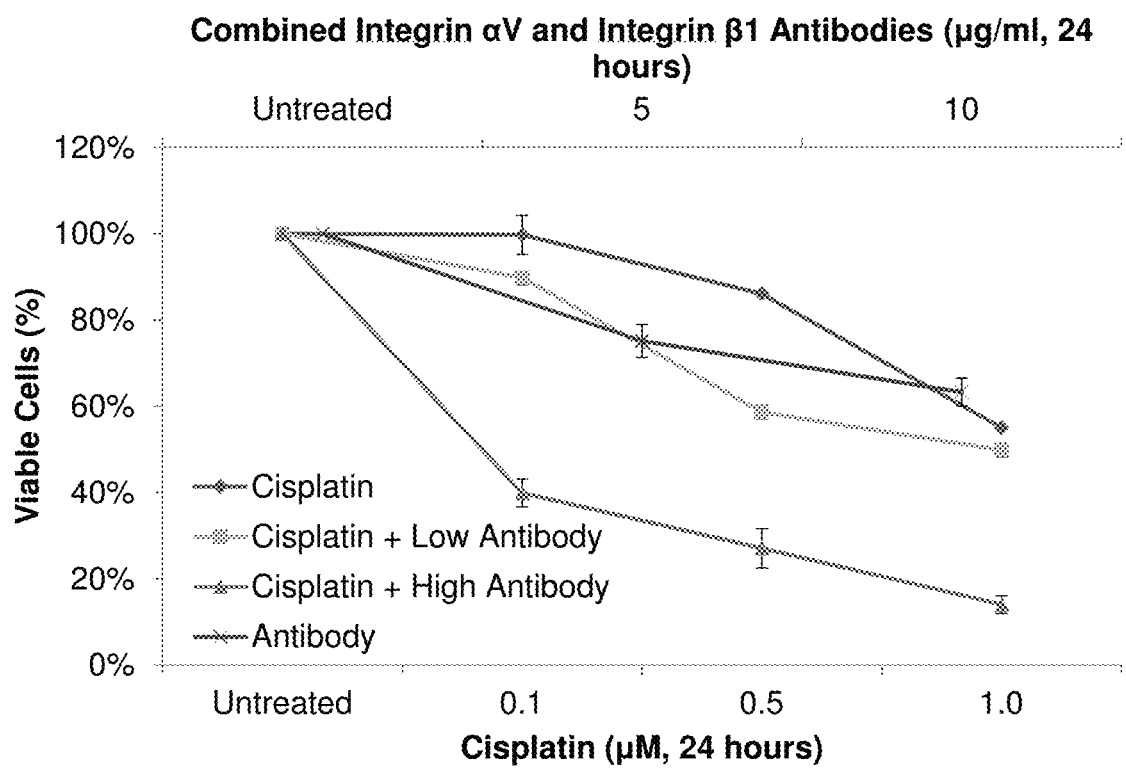
Figure 3E:
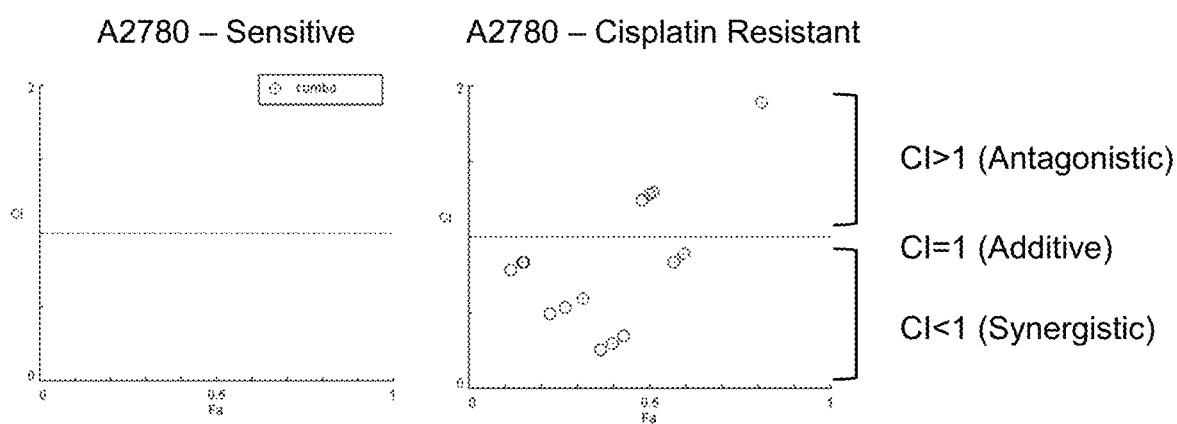
Figure 4A:
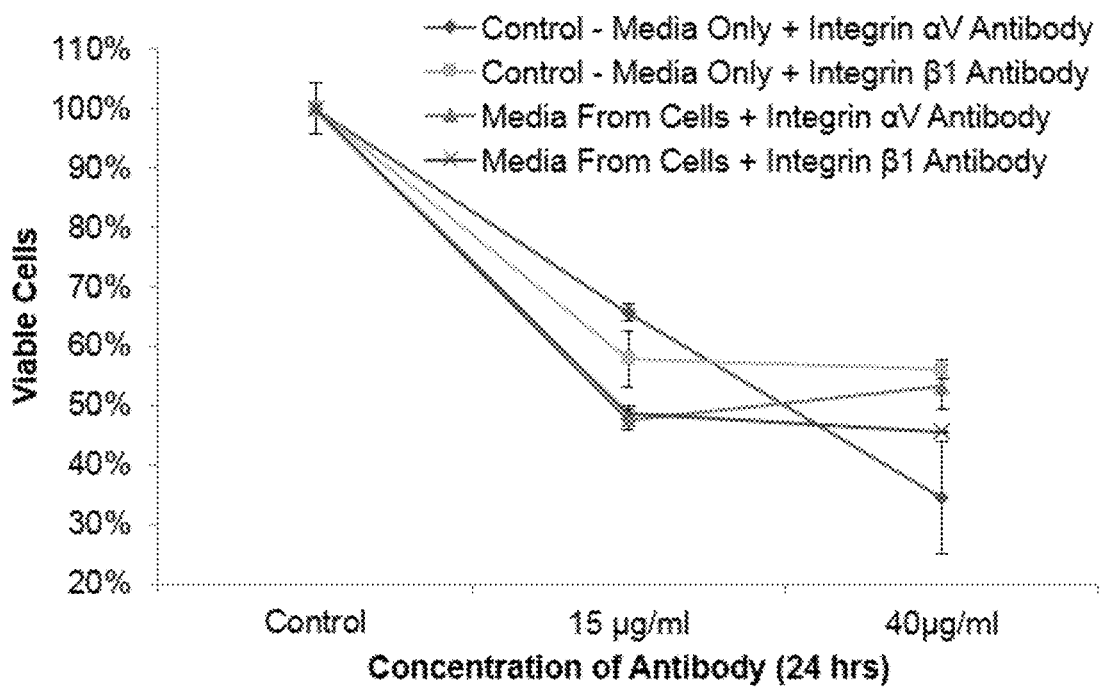
FIGS. 4A and 4B. Integrin αV and integrin β1 antibodies cross-react with a potential soluble target in EOC cell media. To test whether media collected from A2780 EOC cells contains a target that cross-reacts with the integrin αV or integrin β1 monoclonal antibodies, cells were cultured for 48 hours followed by removal of media. Either mouse anti-integrin αV or mouse anti-integrin β1 antibody was incubated with the conditioned cell culture media for 24 hours to block the antibody with the unknown target. The blocked antibody media was used to treat A2780 sensitive (FIG. 4A) or cisplatin resistant (FIG. 4B) EOC cells for another 24 hours followed by assessment of viability by the TACS MTT Cell Proliferation Assay. No decrease in cell viability was observed when treating with media containing "blocked" antibody in cisplatin resistant cells and in sensitive cells, but to a much lesser extent.
Figure 4B:
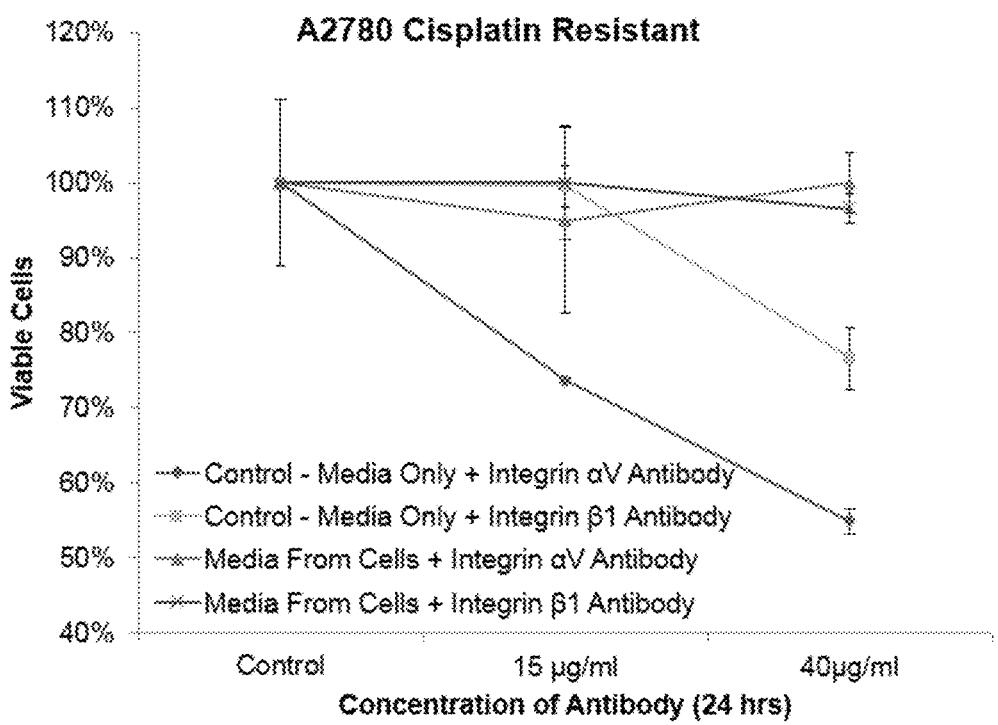

In this Example, Abciximab was tested in normal human macrophages and HOSEpiC cells, sensitive EOC cell lines (A2780, MDAH-2774, SKOV-3, OV90, TOV21G, OV112D, OV433, and HTB-161) and their Taxotere or Cisplatin resistant counterparts, and other cancer cell lines including colon (HTB-37), endometrial (CRL-1671), lung (CCL-257), prostate (CRL-1740), bladder (HTB-4), and hepatocellular (HB-8065) cancers, in vitro. The anti-cancer activity was significant in as compared to non-cancer (FIG. 1A). There was a synergistic effect when Abciximab was combined with cisplatin in sensitive A2780 cells (FIGS. 1B-1D).

Example 2

Cell Viability was Determined Using the TACS MTT Cell Proliferation Assay (Trevigen, Gaithersburg, Md.) per the manufacturer's protocol. Briefly, measurement of cell proliferation is based upon the reduction of the tetrazolium salt, 3,[4,5-dimethytthiazol-2-yl]-2,5-diphenyl-tetrazolium bromide (MTT). MTT is reduced to an insoluble formazan dye by mitochondrial enzymes associated with metabolic activity of living cells. A standard curve was constructed using each respective cell line using a two-fold dilution series. Cells were seeded into 96-well plates in a fixed volume of 100 μl at a density of 8000 cells/well. Cells were treated with integrin αV or integrin β1, alone or in combination (0, 15, and 40 μg/ml) for 24 hours. Following incubation, 10 μl of the MTT solution was added to each well and incubated for 2 hours followed by the addition of 100 μl of the Detergent Solution to each well and incubation for an additional 2-4 hours. Absorbance was measured at 570 nm. A blank containing only medium was subtracted from all test samples.

RNA Isolation and Reverse Transcription of cDNA, for Real-Time RT-PCR.

RNA isolation. Total RNA was extracted from cells using the RNeasy Mini Kit (Qiagen, Valencia, Calif.) according to the manufacturer's protocol and as previously reported in Eldh et al., Mol. Immunol., 2012. 50(4): p. 278-86.

Reverse Transcription and Real-Time RT-PCR.

Reverse transcription: A 20 μL cDNA reaction volume containing 1 μg RNA was prepared using the SuperScript VILO Master Mix Kit (Life Technologies, Grand Island, N.Y.), as described by the manufacturer's protocol.

Real-Time RT-PCR Primer Design and Controls:

Optimal oligonucleotide primer pairs for real-time RT-PCR amplification of reverse-transcribed cDNA were selected with the aid of the software program, Beacon Designer (Premier Biosoft Int., Palo Alto, Calif.). Human oligonucleotide primers, which amplify variable portions of the protein coding regions, were used. Sequences of the oligonucleotides used for amplification of β-actin, CD1 b, MPO, integrin αV and integrin β1 mRNA are as described in Table 1 of FIG. 23.

Quantitative RT-PCR was performed using the EXPRESS SYBR GreenER qPCR Supermix Kit (Life Technologies) and the Cepheid 1.2f Detection System. Real-time RT-PCR was performed in a 25 μl total reaction volume including 12.5 μl of EXPRESS SYBR GreenER qPCR Supermix, 1 μl of cDNA template, and 0.2 μM each of target specific primers designed to amplify a part of each gene. Standards with known concentrations and lengths (base pairs (bp))

were designed specifically for each gene using the Beacon Designer software (Premier Biosoft, Palo Alto, Calif.), allowing for construction of a standard curve using a tenfold dilution series. A specific standard for each gene allows for absolute quantification of the gene in number of copies, which can then be expressed per pg of RNA. Following real-time RT-PCR, a melting curve analysis was performed to demonstrate the specificity of the PCR product as a single peak. Samples were all normalized to A-actin. A control, containing all the reaction components except for the template was included in all experiments. All experiments were performed in triplicate.

Results.

Cisplatin resistant A2780 cells have higher mRNA and protein levels of integrin αV and higher mRNA levels of integrin β1 as compared to their chemosensitive counterparts. Treatment with antibodies integrin αV or integrin β1 alone lead to a decrease in cell viability in a dose dependent manner. A combination of both antibodies lead to a further decrease in viability in both sensitive and chemoresistant cell lines.

Example 3. MPO

Figure 5:
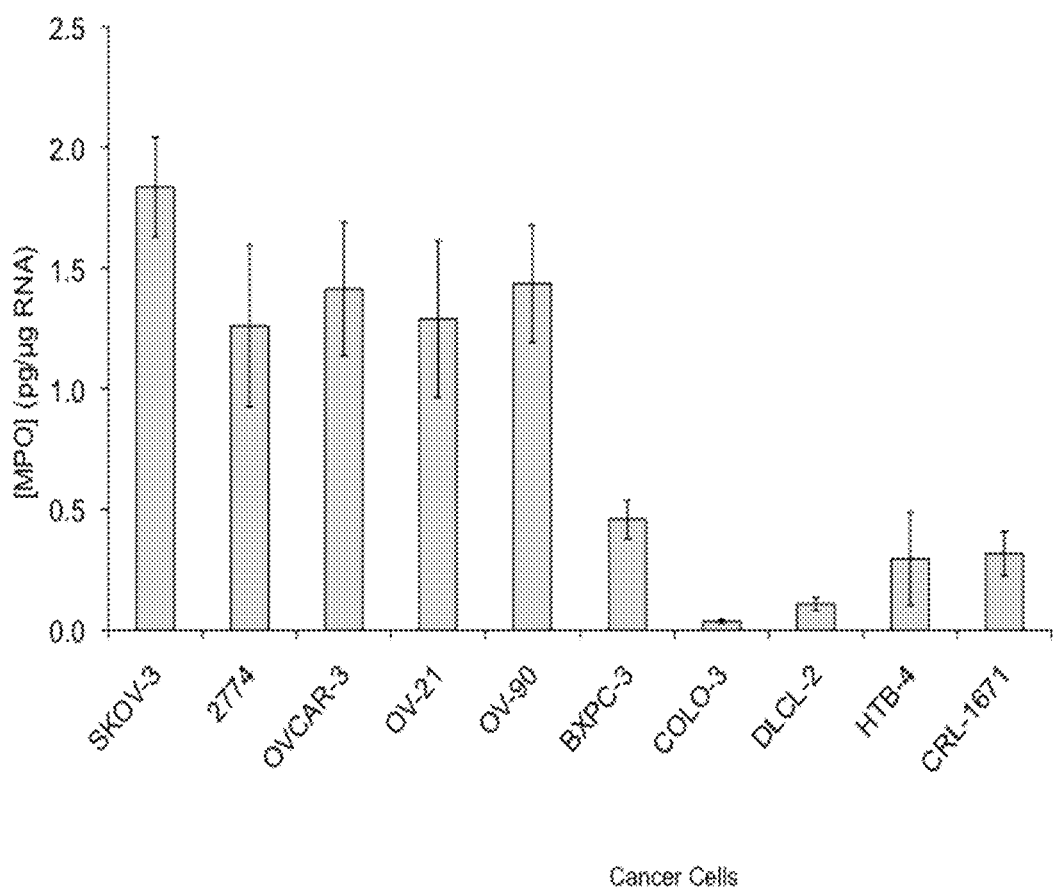
FIG. 5. Real-time RT-PCR analysis of MPO in multiple cancer cell lines. MPO mRNA level was determined in epithelial ovarian cancer (EOC) (SKOV-3, MDAH-2774, OVCAR-3, OV-21, OV-90), pancreatic cancer (BXPC-3), colon cancer (COLO-3), non-Hodgkin's B cell lymphoma (DLCL-2), bladder cancer (HTB-4), and endometrial cancer (CRL-1671) cell lines.
Figure 6:
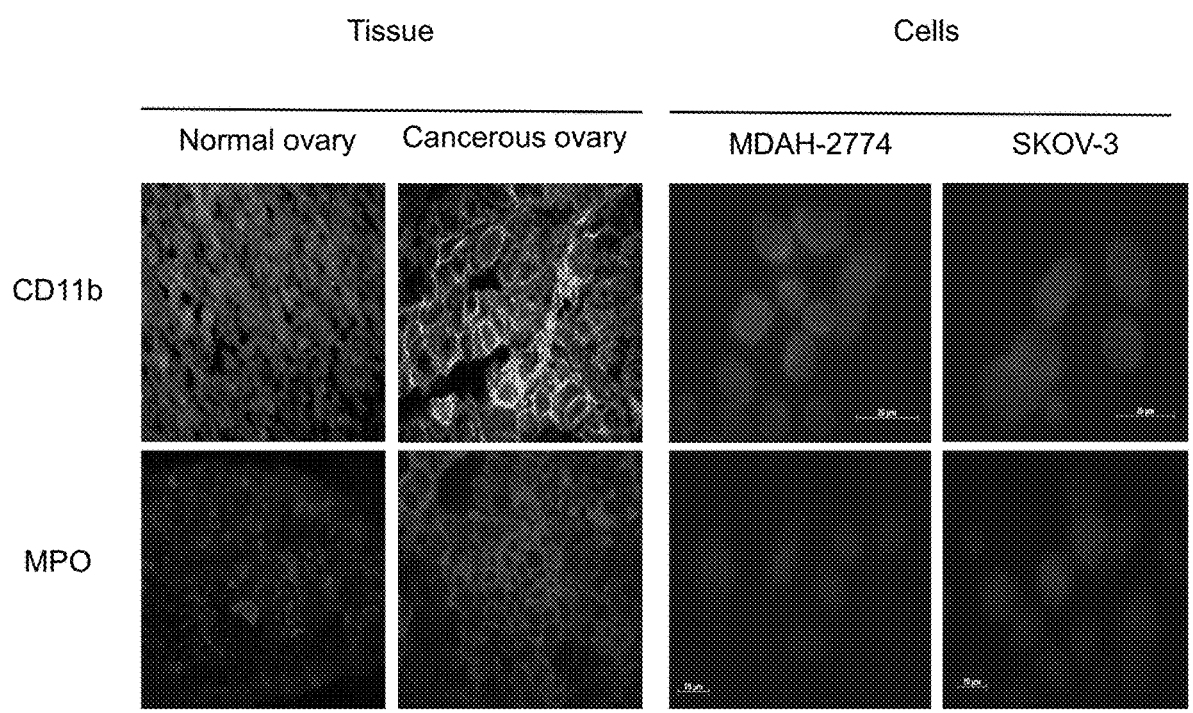
FIG. 6. Immunofluorescence detection of CD11b or MPO in normal ovarian tissue and ovarian cancer tissues and cells. Normal ovarian tissues, cancerous ovarian tissues, and ovarian cancer cells (MDAH-2774 and SKOV-3) were immunofluorescently stained for either CD11b or MPO.
Figure 7A:
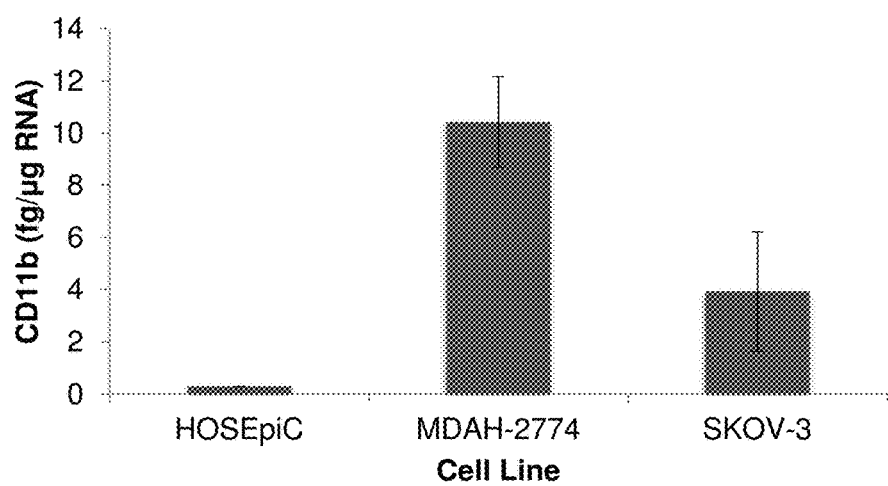
FIGS. 7A and 7B. Real-time RT-PCR analysis of CD11b and MPO in cells.
Figure 7B:
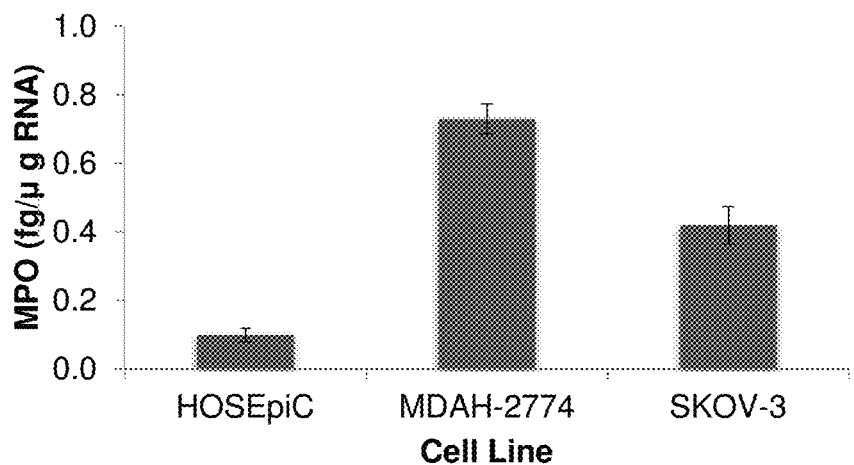
Figure 8:
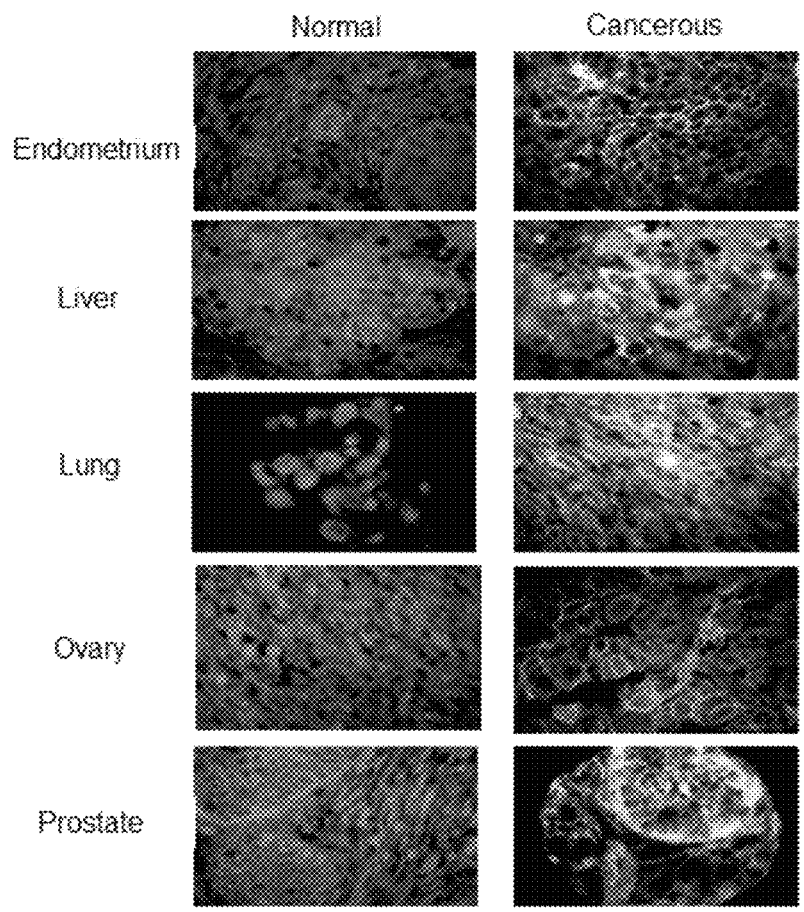
FIG. 8. CD11b expression in normal and cancerous tissues. Tissue sections were incubated with the FITC-conjugated antibody (mouse anti-CD11b monoclonal antibody; Santa Cruz Biotechnology) diluted at 1:100 ratio for 1 hour at room temperature followed by visualization with the Axiovert 25 inverted microscope (Zeiss).
Figure 9:
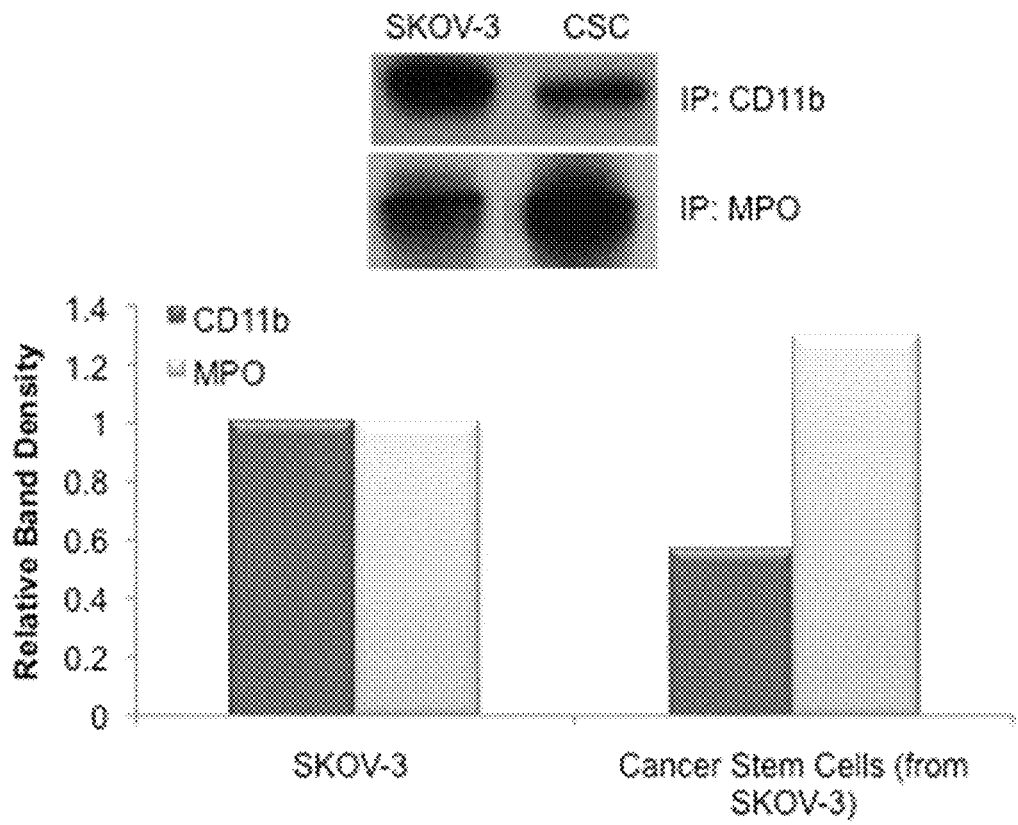
FIG. 9. CD11b and MPO expression in cancer stem-like cells isolated from the EOC cell line, SKOV-3. Isolation of CSCs was achieved utilizing the magnetic-activated cell sorting technique for CD44+CD117+ cells via a CD44 or CD117 antibody coupled to magnetic beads. Lysates from cells was then immunoprecipitated for either CD11b or MPO, and protein was separated by SDS PAGE/Western blot and transferred to PVDF membrane. Protein was probed with either CD11b or MPO antibody. Bands were analyzed with Image J and are relative to SKOV-3 bands.
Figure 10A:
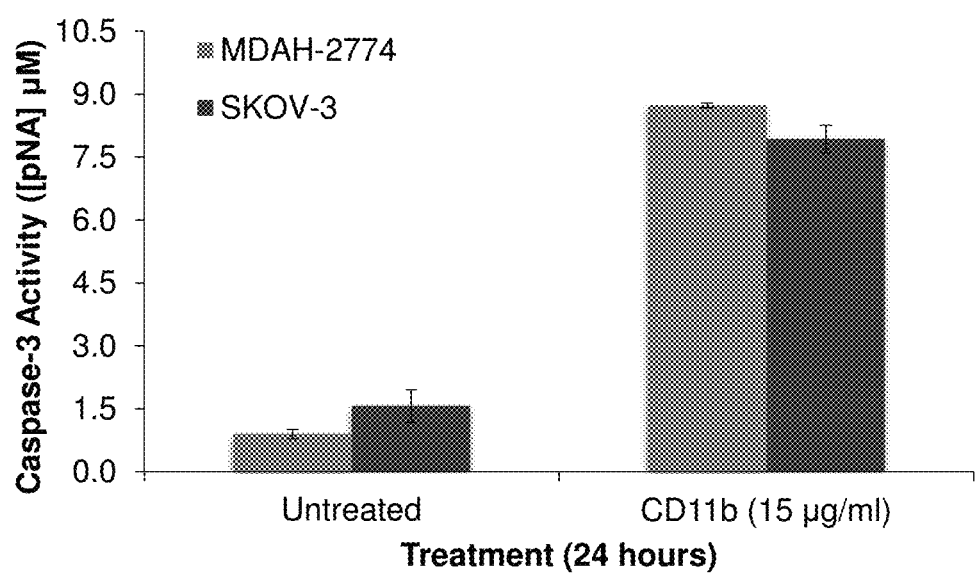
FIGS. 10A and 10B. CD11b antibody increases apoptosis in EOC cells. Two EOC cell lines, MDAH-2774 and SKOV-3, were treated for 24 hours with CD11b antibody (15 µg/ml).
Figure 10B:
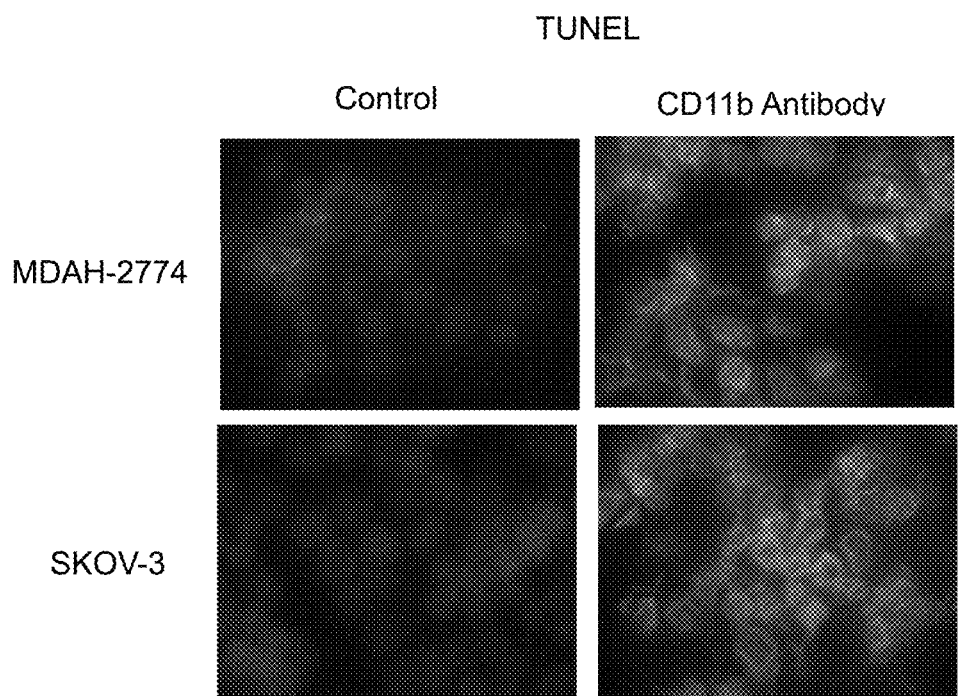
Figure 11:
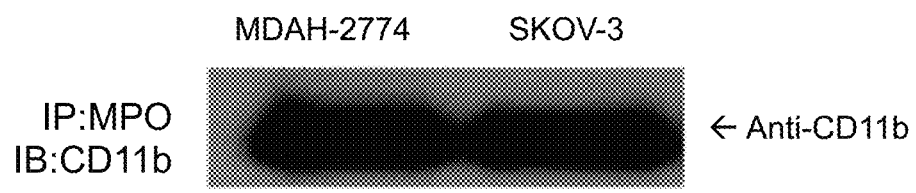
FIG. 11. MPO antibody binds to CD11b in ovarian cancer cells. Cell lysates from either MDAH-2774 or SKOV-3 EOC cells were immunoprecipitated with MPO antibody. The proteins were separated by SDS PAGE/Western blot and transferred to a PVDF membrane. The membrane was probed with anti-CD11b antibody.

MPO expression may be unique to EOC cells, as it was not detected in several other types of cancer cell lines (FIG. 5). These include the ovarian cancer cell lines of SKOV-3 and MDAH-2774. Moreover, MPO expression was not detectable in normal ovarian tissues (published). Immunoreactivity showed a striking increase in both CD11b and MPO in ovarian cancer tissues as compared to normal ovarian tissues (FIG. 6). The presence of CD11b and MPO was also confirmed in EOC cells (FIG. 6). Additionally, further confirmation of the expression of both MPO and CD11b was determined in HOSEpiC as compared to EOC cells MDAH-2774 and SKOV-3 (FIGS. 7A and 7B). Additionally, CD11b is present in several different cancer cell tissues (FIG. 8). Utilizing CD44 and CD117 antibody-conjugated magnetic beads, cancer stem-like cells (CSCs) were isolated from the EOC cell line, SKOV-3. These CSCs were found to express both lower levels of CD11b and higher levels of MPO as compared to SKOV-3 EOC cells. Without being bound by theory, it is believed that when differentiated cancer cells die, they release cytokines and other components that make the cancer stem like cells differentiate into mature cells, likely with aberrant genes and DNA/RNA/protein expression and expression levels. CD11b antibody caused apoptosis in cells (FIGS. 10A and 10B). This was determined by TUNEL assay, which detects damaged DNA and indicates apoptosis, as well as by an increase in caspase-3 activity which correlates with increased apoptosis (FIGS. 10A and 10B).

Figure 12:
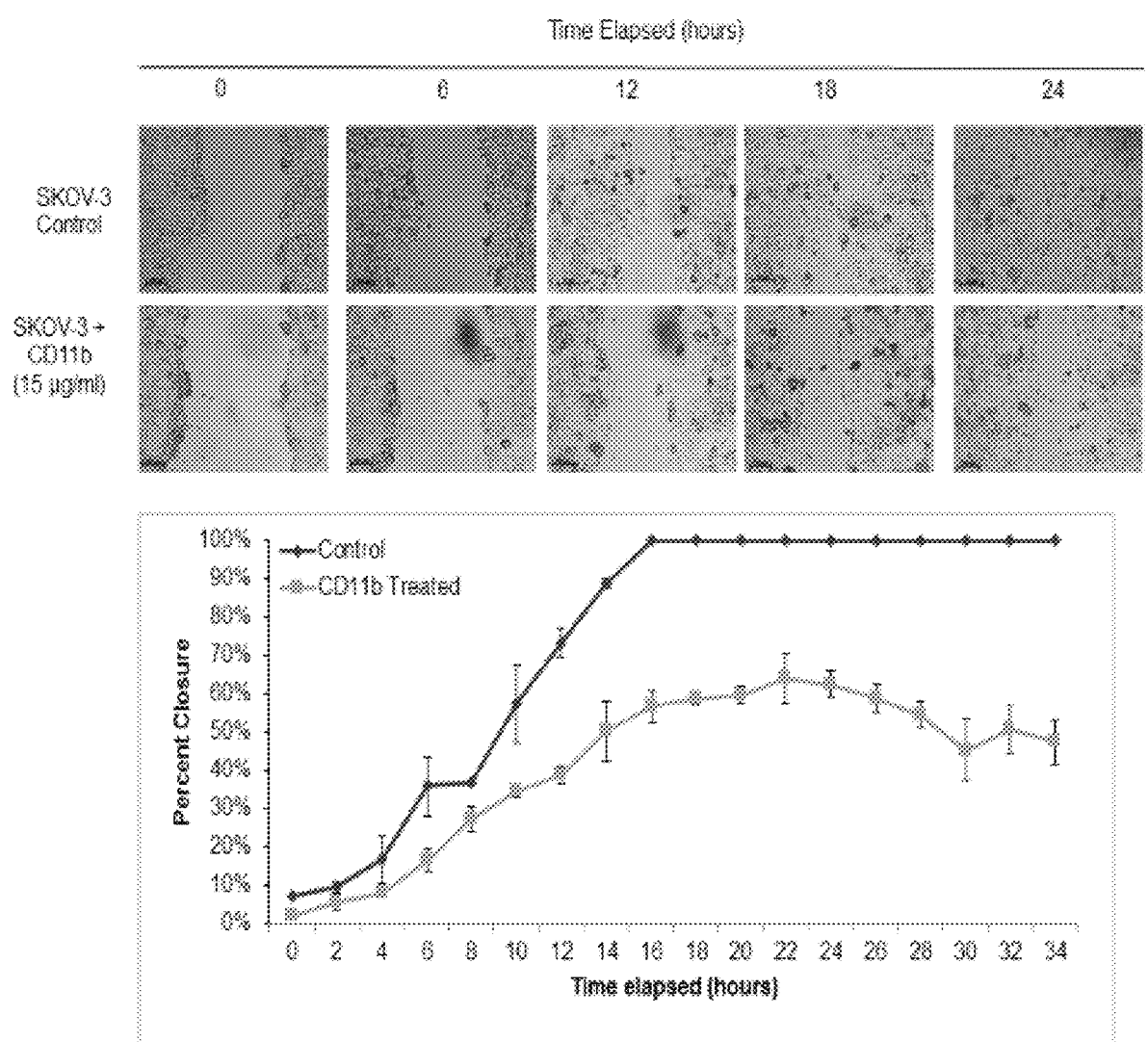
FIG. 12. Scratch assay to determine inhibition of migration of EOC cells. Phase-contrast optical images of the SKOV-3 EOC cell line at 0, 6, and 12, 18, and 24 hours after the creation of a cell-free zone using the scratch technique. At time 0, there was a 1 mm wide cell free zone obtained utilizing a pipette tip to scratch away adherent SKOV-3 EOC cells. Treatment with CD11b antibody resulted in a significantly slower rate of migration of the EOC cells and eventual cell death around 24 hours.

Adding antibodies to cell cultures cause apoptosis in cells in the low micromolar range. On a scratch assay, the control cells grew back into the scratch groove until contact inhibition was reestablished (FIG. 12). Those cells treated with the CD11b antibody did not grow back into the groove. Further, the cells that were not part of the scratch started to die off, even at the low micromolar range (FIG. 12).

Figure 13:
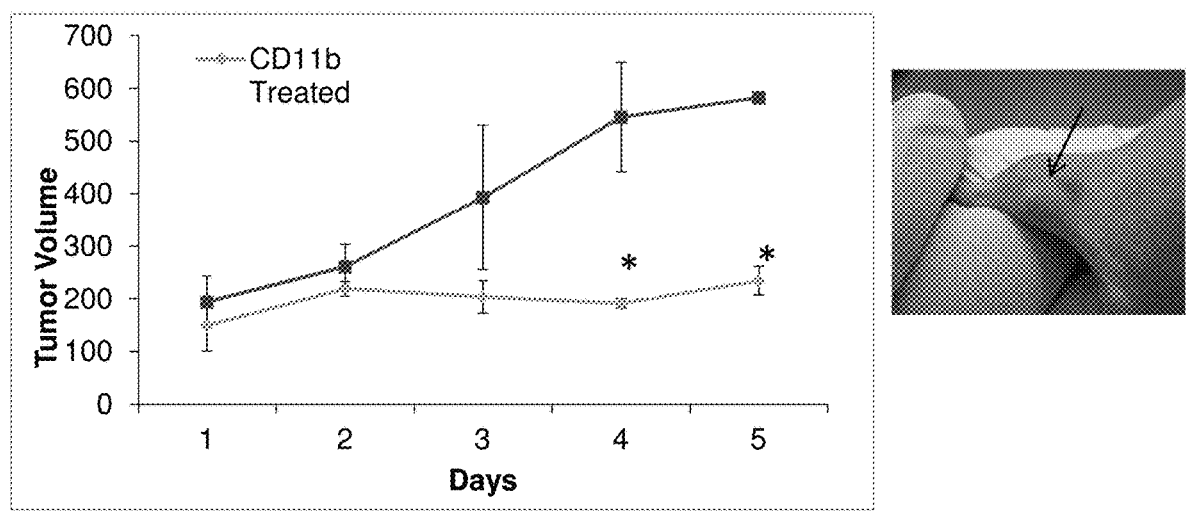
FIG. 13. Treatment with CD11b antibody prevented an increase in tumor volume in athymic NUDE mice. Control (n=2) and treated mice (n=2) obtained from Harlan were subcutaneously injected on each flank with saline or a single-cell suspension of the human ovarian cancer cell line SKOV-3 using a 21 gauge needle. Once the tumor was visible, mice were injected daily with 0.12 ml of CD11b antibody into the tumor and tumor measurement were taken daily for 5 days. Tumor weights were calculated as Tumor weight (mg)=(A×B2)/2, where A and B are the tumor length and width (in mm), respectively.
Figure 14A:
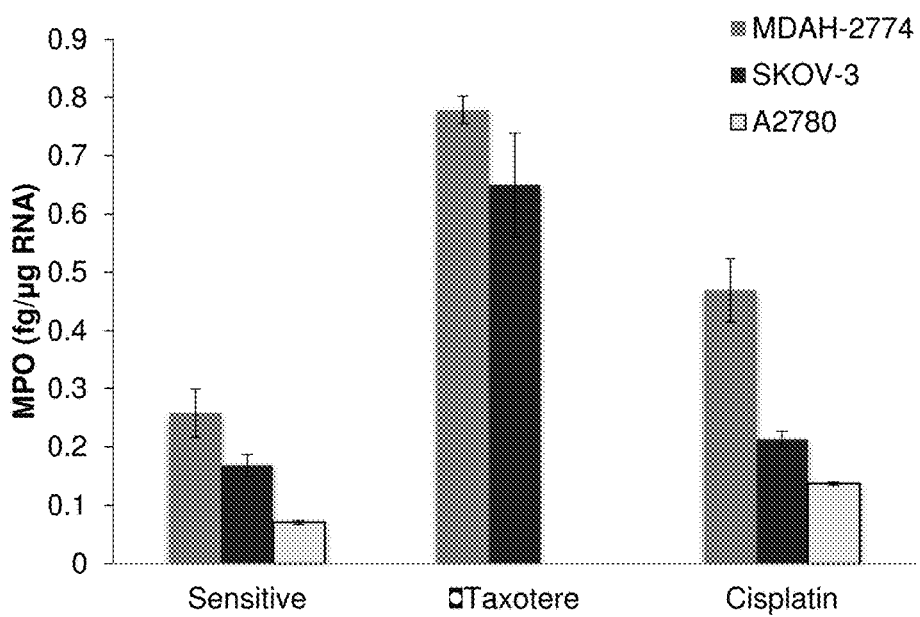
FIGS. 14A-14E. Real-time RT-PCR and Immunoprecipitation/Western Blot analysis of CD11b, CD18 and MPO in sensitive as compared to chemoresistant EOC cells. Chemoresistant EOC cell lines (0.3 µM Taxotere (Tx) or 1.5 µM cisplatin (cis)) and their chemosensitive (sens) counterparts were utilized to determine (FIG. 14A) MPO mRNA and (FIG. 14B) protein levels. Chemoresistant EOC cell lines and their chemosensitive counterparts were also utilized to determine CD11b (FIG. 14C) mRNA and (FIG. 14D) protein levels, as well as (FIG. 14E) CD18 mRNA levels.
Figure 14B:
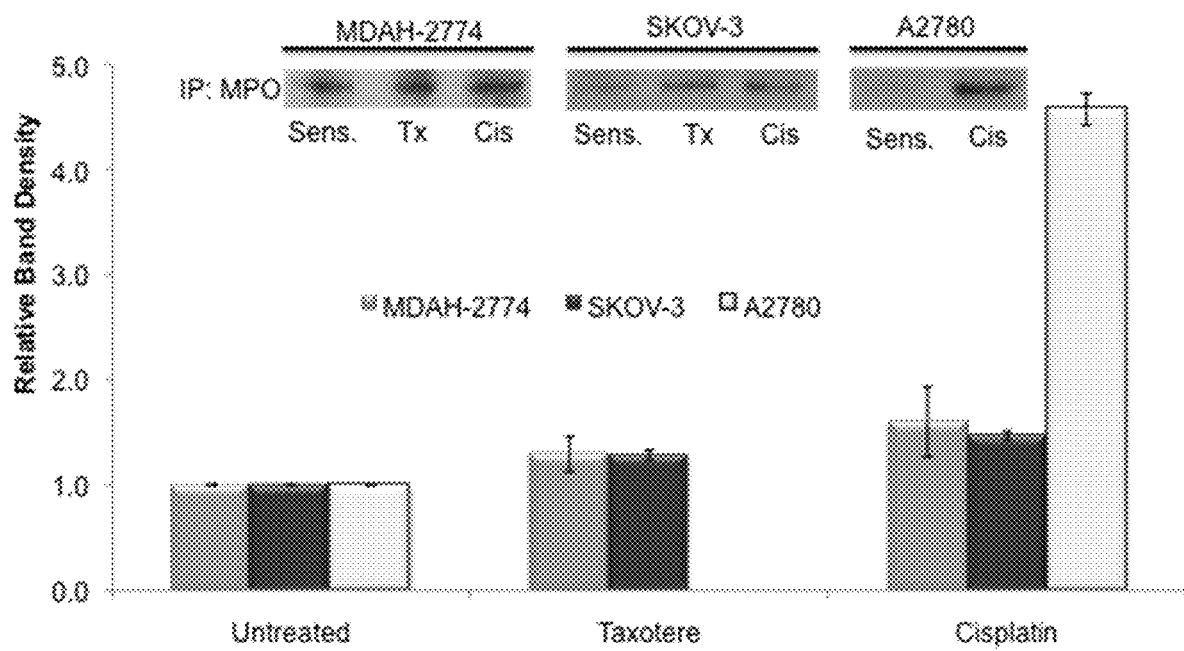
Figure 14C:
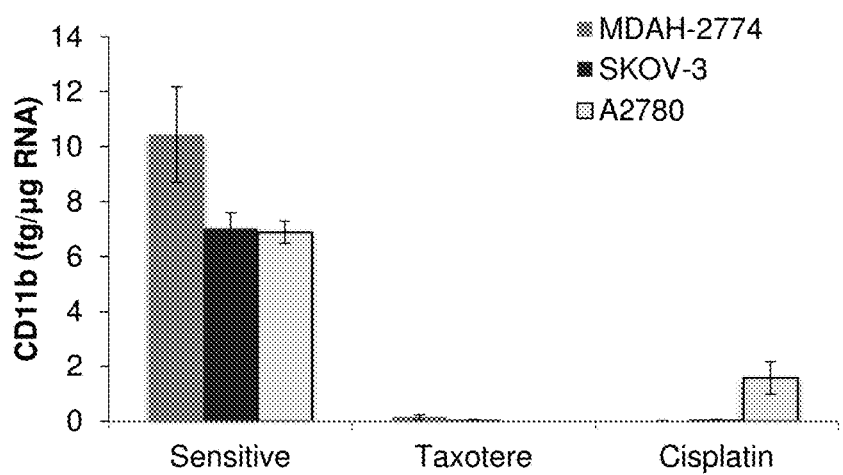
Figure 14D:
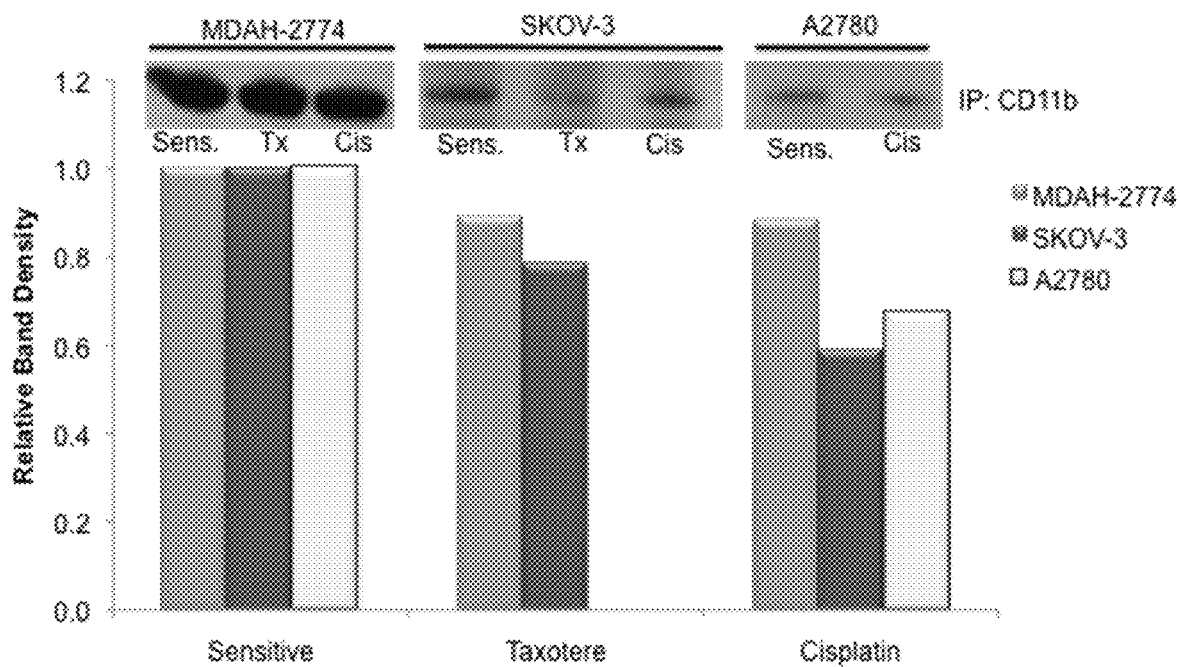
Figure 14E:
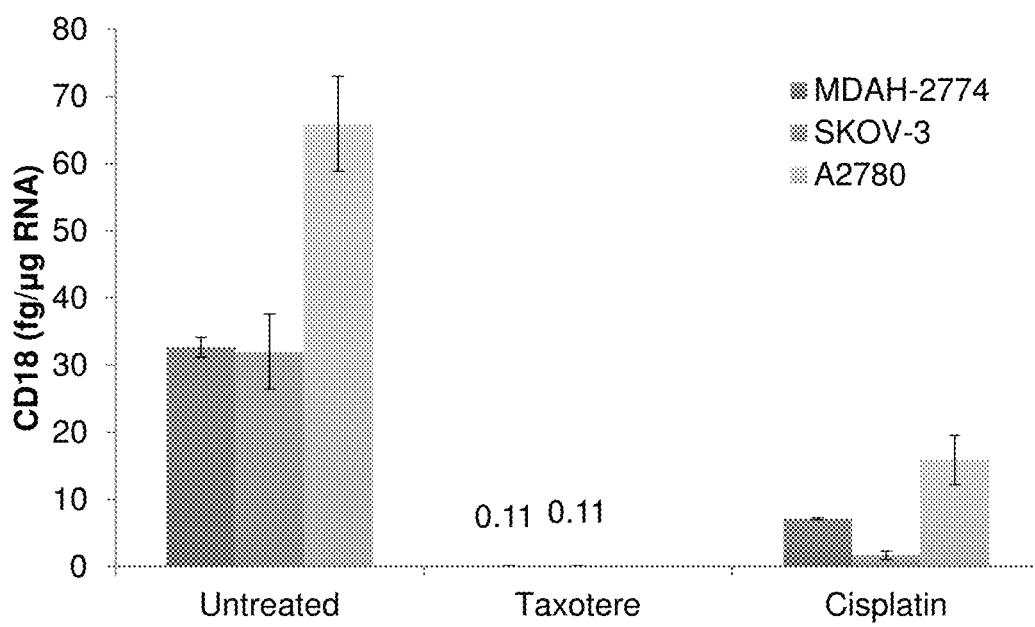

Animal Studies:

Growth of xenograph implants of SKOV-3 cells in athymic nude mice were significantly delayed when tumors were injected with CD11b antibody (FIG. 13). CD11b drastically decreases while MPO increases in all of the chemoresistant as compared to sensitive EOC cell lines tested (MDAH-2774, SKOV-3, A2780) (FIGS. 14A-14D). Additionally, CD18 expression is lower in chemoresistant EOC cells as compared to sensitive counterparts (FIG. 14E).

Figure 15A:
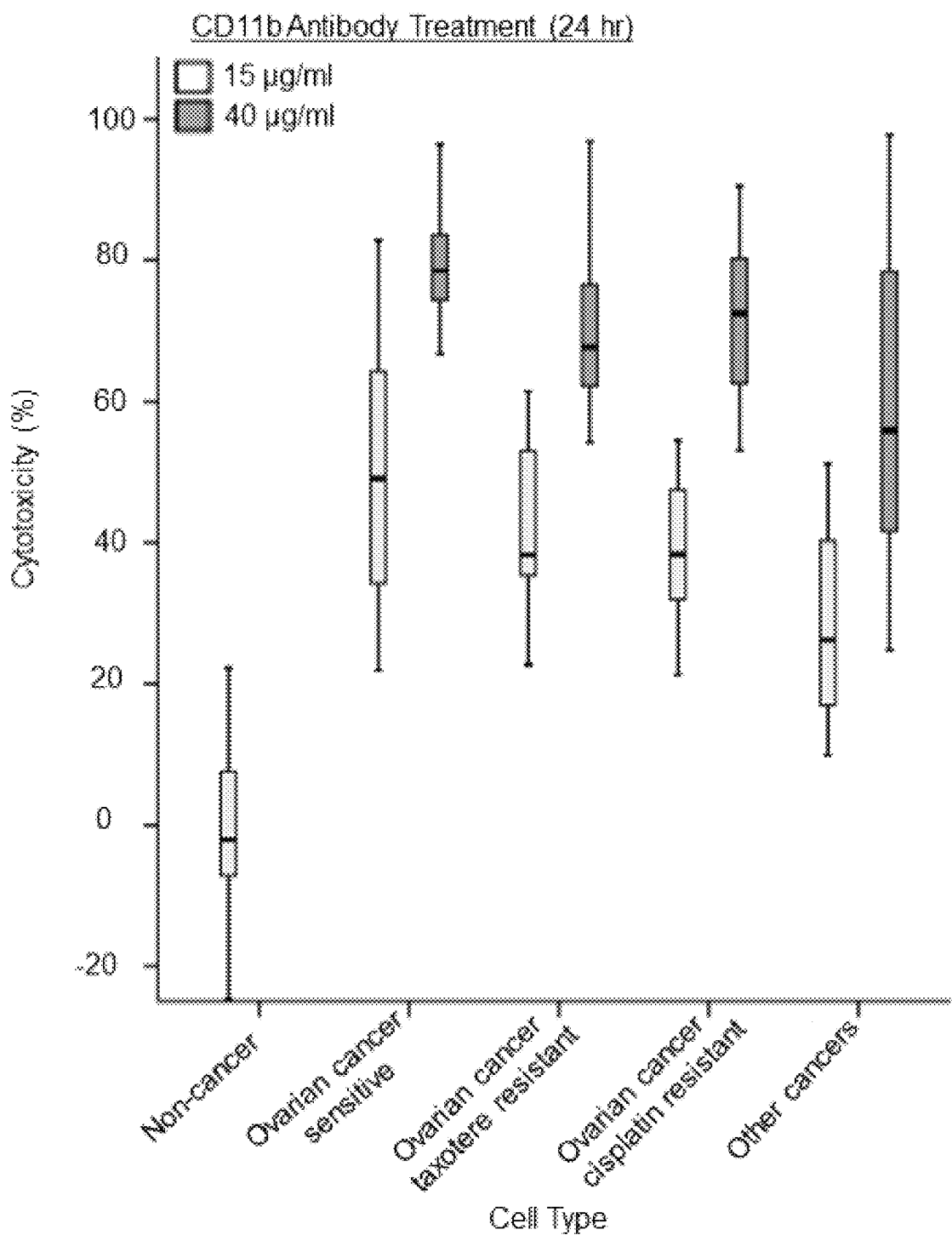
FIGS. 15A-15D. Anti-cancer effects of the CD11b antibody.
Figure 15B:
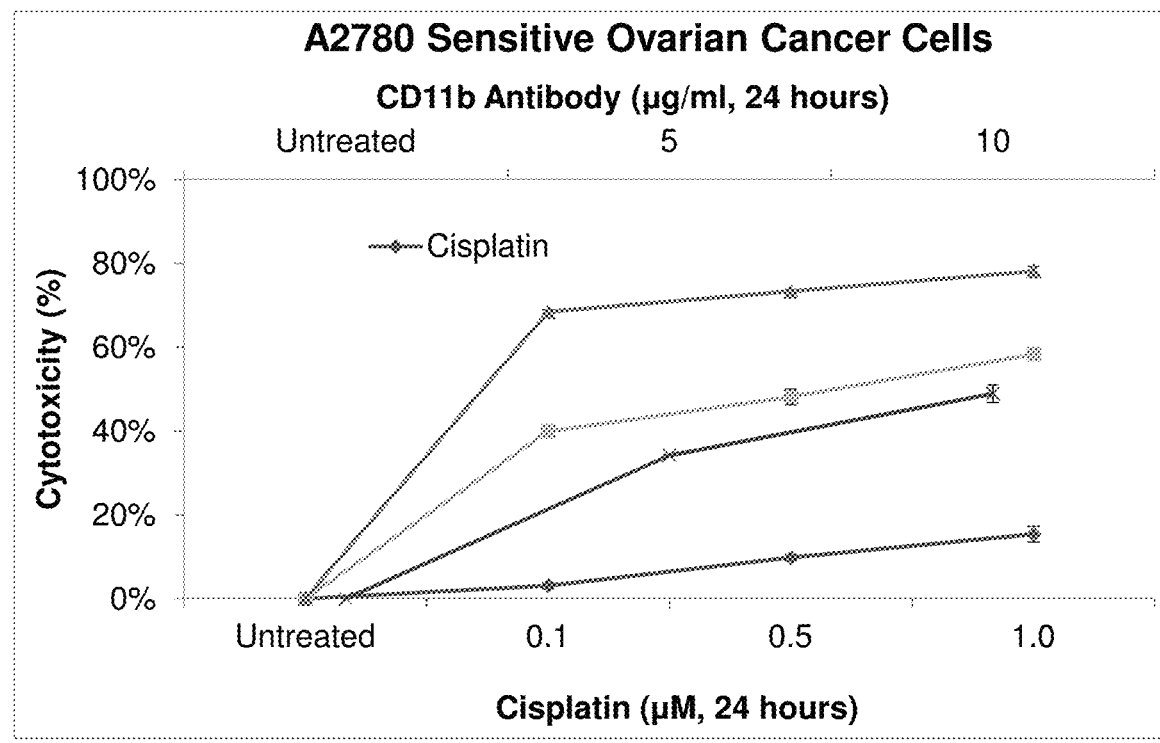
Figure 15C:
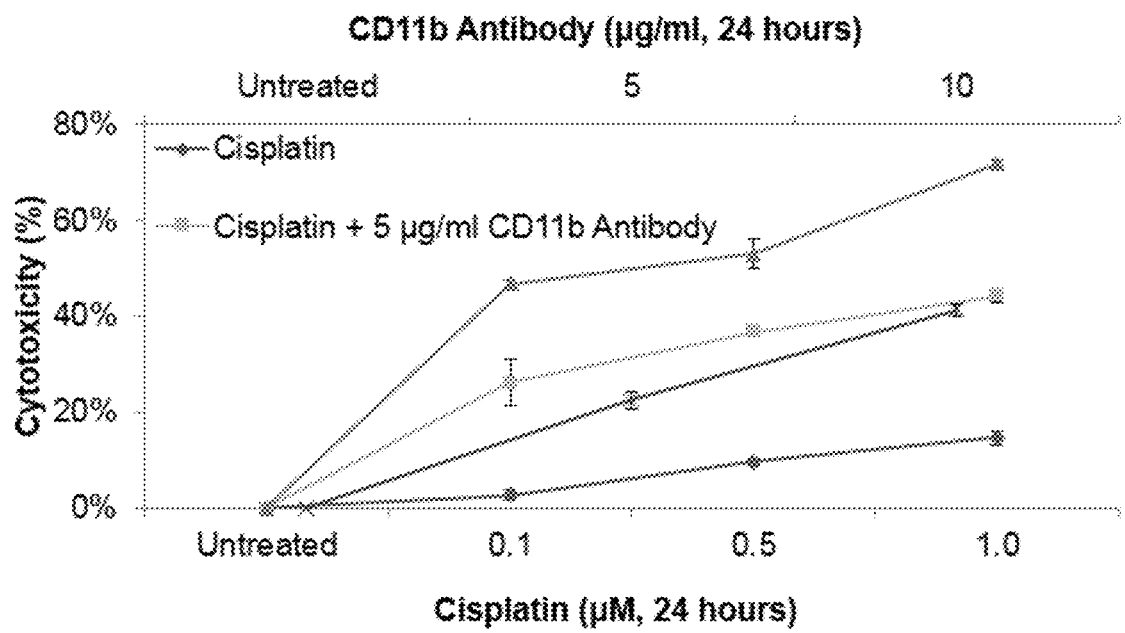
Figure 15D:
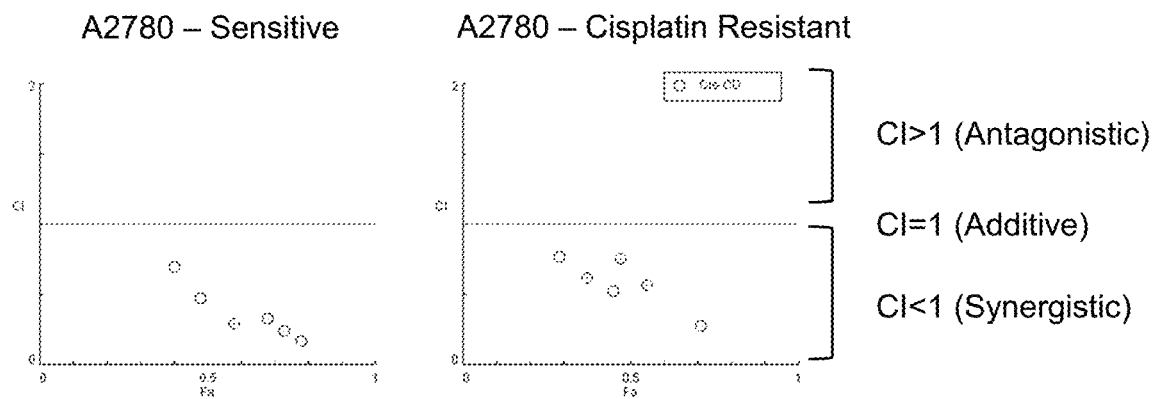
Figure 16:
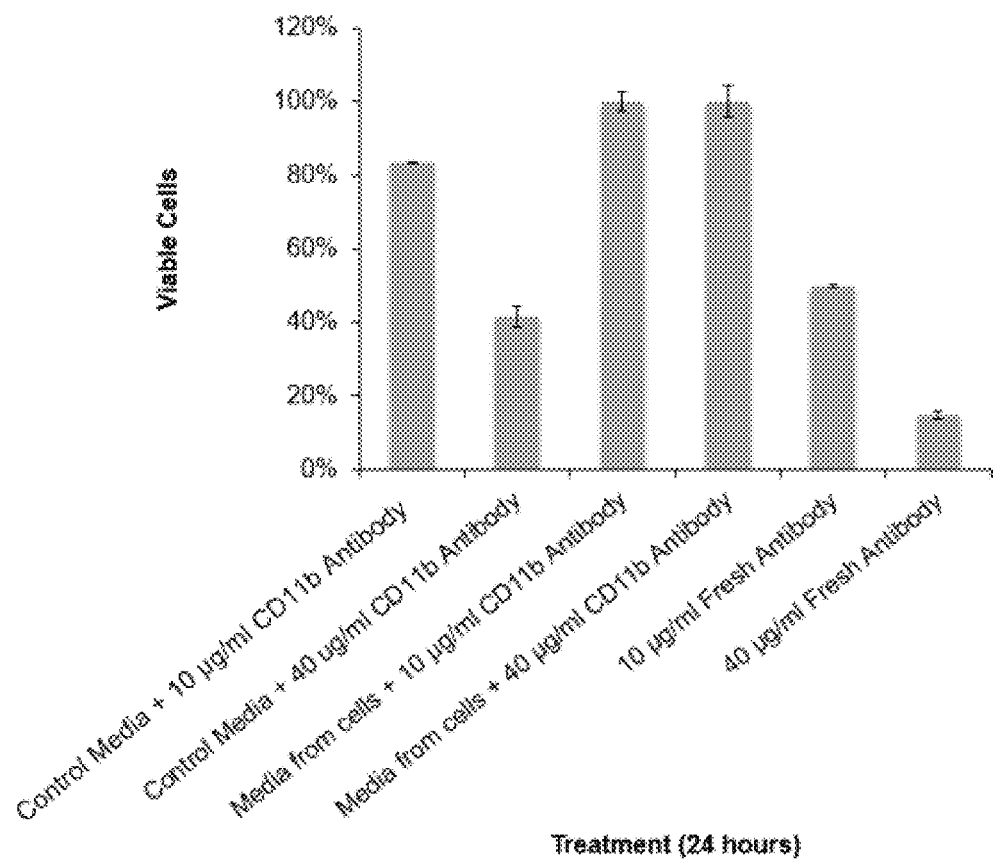
FIG. 16. CD11b antibody cross-reacts with a potential soluble target in EOC cell media. To test whether media collected from A2780 EOC cells contains a target that cross-reacts with the CD11b monoclonal antibody, cells were cultured for 48 hours followed by removal of media. The CD11b antibody was incubated with the conditioned cell culture media for 24 hours to block the antibody with the unknown target. The blocked antibody media was used to treat A2780 sensitive EOC cells for another 24 hours followed by assessment of viability by the TACS MTT Cell Proliferation Assay. No decrease in cell viability was observed when treating with media from cells containing "blocked" antibody.

Viability Assays:

Treatment with CD11b antibody (15 μg/ml, 24 hours) resulted in no change in cell viability in either normal cells such as HOSEpiC and macrophages (FIG. 15A). Treatment of sensitive EOC cell lines (A2780, MDAH-2774, SKOV-3, OV90, TOV21G, OV112D, OV433, and HTB-161) and their Taxotere or Cisplatin resistant counterparts with various doses of CD11b antibody resulted in a significant reduction in cell viability (FIG. 15A). Other types of cancer cell lines including colon (HTB-37), endometrial (CRL-1671), lung (CCL-257), prostate (CRL-1740), bladder (HTB-4), and hepatocellular (HB-8065) cancers also had a significant reduction in viability upon treatment with increasing doses of the CD11b antibody. Combination of the CD11b antibody with cisplatin treatment of sensitive and cisplatin resistant A2780 EOC cells resulted in a further increase in cytotoxicity and was observed to act in a synergistic fashion (FIGS. 15B-15D). To test whether media collected from A2780 EOC cells contains a target that cross-reacts with the CD11b monoclonal antibody, cells were cultured for 48 hours followed by removal of media. The CD11b antibody was incubated with the conditioned cell culture media for 24 hours to block the antibody with the unknown target. The blocked antibody media was used to treat A2780 sensitive EOC cells for another 24 hours followed by assessment of viability by the TACS MTT Cell Proliferation Assay. No decrease in cell viability was observed when treating with media from cells containing "blocked" antibody (FIG. 16).

Figure 17A:
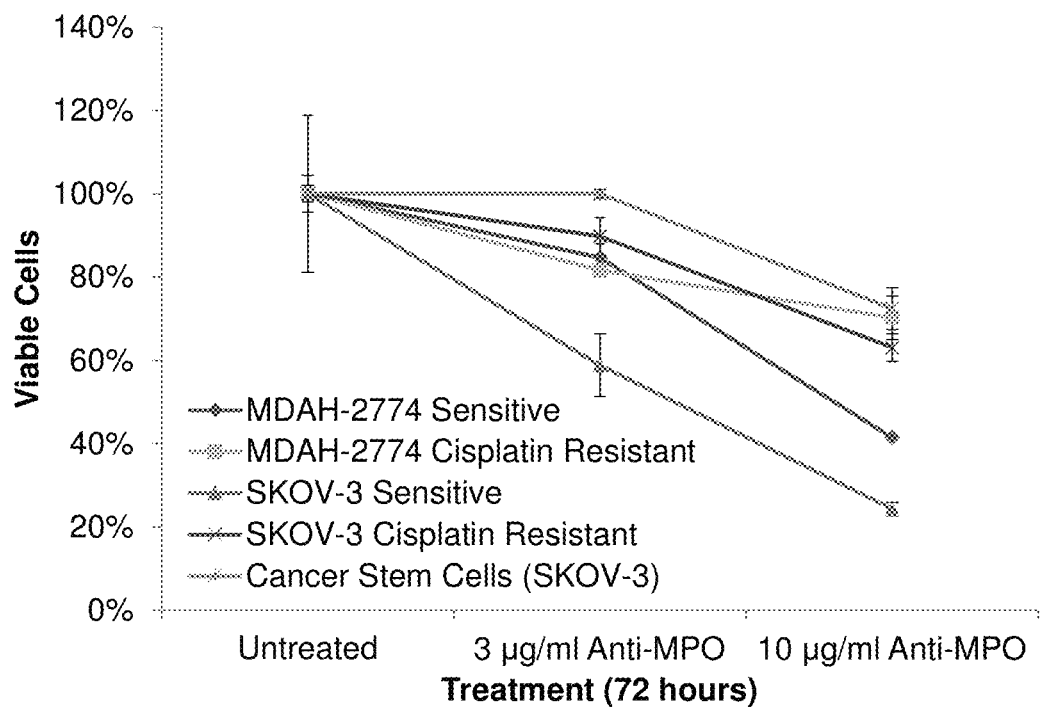
FIGS. 17A-17D. Cell viability in sensitive and cisplatin resistant EOC cells after treatment with MPO antibody.
Figure 17B:
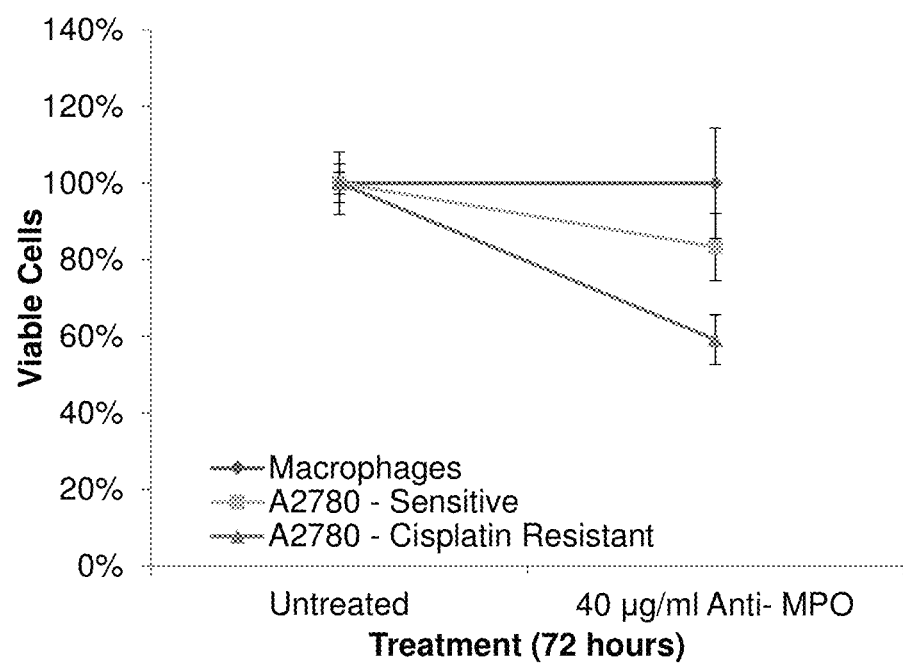
Figure 17C:
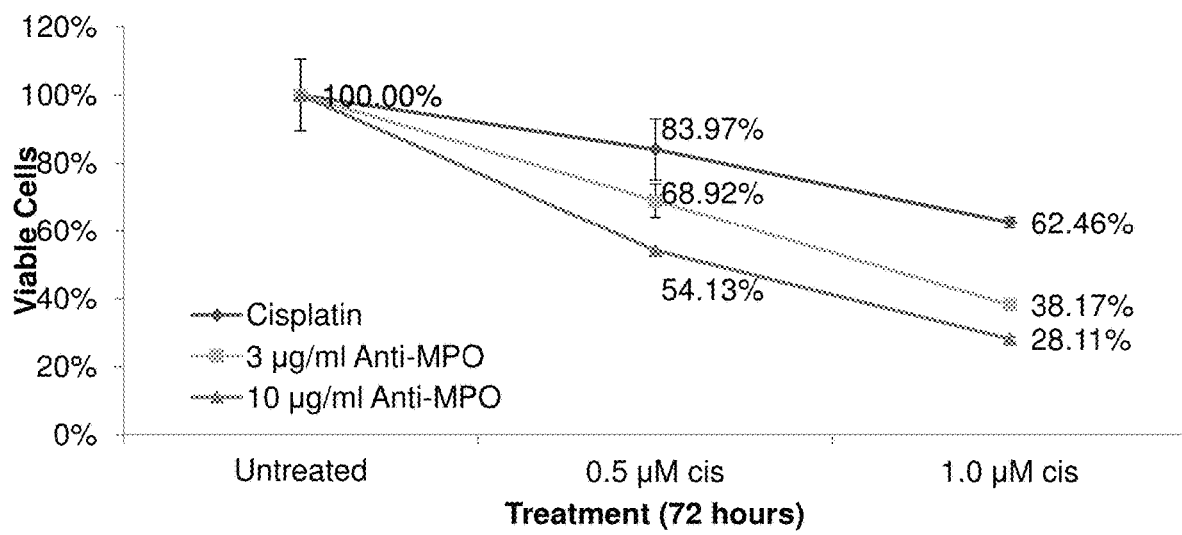
Figure 17D:
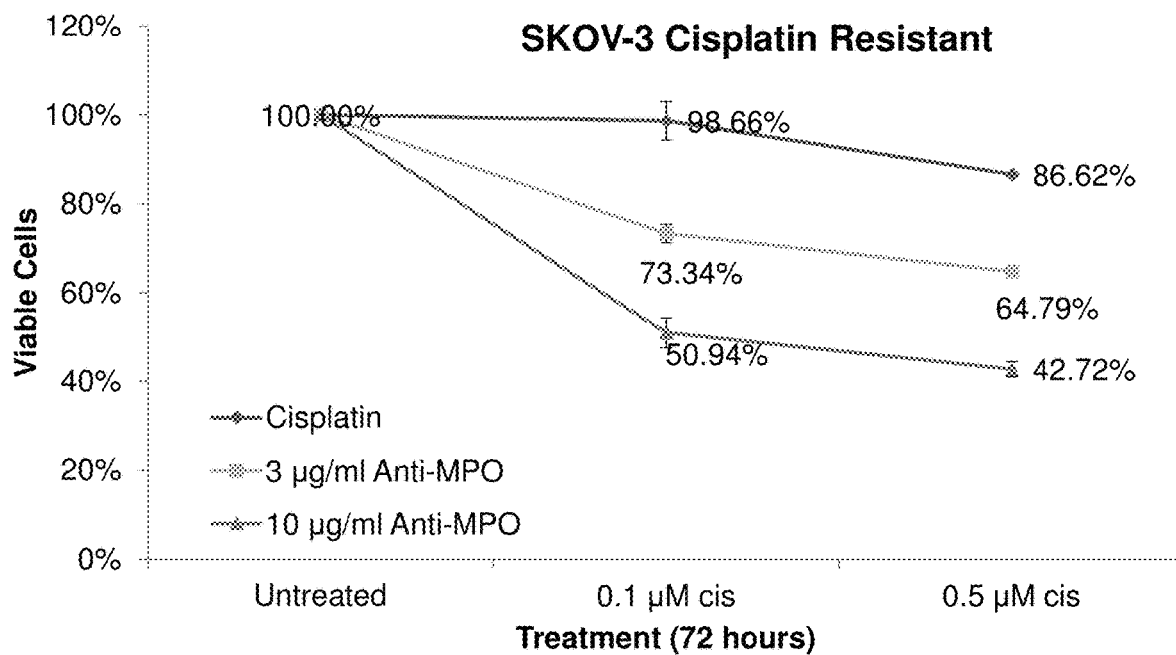

Treatment with the MPO antibody also decreased cell viability, albeit to a lesser extent than was observed with CD11b antibody treatment (FIGS. 17A-17B). Combination of MPO antibody with increasing concentrations of cisplatin was able to enhance cell death at the higher concentration of MPO antibody (FIGS. 17C-17D).

Figure 18:
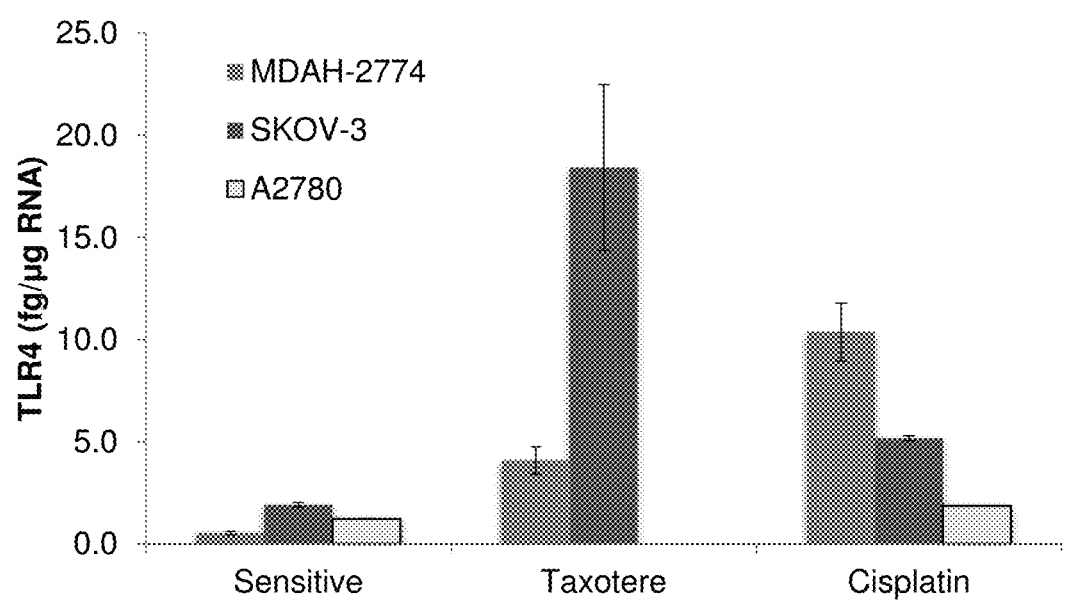

CD11b has been implicated with TLR4 in ovarian cancer. As disclosed herein, expression of TLR4 increases in chemoresistant EOC cells as compared to their chemosensitive counterparts (FIG. 18).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. In particular embodiments, lack of a material effect is evidenced by lack of a statistically-significant reduction in the embodiment's ability to kill ovarian cancer cells in vitro or in vivo.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

ADDITIONAL REFERENCES

1. Rajput et al., "TLR is a Novel Determinant of the Response to Paclitaxel in Breast Cancer," *Mol Cancer Ther.*, 12(8):1676-1687, 2013.
2. Podolnikova et al., "Ligand Recognition Specificity of Leukocyte Integrin αMβ2 (Mac-1, CD11b/CD18) and Its Functional Consequences," *Biochemistry*, 54(6):1408-1420, 2015.
3. Sadhu et al, "CD11c/CD18: Novel Ligands and a Role in Delayed-Type Hypersensitivity," *J Leuko Biol.*, 81(6):1395-1403, 2007.

What is claimed is:

1. A method of inducing apoptosis of cells of an ovarian tumor in a subject in need thereof comprising administering to the subject a therapeutically effective amount of an anti-MPO antibody and a therapeutically effective amount of an anti-CD11b antibody, thereby inducing apoptosis of cells of the ovarian tumor in the subject.

2. The method of claim 1, further comprising administering a therapeutically effective amount of an anti-CD18 antibody.

3. The method of claim 1, further comprising administering a therapeutically effective amount of an anti-integrin aV antibody.

4. The method of claim 1, further comprising administering a therapeutically effective amount of an anti-integrin β1 antibody.

5. The method of claim 1, further comprising administering a therapeutically effective amount of NIF.

6. The method of claim 1, further comprising administering a therapeutically effective amount of Abciximab.

7. The method of claim 1, wherein the ovarian tumor is a pre-malignant solid tumor or a malignant solid tumor.

8. The method of claim 1, wherein the ovarian tumor is a chemoresistant solid tumor.

9. The method of claim 1, wherein the administering causes an anti-cancer effect in the subject.

10. The method of claim 1, wherein the anti-MPO antibody is administered as a protein or as nucleic acid(s) encoding the protein.

11. The method of claim 1, which is a method of treating ovarian cancer.

12. The method of claim 11, wherein the ovarian cancer comprises chemosensitive cancer cells.

13. The method of claim 11, wherein the ovarian cancer comprises chemoresistant cancer cells.

14. The method of claim 11, wherein the ovarian cancer comprises cancer stem cells.

15. The method of claim 2, wherein the anti-CD18 antibody is administered as a protein or as nucleic acid(s) encoding the protein.

16. The method of claim 3, wherein the anti-integrin aV antibody is administered as a protein or as nucleic acid(s) encoding the protein.

17. The method of claim 4, wherein the anti-β1 antibody is administered as a protein or as nucleic acid(s) encoding the protein.

18. The method of claim 5, wherein the NIF is administered as a protein or as nucleic acid(s) encoding the protein.

* * * * *

SEQUENCE LISTING

<160> NUMBER OF SEQ ID NOS: 18

<210> SEQ ID NO 1
<211> LENGTH: 1152
<212> TYPE: PRT
<213> ORGANISM: Homo sapiens

<400> SEQUENCE: 1

```
Met Ala Leu Arg Val Leu Leu Leu Thr Ala Leu Thr Leu Cys His Gly
 1               5                  10                  15

Phe Asn Leu Asp Thr Glu Asn Ala Met Thr Phe Gln Glu Asn Ala Arg
            20                  25                  30

Gly Phe Gly Gln Ser Val Val Gln Leu Gln Gly Ser Arg Val Val Val
        35                  40                  45

Gly Ala Pro Gln Glu Ile Val Ala Ala Asn Gln Arg Gly Ser Leu Tyr
    50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
        115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Phe Glu His Glu Met Ser Gln
            340                 345                 350

Glu Gly Phe Ser Ala Ala Ile Thr Ser Asn Gly Pro Leu Leu Ser Thr
        355                 360                 365
```

```
Val Gly Ser Tyr Asp Trp Ala Gly Gly Val Phe Leu Tyr Thr Ser Lys
    370                 375                 380
Glu Lys Ser Thr Phe Ile Asn Met Thr Arg Val Asp Ser Asp Met Asn
385                 390                 395                 400
Asp Ala Tyr Leu Gly Tyr Ala Ala Ile Ile Leu Arg Asn Arg Val
                    405                 410                 415
Gln Ser Leu Val Leu Gly Ala Pro Arg Tyr Gln His Ile Gly Leu Val
            420                 425                 430
Ala Met Phe Arg Gln Asn Thr Gly Met Trp Glu Ser Asn Ala Asn Val
        435                 440                 445
Lys Gly Thr Gln Ile Gly Ala Tyr Phe Gly Ala Ser Leu Cys Ser Val
450                 455                 460
Asp Val Asp Ser Asn Gly Ser Thr Asp Leu Val Leu Ile Gly Ala Pro
465                 470                 475                 480
His Tyr Tyr Glu Gln Thr Arg Gly Gly Gln Val Ser Val Cys Pro Leu
                    485                 490                 495
Pro Arg Gly Arg Ala Arg Trp Gln Cys Asp Ala Val Leu Tyr Gly Glu
            500                 505                 510
Gln Gly Gln Pro Trp Gly Arg Phe Gly Ala Ala Leu Thr Val Leu Gly
        515                 520                 525
Asp Val Asn Gly Asp Lys Leu Thr Asp Val Ala Ile Gly Ala Pro Gly
    530                 535                 540
Glu Glu Asp Asn Arg Gly Ala Val Tyr Leu Phe His Gly Thr Ser Gly
545                 550                 555                 560
Ser Gly Ile Ser Pro Ser His Ser Gln Arg Ile Ala Gly Ser Lys Leu
                565                 570                 575
Ser Pro Arg Leu Gln Tyr Phe Gly Gln Ser Leu Ser Gly Gly Gln Asp
            580                 585                 590
Leu Thr Met Asp Gly Leu Val Asp Leu Thr Val Gly Ala Gln Gly His
        595                 600                 605
Val Leu Leu Leu Arg Ser Gln Pro Val Leu Arg Val Lys Ala Ile Met
    610                 615                 620
Glu Phe Asn Pro Arg Glu Val Ala Arg Asn Val Phe Glu Cys Asn Asp
625                 630                 635                 640
Gln Val Val Lys Gly Lys Glu Ala Gly Glu Val Arg Val Cys Leu His
                645                 650                 655
Val Gln Lys Ser Thr Arg Asp Arg Leu Arg Glu Gly Gln Ile Gln Ser
            660                 665                 670
Val Val Thr Tyr Asp Leu Ala Leu Asp Ser Gly Arg Pro His Ser Arg
        675                 680                 685
Ala Val Phe Asn Glu Thr Lys Asn Ser Thr Arg Arg Gln Thr Gln Val
    690                 695                 700
Leu Gly Leu Thr Gln Thr Cys Glu Thr Leu Lys Leu Gln Leu Pro Asn
705                 710                 715                 720
Cys Ile Glu Asp Pro Val Ser Pro Ile Val Leu Arg Leu Asn Phe Ser
                725                 730                 735
Leu Val Gly Thr Pro Leu Ser Ala Phe Gly Asn Leu Arg Pro Val Leu
            740                 745                 750
Ala Glu Asp Ala Gln Arg Leu Phe Thr Ala Leu Phe Pro Phe Glu Lys
        755                 760                 765
Asn Cys Gly Asn Asp Asn Ile Cys Gln Asp Asp Leu Ser Ile Thr Phe
    770                 775                 780
Ser Phe Met Ser Leu Asp Cys Leu Val Val Gly Gly Pro Arg Glu Phe
```

```
            785                 790                 795                 800
Asn Val Thr Val Thr Val Arg Asn Asp Gly Glu Asp Ser Tyr Arg Thr
                805                 810                 815

Gln Val Thr Phe Phe Pro Leu Asp Leu Ser Tyr Arg Lys Val Ser
                820                 825                 830

Thr Leu Gln Asn Gln Arg Ser Gln Arg Ser Trp Arg Leu Ala Cys Glu
                835                 840                 845

Ser Ala Ser Ser Thr Glu Val Ser Gly Ala Leu Lys Ser Thr Ser Cys
    850                 855                 860

Ser Ile Asn His Pro Ile Phe Pro Glu Asn Ser Glu Val Thr Phe Asn
865                 870                 875                 880

Ile Thr Phe Asp Val Asp Ser Lys Ala Ser Leu Gly Asn Lys Leu Leu
                885                 890                 895

Leu Lys Ala Asn Val Thr Ser Glu Asn Asn Met Pro Arg Thr Asn Lys
                900                 905                 910

Thr Glu Phe Gln Leu Glu Leu Pro Val Lys Tyr Ala Val Tyr Met Val
                915                 920                 925

Val Thr Ser His Gly Val Ser Thr Lys Tyr Leu Asn Phe Thr Ala Ser
    930                 935                 940

Glu Asn Thr Ser Arg Val Met Gln His Gln Tyr Gln Val Ser Asn Leu
945                 950                 955                 960

Gly Gln Arg Ser Leu Pro Ile Ser Leu Val Phe Leu Val Pro Val Arg
                965                 970                 975

Leu Asn Gln Thr Val Ile Trp Asp Arg Pro Gln Val Thr Phe Ser Glu
                980                 985                 990

Asn Leu Ser Ser Thr Cys His Thr Lys Glu Arg Leu Pro Ser His Ser
                995                1000                1005

Asp Phe Leu Ala Glu Leu Arg Lys Ala Pro Val Val Asn Cys Ser
    1010                1015                1020

Ile Ala Val Cys Gln Arg Ile Gln Cys Asp Ile Pro Phe Phe Gly
    1025                1030                1035

Ile Gln Glu Glu Phe Asn Ala Thr Leu Lys Gly Asn Leu Ser Phe
    1040                1045                1050

Asp Trp Tyr Ile Lys Thr Ser His Asn His Leu Leu Ile Val Ser
    1055                1060                1065

Thr Ala Glu Ile Leu Phe Asn Asp Ser Val Phe Thr Leu Leu Pro
    1070                1075                1080

Gly Gln Gly Ala Phe Val Arg Ser Gln Thr Glu Thr Lys Val Glu
    1085                1090                1095

Pro Phe Glu Val Pro Asn Pro Leu Pro Leu Ile Val Gly Ser Ser
    1100                1105                1110

Val Gly Gly Leu Leu Leu Leu Ala Leu Ile Thr Ala Ala Leu Tyr
    1115                1120                1125

Lys Leu Gly Phe Phe Lys Arg Gln Tyr Lys Asp Met Met Ser Glu
    1130                1135                1140

Gly Gly Pro Pro Gly Ala Glu Pro Gln
    1145                1150
```

<210> SEQ ID NO 2
<211> LENGTH: 798
<212> TYPE: PRT
<213> ORGANISM: Homo sapiens

<400> SEQUENCE: 2

```
Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
                35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile His
                100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
        130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
            195                 200                 205

Ser Glu Gln Asn Cys Thr Thr Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
        290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
            355                 360                 365

Gln Leu Ile Ile Asp Ala Tyr Asn Ser Leu Ser Ser Glu Val Ile Leu
        370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
```

```
                420             425             430
Asn Lys Cys Pro Lys Lys Asp Ser Asp Ser Phe Lys Ile Arg Pro Leu
            435             440             445

Gly Phe Thr Glu Glu Val Glu Val Ile Leu Gln Tyr Ile Cys Glu Cys
    450             455             460

Glu Cys Gln Ser Glu Gly Ile Pro Glu Ser Pro Lys Cys His Glu Gly
465             470             475             480

Asn Gly Thr Phe Glu Cys Gly Ala Cys Arg Cys Asn Glu Gly Arg Val
            485             490             495

Gly Arg His Cys Glu Cys Ser Thr Asp Glu Val Asn Ser Glu Asp Met
        500             505             510

Asp Ala Tyr Cys Arg Lys Glu Asn Ser Ser Glu Ile Cys Ser Asn Asn
        515             520             525

Gly Glu Cys Val Cys Gly Gln Cys Val Cys Arg Lys Arg Asp Asn Thr
        530             535             540

Asn Glu Ile Tyr Ser Gly Lys Phe Cys Glu Cys Asp Asn Phe Asn Cys
545             550             555             560

Asp Arg Ser Asn Gly Leu Ile Cys Gly Gly Asn Gly Val Cys Lys Cys
            565             570             575

Arg Val Cys Glu Cys Asn Pro Asn Tyr Thr Gly Ser Ala Cys Asp Cys
            580             585             590

Ser Leu Asp Thr Ser Thr Cys Glu Ala Ser Asn Gly Gln Ile Cys Asn
        595             600             605

Gly Arg Gly Ile Cys Glu Cys Gly Val Cys Lys Cys Thr Asp Pro Lys
        610             615             620

Phe Gln Gly Gln Thr Cys Glu Met Cys Gln Thr Cys Leu Gly Val Cys
625             630             635             640

Ala Glu His Lys Glu Cys Val Gln Cys Arg Ala Phe Asn Lys Gly Glu
            645             650             655

Lys Lys Asp Thr Cys Thr Gln Glu Cys Ser Tyr Phe Asn Ile Thr Lys
            660             665             670

Val Glu Ser Arg Asp Lys Leu Pro Gln Pro Val Gln Pro Asp Pro Val
        675             680             685

Ser His Cys Lys Glu Lys Asp Val Asp Asp Cys Trp Phe Tyr Phe Thr
        690             695             700

Tyr Ser Val Asn Gly Asn Asn Glu Val Met Val His Val Val Glu Asn
705             710             715             720

Pro Glu Cys Pro Thr Gly Pro Asp Ile Ile Pro Ile Val Ala Gly Val
            725             730             735

Val Ala Gly Ile Val Leu Ile Gly Leu Ala Leu Leu Leu Ile Trp Lys
            740             745             750

Leu Leu Met Ile Ile His Asp Arg Arg Glu Phe Ala Lys Phe Glu Lys
        755             760             765

Glu Lys Met Asn Ala Lys Trp Asp Thr Gly Glu Asn Pro Ile Tyr Lys
        770             775             780

Ser Ala Val Thr Thr Val Val Asn Pro Lys Tyr Glu Gly Lys
785             790             795

<210> SEQ ID NO 3
<211> LENGTH: 450
<212> TYPE: PRT
<213> ORGANISM: Artificial sequence
<220> FEATURE:
<223> OTHER INFORMATION: Abciximab heavy chain 1
```

```
<400> SEQUENCE: 3

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Val His Trp Val Lys Gln Arg Pro Glu Gln Gly Leu Glu Trp Ile
        35                  40                  45

Gly Arg Ile Asp Pro Ala Asn Gly Tyr Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Pro Leu Tyr Asp Tyr Tyr Ala Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 4
<211> LENGTH: 214
<212> TYPE: PRT
<213> ORGANISM: Artificial sequence
<220> FEATURE:
<223> OTHER INFORMATION: Abciximab light chain 1

<400> SEQUENCE: 4

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Met Gly Leu Ile
        35                  40                  45

Tyr Tyr Gly Thr Asn Leu Val Asp Gly Val Pro Ser Arg Phe Ser Gly
    50                  55                  60

Ser Gly Ser Gly Ala Asp Tyr Ser Leu Thr Ile Ser Ser Leu Asp Ser
65                  70                  75                  80

Glu Asp Phe Ala Asp Tyr Tyr Cys Val Gln Tyr Ala Gln Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 5
<211> LENGTH: 450
<212> TYPE: PRT
<213> ORGANISM: Artificial sequence
<220> FEATURE:
<223> OTHER INFORMATION: Abciximab heavy chain 2

<400> SEQUENCE: 5

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Val His Trp Val Lys Gln Arg Pro Glu Gln Gly Leu Glu Trp Ile
```

```
            35                  40                  45
Gly Arg Ile Asp Pro Ala Asn Gly Tyr Thr Lys Tyr Asp Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Val Arg Pro Leu Tyr Asp Tyr Ala Met Asp Tyr Trp Gly Gln Gly
                100                 105                 110

Thr Ser Val Thr Val Ser Ser Ala Lys Thr Thr Ala Pro Ser Val Tyr
                115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Thr Ser Ser
                180                 185                 190

Thr Trp Pro Ser Gln Ser Ile Thr Cys Asn Val Ala His Pro Ala Ser
                195                 200                 205

Ser Thr Lys Val Asp Lys Lys Ile Glu Pro Arg Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
 450
```

-continued

```
<210> SEQ ID NO 6
<211> LENGTH: 214
<212> TYPE: PRT
<213> ORGANISM: Artificial sequence
<220> FEATURE:
<223> OTHER INFORMATION: Abciximab light chain 2

<400> SEQUENCE: 6
```

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Met Gly Leu Ile
        35                  40                  45

Tyr Tyr Gly Thr Asn Leu Val Asp Gly Val Pro Ser Arg Phe Ser Gly
    50                  55                  60

Ser Gly Ser Gly Ala Asp Tyr Ser Leu Thr Ile Ser Ser Leu Asp Ser
65                  70                  75                  80

Glu Asp Phe Ala Asp Tyr Tyr Cys Val Gln Tyr Ala Gln Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

```
<210> SEQ ID NO 7
<211> LENGTH: 885
<212> TYPE: PRT
<213> ORGANISM: Ancylostoma caninum

<400> SEQUENCE: 7
```

Gly Gly Cys Gly Ala Ala Thr Thr Cys Ala Cys Cys Ala Thr Gly Gly
1               5                   10                  15

Ala Gly Gly Cys Cys Thr Ala Thr Cys Thr Thr Gly Thr Gly Gly Thr
            20                  25                  30

Cys Thr Thr Ala Ala Thr Thr Gly Cys Cys Ala Thr Thr Gly Cys Thr
        35                  40                  45

Gly Gly Cys Ala Thr Ala Gly Cys Thr Cys Ala Thr Thr Cys Cys Ala
    50                  55                  60

Ala Thr Gly Ala Ala Cys Ala Cys Ala Cys Cys Thr Gly Ala Gly Gly
65                  70                  75                  80

Gly Thr Gly Cys Cys Cys Gly Cys Ala Gly Ala Thr Gly Gly Ala
                85                  90                  95

-continued

```
Ala Cys Ala Gly Ala Ala Ala Thr Gly Cys Cys Cys Gly Gly Thr Thr
            100                 105                 110

Thr Cys Ala Ala Cys Gly Ala Cys Thr Cys Gly Ala Thr Thr Ala Gly
        115                 120                 125

Gly Cys Thr Thr Cys Ala Ala Thr Thr Thr Thr Thr Ala Gly Cys Ala
    130                 135                 140

Ala Thr Gly Cys Ala Cys Ala Ala Thr Gly Gly Thr Thr Ala Cys Ala
145                 150                 155                 160

Gly Ala Thr Cys Ala Ala Ala Ala Cys Thr Thr Gly Cys Gly Cys Thr
                165                 170                 175

Ala Gly Gly Thr Cys Ala Cys Ala Thr Cys Ala Gly Cys Ala Thr Ala
            180                 185                 190

Ala Cys Thr Gly Ala Ala Gly Ala Ala Thr Cys Cys Gly Ala Ala Ala
        195                 200                 205

Gly Thr Gly Ala Cys Gly Ala Thr Gly Ala Thr Gly Ala Cys Gly Ala
    210                 215                 220

Thr Thr Thr Cys Gly Gly Thr Thr Thr Thr Thr Thr Ala Cys Cys Cys
225                 230                 235                 240

Gly Ala Thr Thr Thr Cys Gly Cys Thr Cys Cys Ala Ala Gly Gly Gly
                245                 250                 255

Cys Ala Thr Cys Gly Ala Ala Ala Ala Thr Gly Ala Gly Ala Thr Ala
            260                 265                 270

Thr Cys Thr Gly Gly Ala Ala Thr Ala Thr Gly Ala Cys Thr Gly Thr
        275                 280                 285

Gly Ala Ala Gly Cys Thr Gly Ala Ala Ala Ala Ala Ala Gly Cys Gly
    290                 295                 300

Cys Cys Thr Ala Cys Ala Thr Gly Thr Cys Gly Gly Cys Thr Ala Gly
305                 310                 315                 320

Ala Ala Ala Thr Thr Gly Cys Thr Cys Gly Gly Ala Cys Ala Gly Thr
                325                 330                 335

Thr Cys Thr Thr Cys Thr Cys Cys Ala Cys Cys Ala Gly Ala Gly Gly
            340                 345                 350

Gly Cys Thr Ala Cys Gly Ala Thr Gly Ala Ala Ala Ala Cys Ala Ala
        355                 360                 365

Gly Thr Ala Thr Ala Thr Thr Thr Thr Cys Gly Ala Ala Ala Ala Cys
    370                 375                 380

Thr Cys Ala Ala Ala Cys Ala Ala Thr Ala Thr Cys Ala Gly Thr Gly
385                 390                 395                 400

Ala Ala Gly Cys Thr Gly Cys Thr Cys Thr Gly Ala Ala Gly Gly Cys
                405                 410                 415

Cys Ala Thr Gly Ala Thr Cys Thr Cys Gly Thr Gly Gly Gly Cys Ala
            420                 425                 430

Ala Ala Ala Gly Ala Gly Gly Cys Thr Thr Thr Cys Ala Ala Cys Cys
        435                 440                 445

Thr Ala Ala Ala Thr Ala Ala Ala Ala Cys Ala Ala Ala Ala Gly Ala
    450                 455                 460

Ala Gly Gly Ala Gly Ala Ala Gly Gly Ala Gly Thr Thr Cys Thr Gly
465                 470                 475                 480

Thr Ala Cys Cys Gly Gly Thr Cys Gly Ala Ala Cys Cys Ala Cys Gly
                485                 490                 495

Ala Cys Ala Thr Ala Thr Cys Ala Ala Ala Cys Thr Thr Cys Gly Cys
            500                 505                 510

Thr Ala Ala Thr Cys Thr Gly Gly Cys Thr Thr Gly Gly Gly Ala Cys
```

```
                515                 520                 525
Gly Cys Gly Cys Gly Thr Gly Ala Ala Ala Gly Thr Thr Gly
            530                 535                 540
Gly Thr Thr Gly Cys Gly Cys Ala Gly Thr Thr Gly Thr Ala Ala
545                 550                 555                 560
Cys Thr Gly Cys Cys Thr Thr Thr Gly Gly Ala Gly Ala Ala
                565                 570                 575
Ala Thr Cys Gly Ala Thr Gly Ala Thr Gly Ala Ala Cys Cys Ala
            580                 585                 590
Ala Cys Cys Ala Thr Gly Ala Thr Gly Gly Ala Gly Ala Ala Cys
        595                 600                 605
Cys Thr Ala Thr Gly Cys Ala Ala Cys Ala Cys Cys Ala Thr Cys
    610                 615                 620
Cys Ala Thr Gly Thr Ala Gly Thr Cys Thr Gly Cys Ala Cys Thr
625                 630                 635                 640
Ala Cys Cys Cys Gly Ala Ala Ala Thr Ala Ala Cys Ala Ala
                645                 650                 655
Ala Ala Cys Thr Gly Ala Ala Gly Gly Ala Cys Ala Gly Cys Cys Gly
            660                 665                 670
Ala Thr Thr Thr Ala Cys Ala Ala Gly Gly Thr Ala Gly Gly Ala
            675                 680                 685
Cys Ala Cys Cys Ala Thr Gly Cys Gly Ala Cys Gly Ala Thr Thr Gly
    690                 695                 700
Cys Ala Gly Thr Gly Ala Ala Thr Ala Cys Ala Cys Ala Ala Ala
705                 710                 715                 720
Ala Ala Ala Gly Cys Ala Gly Ala Cys Ala Ala Thr Ala Cys Cys Ala
                725                 730                 735
Cys Gly Thr Cys Thr Gly Cys Gly Gly Ala Thr Cys Cys Gly Gly Thr
            740                 745                 750
Gly Thr Gly Thr Ala Thr Thr Cys Cys Gly Gly Ala Thr Gly Ala Cys
            755                 760                 765
Gly Gly Ala Gly Thr Cys Thr Gly Cys Thr Thr Thr Ala Thr Thr Gly
            770                 775                 780
Gly Cys Thr Cys Gly Ala Ala Ala Cys Cys Gly Ala Thr Thr Ala
785                 790                 795                 800
Cys Gly Ala Thr Ala Gly Cys Ala Ala Gly Gly Ala Gly Thr Thr Thr
            805                 810                 815
Thr Ala Thr Cys Gly Ala Thr Cys Cys Gly Ala Gly Ala Gly Thr
        820                 825                 830
Thr Ala Thr Gly Ala Ala Thr Ala Ala Gly Thr Cys Gly Ala Gly Ala
            835                 840                 845
Cys Gly Thr Ala Thr Ala Ala Ala Gly Ala Ala Gly Cys Cys Ala Ala
        850                 855                 860
Gly Gly Cys Ala Ala Cys Gly Thr Ala Ala Gly Cys Gly Ala Gly Ala
865                 870                 875                 880
Ala Thr Thr Thr Cys
            885

<210> SEQ ID NO 8
<211> LENGTH: 37
<212> TYPE: PRT
<213> ORGANISM: Homo sapiens

<400> SEQUENCE: 8
```

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 9
<211> LENGTH: 20
<212> TYPE: DNA
<213> ORGANISM: Artificial sequence
<220> FEATURE:
<223> OTHER INFORMATION: beta-actin sense primer

<400> SEQUENCE: 9
atgacttagt tgcgttacac                                            20

<210> SEQ ID NO 10
<211> LENGTH: 20
<212> TYPE: DNA
<213> ORGANISM: Artificial sequence
<220> FEATURE:
<223> OTHER INFORMATION: beta-actin antisense primer

<400> SEQUENCE: 10
aataaagcca tgccaatctc                                            20

<210> SEQ ID NO 11
<211> LENGTH: 20
<212> TYPE: DNA
<213> ORGANISM: Artificial sequence
<220> FEATURE:
<223> OTHER INFORMATION: CD11b sense primer

<400> SEQUENCE: 11
tcggcggatg aaggagtttg                                            20

<210> SEQ ID NO 12
<211> LENGTH: 22
<212> TYPE: DNA
<213> ORGANISM: Artificial sequence
<220> FEATURE:
<223> OTHER INFORMATION: CD11b antisense primer

<400> SEQUENCE: 12
tcttgggtta gggttgttct gg                                         22

<210> SEQ ID NO 13
<211> LENGTH: 18
<212> TYPE: DNA
<213> ORGANISM: Artificial sequence
<220> FEATURE:
<223> OTHER INFORMATION: Integrin alphaV sense primer

<400> SEQUENCE: 13
gactcctgct acctctgt                                              18

<210> SEQ ID NO 14
<211> LENGTH: 18
<212> TYPE: DNA
<213> ORGANISM: Artificial sequence
<220> FEATURE:
<223> OTHER INFORMATION: Integrin alphaV antisense primer

<400> SEQUENCE: 14

```
gcgaagccga agtaactt                                                      18

<210> SEQ ID NO 15
<211> LENGTH: 21
<212> TYPE: DNA
<213> ORGANISM: Artificial sequence
<220> FEATURE:
<223> OTHER INFORMATION: Integrin beta1 sense primer

<400> SEQUENCE: 15
gacttgagac aggatggtta c                                                  21

<210> SEQ ID NO 16
<211> LENGTH: 23
<212> TYPE: DNA
<213> ORGANISM: Artificial sequence
<220> FEATURE:
<223> OTHER INFORMATION: Integrin beta1 antisense primer

<400> SEQUENCE: 16
tgatttcaat agtccaggaa gaa                                                23

<210> SEQ ID NO 17
<211> LENGTH: 18
<212> TYPE: DNA
<213> ORGANISM: Artificial sequence
<220> FEATURE:
<223> OTHER INFORMATION: MPO sense primer

<400> SEQUENCE: 17
gcgtgtccga gcctctga                                                      18

<210> SEQ ID NO 18
<211> LENGTH: 22
<212> TYPE: DNA
<213> ORGANISM: Artificial sequence
<220> FEATURE:
<223> OTHER INFORMATION: MPO antisense primer

<400> SEQUENCE: 18
tcccaccaaa accgatcacc at                                                 22
```